United States Patent
Francois et al.

(10) Patent No.: US 11,434,190 B2
(45) Date of Patent: Sep. 6, 2022

(54) INHIBITORS OF SOX18 PROTEIN ACTIVITY FOR TREATING ANGIOGENESIS-AND/OR LYMPHANGIOGENESIS-RELATED DISEASES

(71) Applicant: The University of Queensland

(72) Inventors: Mathias Francois, St. Lucia (AU); Johannes Zuegg, Wynnum (AU); Jeroen Overman, The Hague (NL); Sreeman Kumar Mamidyala, Hyderabad (IN); Angela Aguslyarti Salim, Durack (AU); Frank Roger Fontaine, Kenmore (AU); Matthew Allister Cooper, Cambridge (GB); Robert John Capon, Pullenvale (AU); Avril Alexis Barbara Robertson, Kenmore (AU)

(73) Assignee: THE UNIVERSITY OF QUEENSLAND, Brisbane (AU)

( * ) Notice: Subject to any disclaimer, the term of this patent is extended or adjusted under 35 U.S.C. 154(b) by 12 days.

(21) Appl. No.: 16/472,882

(22) PCT Filed: Dec. 21, 2017

(86) PCT No.: PCT/AU2017/051439
§ 371 (c)(1),
(2) Date: Jun. 23, 2019

(87) PCT Pub. No.: WO2018/112545
PCT Pub. Date: Jun. 28, 2018

(65) Prior Publication Data
US 2019/0337880 A1 Nov. 7, 2019

(30) Foreign Application Priority Data
Dec. 23, 2016 (AU) .......................... AU2016905362

(51) Int. Cl.
| C07C 63/66 | (2006.01) |
| C07C 39/15 | (2006.01) |
| C07C 43/215 | (2006.01) |
| C07C 63/331 | (2006.01) |
| C07C 233/65 | (2006.01) |
| A61P 35/00 | (2006.01) |

(52) U.S. Cl.
CPC .............. *C07C 63/66* (2013.01); *A61P 35/00* (2018.01); *C07C 39/15* (2013.01); *C07C 43/215* (2013.01); *C07C 63/331* (2013.01); *C07C 233/65* (2013.01)

(58) Field of Classification Search
CPC ....... C07C 63/66; C07C 39/15; C07C 43/215; C07C 63/331; C07C 233/65; A61P 35/00
USPC ....................................................... 514/617
See application file for complete search history.

(56) References Cited

U.S. PATENT DOCUMENTS

2008/0234369 A1    9/2008   Li et al.

FOREIGN PATENT DOCUMENTS

| CN | 102050759 A | 5/2011 |
| CN | 101062043 B | 6/2011 |
| DE | WO2001074753 | * 11/2001 |
| EP | 0292202 A1 | 11/1988 |
| JP | 2007530427 A | 11/2007 |
| JP | 2016516007 A | 6/2016 |
| WO | 2001/074753 A1 | 11/2001 |
| WO | 2005007635 A2 | 1/2005 |
| WO | 2005007635 A3 | 1/2005 |
| WO | 2001/119866 A1 | 9/2011 |
| WO | 2014/134202 A1 | 9/2014 |

OTHER PUBLICATIONS

Eskander et al. Therapeutic Advances in Medical Oncology6(6) 280-292 (2014) (Year: 2014).*
MedicineNet.com (http://www.medterms.com, 2004) (Year: 2004).*
Berger et al. Nature Reviews Cancer vol. 8, pp. 592-603 (2008) (Year: 2008).*
Kamb, A. in Nature Reviews 4, 161-165 (2005) (Year: 2005).*
Angiosarcoma at http://web.archive.org/web/ 20151110114646/ https://emedicine.medscape.com/article/276512-overview (Year: 2015).*
Youngren et al. Breast Cancer Research and Treatment 94:37-46 (2005) (Year: 2005).*
Zhang et al. Oncology Reports 35:3721-3727 (2016) (Year: 2016).*
Petrovic et al. PLOS One 1-21 (2015); DOI:10.1371/journal.pone. 0143591 (Year: 2015).*
Iqbal et al. Molecular Biology International vol. 2014, pp. 1-9 (Year: 2014).*
Cai, Yu-Chen et al., "Anti tumor activity and mechanisms of a novel vascular disrupting agent, (Z)-3,4',5-trimethoxylstilbene-3'-O-phosphate disodium (M410)" Invest. New Drugs, The Journal of New Anticancer Agents, 2011, 29:300-322, p. 12.
Fontaine et al., "Small-Molecule Inhibitors of the SOX18 Transcription Factor" Cell Chemical Biology 2017, 24, 346-359, p. 15.
J. Wang et al., "Pathway-related molecules of VEGFC/D-VEGFR3/NRP2 axis in tumor lymphangiogenesis and lymphatic metastasis" Clinica Chimica Acta 2016, 461: 165-171, pp. 7.
Mamidyala et al., "Efficient synthesis of anacardic acid analogues and their antibacterial activities" Bioorganic & Medicinal Chemistry Letters 2013, 23: 1667-1670, pp. 4.
S. Nomura et al., "Development of Tetrachlorophthalimides as Liver X Receptor B (LXRß)-Selective Agonists" ChemMed Chem 2016, 11:2347-2360, pp. 14.

(Continued)

*Primary Examiner* — Yevgeny Valenrod
(74) *Attorney, Agent, or Firm* — Patterson + Sheridan, LLP

(57) ABSTRACT

Disclosed are compounds of a formula provided herein that show efficacy in the inhibition of SOX18 protein activity, and in particular with respect to the ability of SOX18 to bind DNA and/or particular protein partners. Further, methods of treating angiogenesis- and/or lymphangiogenesis-related diseases, disorders or conditions, such as cancer metastasis and vascular cancers, are provided herein.

15 Claims, 41 Drawing Sheets

(56) References Cited

OTHER PUBLICATIONS

Gong et al., "In vivo and in vitro evaluation of erianin, a novel anti-angiogenic agent" European Journal of Cancer 2004, 40: 1554-1565, pp. 12.
EESR dated Sep. 30, 2020 for Applicatin No. PCT/AU2017/051439.
International Search Report and Written Opinion for PCT/AU2017/051439, dated Mar. 5, 2018.
Lam, F., et al., "ZJU-6, A novel drivative of Erianin, shows potent anti-tubulin polymerisation and anti-angiogenic activities," Investigational New Drugs, 2012, 30(5), pp. 1899-1907.
Liu, Q., et al., "Synthesis of 3'-methoxy-E-diethystilbestrol and its analogs as tumor angiogenesis inhibitor," Steroids, 2012, 77(5), pp. 419-423.
Bertl, E., et al., "Identification of novel inhibitors of angiogenesis using a human in vitro anti-angiogenic assay," International Journal of Cancer Prevention (2004), 1(1), pp. 47-61.
Geny, C., et al., "Anancardic Acids from Knema hookeriana as Modulators of Bcl-xL/Bak and Mcl-1/Bid Interactions," Journal of Natural Products (2016), 79(4), pp. 838-844.

Van Cruijsen, H., et al., "Epidermal growth factor receptor and aniogenesis: opportunities for combined anticancer strategies," International Journal of Cancer: 118, 2006, pp. 883-888.
Al-Latayfeh, M., et al.,"Antiangiogenic Theraphy for Ischemic Retinopathies," Cold Spring Harbor Perspectives in Medicine, 2012; 2: pp. 1-20.
Maeshima, Y., et al., "Angiogenesis and chronic kidney disease," Fibrogenesis & Tissue Repair 2020, 3:13, pp. 1-17.
Duong, T., et al., "Genetic Ablation of SOX18 Function Supresses Tumor Lymphangiogenesis and Metastasis of Melanoma in Mice," Cancer Research, Jun. 2012, vol. 72, Issue 12, pp. 3105-3114.
Petrovic, I., et al., "VEGF and TNF up-regulate, NSAID down-regulate SOX18 protein level in HUVEC," Central European Journal of Biology, Aug. 2010, vol. 5, Issue 4, pp. 427-434.
Japanese Office Action dated Aug. 31, 2021 for Application No. 2019-534124.
Grimm et al., "The role of SOX family members in solid tumours and metastasis", Seminars in Cancer Biology, 67 (2020) 122-153.

* cited by examiner

A

Natural products

6-Undecylsalicylic acid (Sm1)

6-Tridecylsalicylic acid (Sm2)

Salicylic acid analogues

Sm3

Sm4

Sm5

Sm6

Sm7

Sm8

Sm9

Sm10

Resorcinol analogues

Sm11

Sm12

Sm13

Sm14

NSAID analogues

Salicylic acid

Aspirin

Gentisic acid

Meclofenamic acid

Niflumic acid

Flufenamic acid

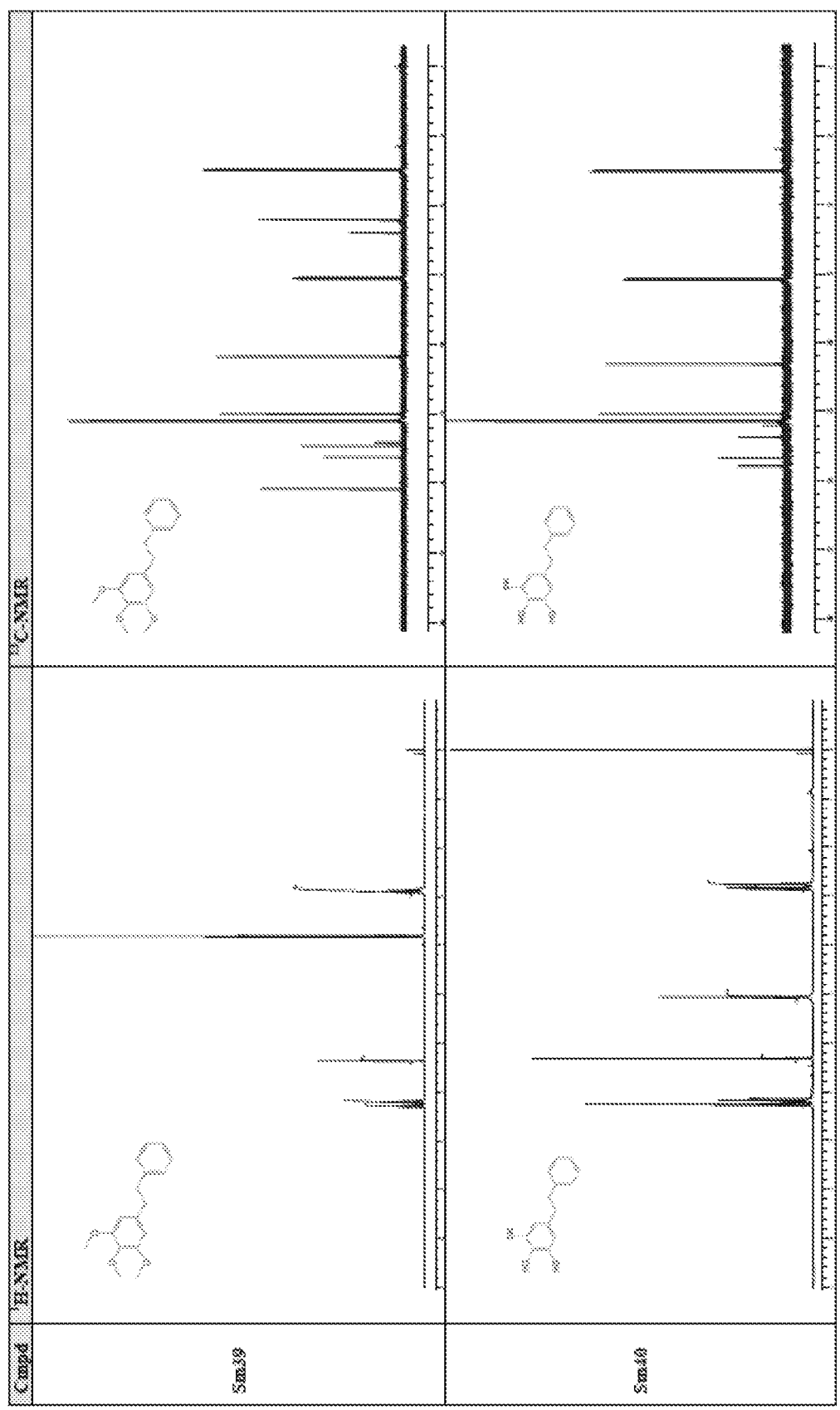

INHIBITORS OF SOX18 PROTEIN ACTIVITY FOR TREATING ANGIOGENESIS-AND/OR LYMPHANGIOGENESIS-RELATED DISEASES

FIELD OF THE INVENTION

The invention relates to the field of medical treatment. More particularly, this invention relates to compounds for use in the inhibition of SOX18 transcription factor activity.

BACKGROUND TO THE INVENTION

Any reference to background art herein is not to be construed as an admission that such art constitutes common general knowledge in Australia or elsewhere.

Direct modulation of transcription factors (TF) by small molecules remains a long-standing quest. Early results were limited to nuclear receptors, which contain a ligand-binding domain targetable by small molecules. These findings have been translated into therapeutic applications in hormone-dependent cancers (Perissi and Rosenfeld, 2005). The current challenge is to reach beyond nuclear receptors to a broader range of transcription factors that lack binding pockets for small molecular drugs. The task is made difficult due to the lack of defined three-dimensional structures for many TFs, especially their protein-protein binding domains, the difficulty to recombinantly express TFs, and the lack of assay technology to investigate their mode of action (Fontaine et al., 2015). Modulation of TF activity are generally achieved by changing their gene expression levels or concentration in the nucleus, or by changing their binding abilities to either DNA or partner proteins, with the latter the more promising strategy to achieve TF selectivity. A few publications on small molecules disrupting TF recruitment of partner proteins are a testament to the potential of this approach (Miyoshi et al., 2011, Vassilev et al., 2004, Filippakopoulos et al., 2010, Vogler et al., 2009, Liu et al., 2014).

Amongst TFs in the human genome, developmental TFs stand out as attractive molecular targets since their expression is often dysregulated under specific pathological conditions in adult, while silenced under physiological conditions (e.g. not required for phenotype maintenance at adulthood) (Boyadjiev and Jabs, 2000, Darnell, 2002, Lopez-Bigas et al., 2006, Vaquerizas et al., 2009). One class of developmental factors, the SOX (SRY-related HMG-box) TFs, have recently emerged as key regulators of stem cell programming as well as molecular switches in cancer related conditions (Sarkar and Hochedlinger, 2013, Niwa et al., 2009). Previous attempts at targeting SOX proteins have mainly focused on SOX2 (Narasimhan et al., 2011), a potential oncogene in various cancers (Bass et al., 2009), and SOX18 (Klaus et al., 2016), a key molecular switch for vascular development (Cermenati et al., 2008, Francois et al., 2008, Pennisi et al., 2000). Dawson polyoxometalates have been shown to inhibit SOX2 DNA-binding, however, only displayed low selectivity against various TF families, and were never tested in any in vitro or in vivo functional assay (Narasimhan et al., 2014, Narasimhan et al., 2011). More recently, SOX DNA decoys have been used as selective inhibitors of SOX18 DNA-binding and SOX18-dependent transactivation. While these decoys display great selectivity over non-SOX TF, they cannot diffuse through cell membranes on their own, limiting their scope of application (Klaus et al., 2016). An unexplored aspect of the pharmacological modulation of SOX TF's is related to how these proteins recruit their partners and consequently modulate transcription via a range of protein-protein interactions (PPIs). Arguably, synthetic libraries do not have the structural diversity required to target PPIs (Hopkins and Groom, 2002, Feher and Schmidt, 2003).

The SOXF group (SOX7, -17 and -18) of transcription factors (TFs) are key regulators of endothelial cell differentiation during development (Francois et al. 2008, Corada et al. 2013, Hosking et al. 2009, Matsui et al. 2006, Cermenati et al. 2008, Herpers et al. 2008), and are thus critical for the formation of vasculature. Mutation or deletion of SoxF genes compromises arteriovenous specification, blood vascular integrity and lymphangiogenesis, and inhibits tumour growth and metastasis in animal models of cancer (Duong et al. 2012, Yang et al. 2013, Zhang et al. 2009, Young et al. 2006). More recently, high levels of SOX18 have been associated with poor prognosis for cancer in human patients (Eom et al. 2012, Pula et al. 2013, Jethon et al. 2015). Pharmacological inhibition of SOX18 protein function therefore presents a potential avenue for management of the vascular response in cancer as well as a potential therapeutic target in vascular cancers.

Accordingly, there remains a need for compounds that inhibit SOX18 protein activity, such as by binding directly thereto, or in proximity to its DNA-binding domain, so as to perturb, for example, SOX18-protein partner recruitment and/or SOX18 DNA binding.

SUMMARY OF INVENTION

The present invention is predicated, at least in part, on the finding that certain compounds of the formula provided herein have efficacy in the inhibition of SOX18 protein activity, and in particular with respect to the ability of SOX18 to bind DNA and/or particular protein partners. By extension, these compounds are further shown to be effective in treating angiogenesis- and/or lymphangiogenesis-related diseases, disorders or conditions, such as cancer metastasis and vascular cancers.

In a first aspect of the invention is provided a compound of formula (I), or a pharmaceutically acceptable salt, solvate or prodrug thereof:

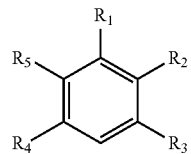

Formula (I)

wherein, $R_1$ is selected from the group consisting of OH and OR wherein Re is $C_1$-$C_4$ alkyl;

$R_2$ is selected from the group consisting of H, $COOR_7$, and $C(O)NR_8R_9$ wherein $R_7$, Re and Re are independently selected from H and $C_1$-$C_4$ alkyl;

$R_3$ is L-A wherein L is a linker selected from $C_2$-$C_8$ alkyl, $C_2$-$C_8$ alkenyl and $C_2$-$C_8$ alkoxyalkyl and A is selected from optionally substituted phenyl and optionally substituted napthyl;

$R_4$ is selected from the group consisting of H, $OR_{10}$, halo and $C_1$-$C_4$ alkyl wherein $R_{10}$ is selected from H and $C_1$-$C_4$ alkyl; and $R_5$ is selected from the group consisting of H, $OR_{11}$, halo and $C_1$-$C_4$ alkyl wherein $R_{11}$ is selected from H and $C_1$-$C_4$ alkyl, wherein, the compound is for use in the inhibition of a SOX18 activity.

In embodiments, $R_1$ is selected from the group consisting of OH and OMe.

Suitably, $R_2$ is selected from the group consisting of H, COOH, COOMe and

Preferably, $R_2$ is selected from COOH and

In embodiments, $R_4$ is selected from the group consisting of H, OH, OMe, Cl and Me.

Suitably, $R_5$ is selected from the group consisting of H, OH and OMe.

In certain embodiments, $R_4$ and $R_5$ are H.

In embodiments, L is a linker selected from $C_2$-$C_6$ alkyl, $C_2$-$C_6$ alkenyl and $C_2$-$C_6$ alkoxyalkyl.

In any of the recited embodiments, $R_3$ is selected from the group consisting of:

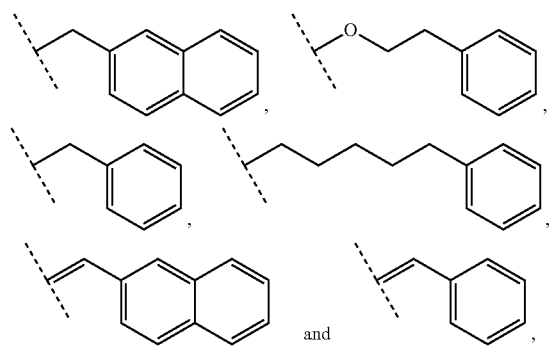

and wherein, the broken line indicates the attachment from that adjacent atom to the ring of formula I and the structures shown include E/Z isomers thereof.

In one embodiment, the compound of the first aspect is selected from the group consisting of:

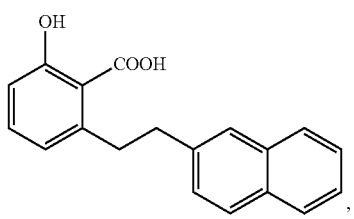

-continued

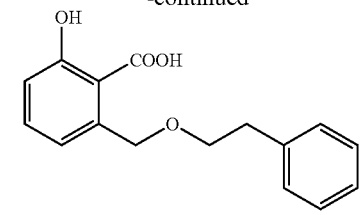

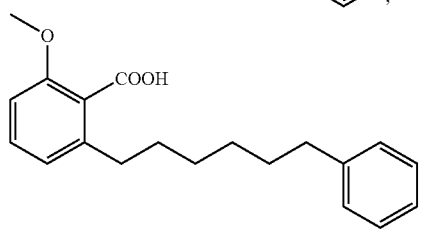

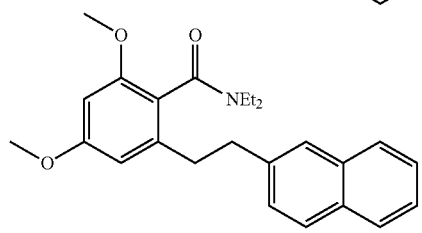

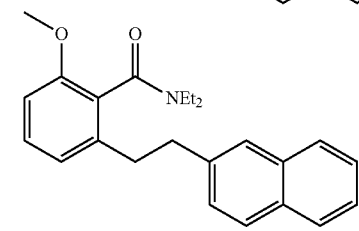

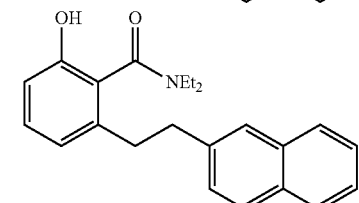

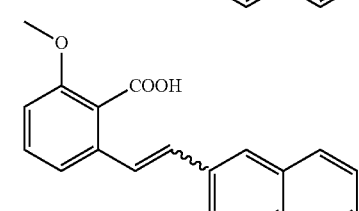

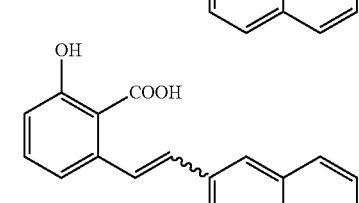

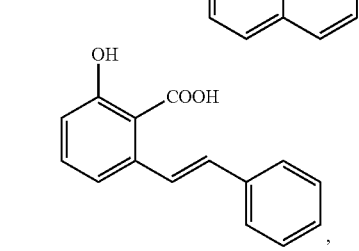

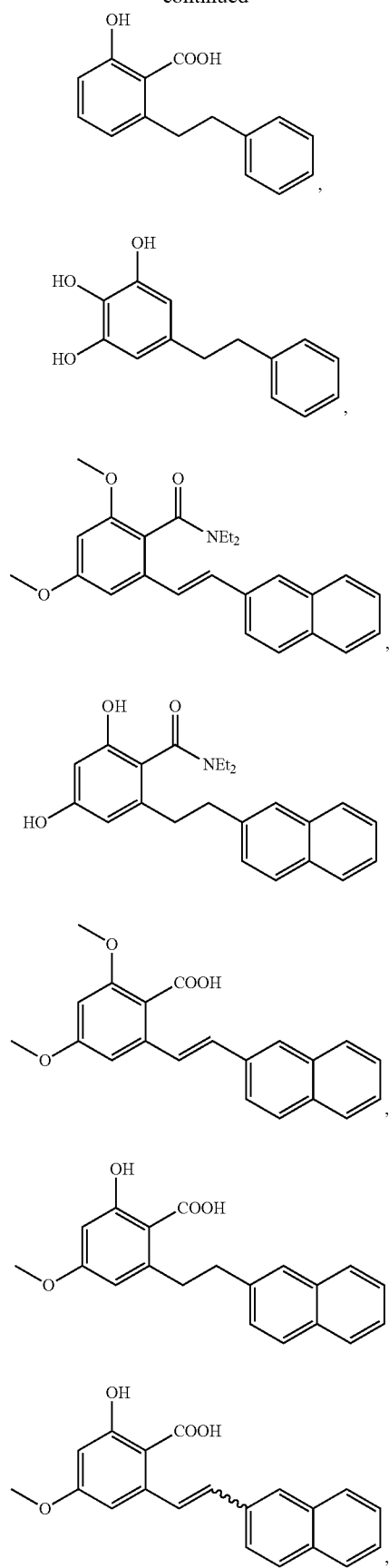
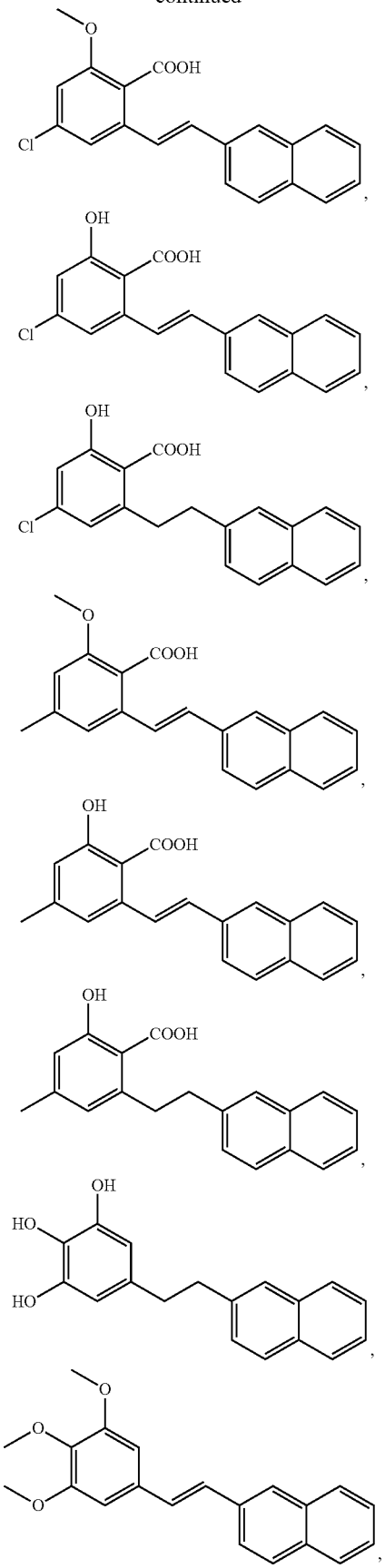

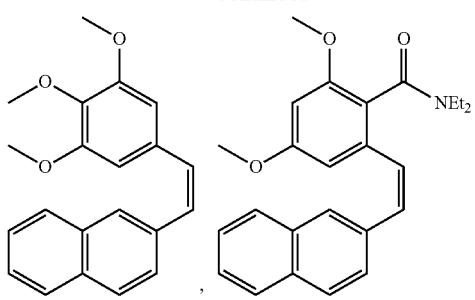
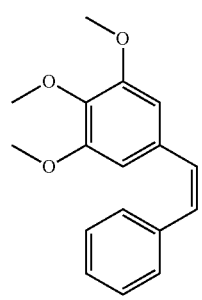
More preferably, the compound of the first aspect is selected from the group consisting of:
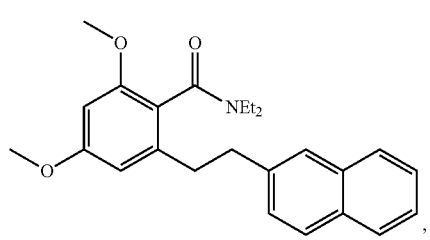
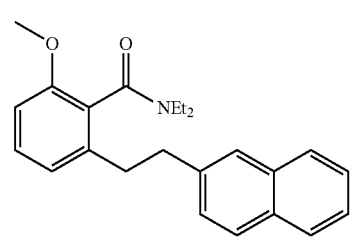
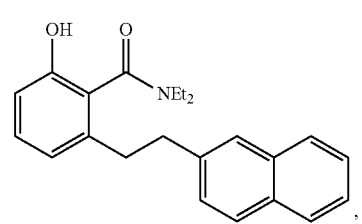
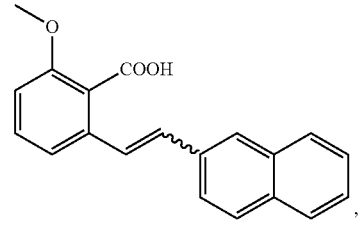
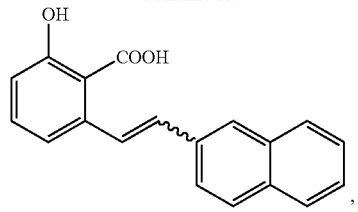
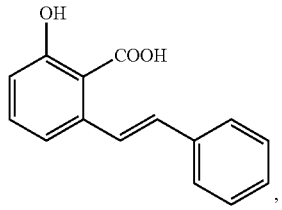
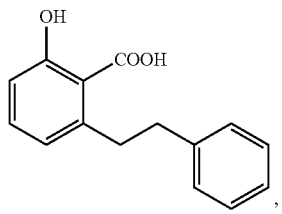
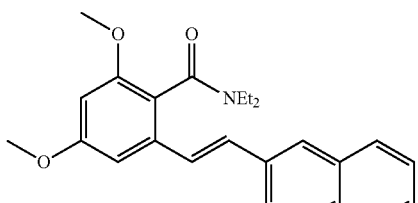
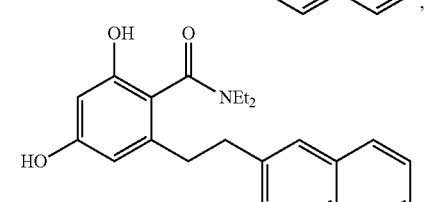
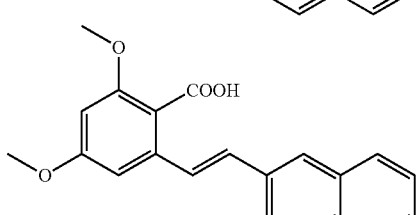
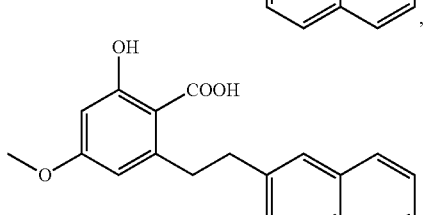
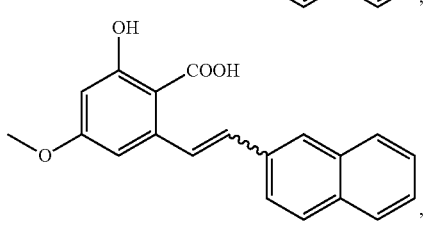

-continued

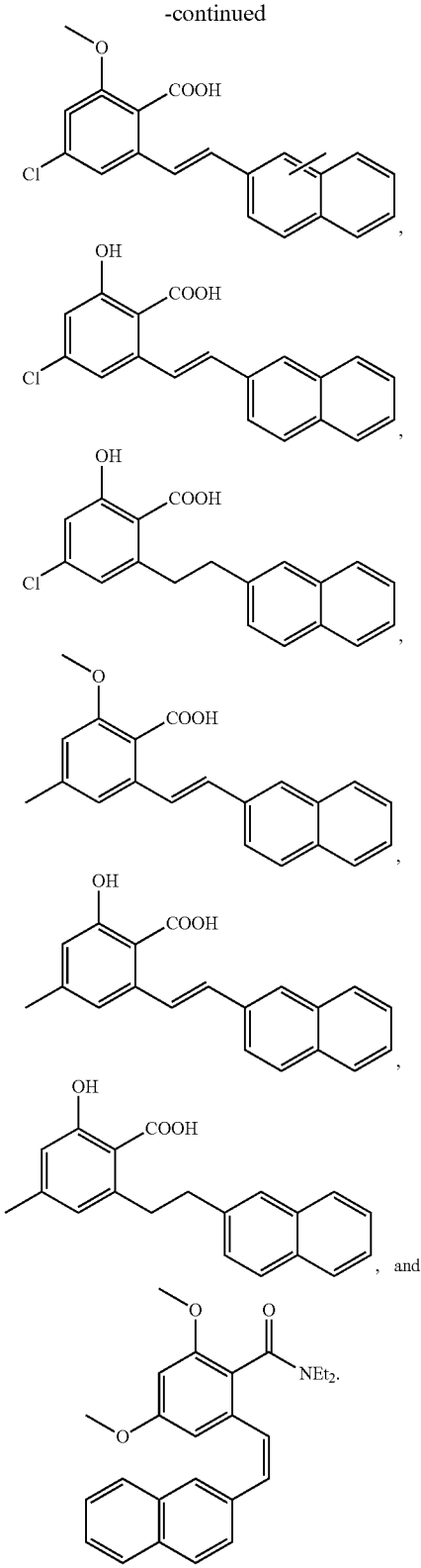

Suitably, with respect to the compound of the present aspect, the SOX18 activity includes contacting and/or binding to a DNA sequence and/or a protein. Preferably, the protein is selected from the list consisting of SOX7, RBPJ, XRCC5, SOX18, ILF3, DDX17 and any combination thereof.

In a second aspect of the invention is provided a pharmaceutical composition comprising a compound of the first aspect, or a pharmaceutically acceptable salt, solvate or prodrug thereof, and a pharmaceutically acceptable carrier, diluent and/or excipient.

In a third aspect of the invention is provided a method of treatment or prevention of an angiogenesis- and/or lymphangiogenesis-related disease, disorder or condition in a subject including the step of administering to the subject an effective amount of the compound of the first aspect, or a pharmaceutically effective salt, solvate or prodrug thereof, or the pharmaceutical composition of the second aspect, to thereby treat or prevent the angiogenesis- and/or lymphangiogenesis-related disease, disorder or condition.

In a fourth aspect of the invention is provided use of the compound of the first aspect, or a pharmaceutically effective salt, solvate or prodrug thereof, in the manufacture of a medicament for the treatment or prevention of an angiogenesis- and/or lymphangiogenesis-related disease, disorder or condition.

In referring to the third and fourth aspects, the angiogenesis- and/or lymphangiogenesis-related disease, disorder or condition suitably is or comprises an ophthalmic disease, disorder or condition. Preferably, the ophthalmic disease, disorder or condition is selected from the group consisting of age-related macular degeneration, diabetic retinopathy, ischemic retinopathy, retinopathy of prematurity, neovascular glaucoma, iritis rubeosis, corneal neovascularization, cyclitis, sickle cell retinopathy, pterygium, vascular response during corneal injury and any combination thereof.

In an alternative embodiment of the invention of the third and fourth aspects, the angiogenesis- and/or lymphangiogenesis-related disease, disorder or condition is or comprises a cancer. Preferably, the cancer is selected from the group consisting of prostate cancer, lung cancer, breast cancer, bladder cancer, renal cancer, colon cancer, gastric cancer, pancreatic cancer, ovarian cancer, melanoma, hepatoma, hepatocellular carcinoma, sarcoma, leukemia, acute T cell lymphoma, vascular neoplasms and any combination thereof. In a particular embodiment, the compound of the first aspect or the pharmaceutical composition of the second aspect prevents and/or inhibits metastasis of said cancer.

In a further embodiment of the two aforementioned aspects, the angiogenesis- and/or lymphangiogenesis-related disease, disorder or condition is or comprises a renal disease, disorder or condition. Preferably, the renal disease, disorder or condition is selected from the group consisting of chronic renal transplant dysfunction, primary renal fibrotic disorders, proteinuria, diabetic nephropathy, renal inflammation and any combination thereof.

In another embodiment of the two aforementioned aspects, the angiogenesis- and/or lymphangiogenesis-related disease, disorder or condition is or comprises atherosclerosis.

In yet another embodiment of the two aforementioned aspects, the angiogenesis- and/or lymphangiogenesis-related disease, disorder or condition is or comprises Hypotrichosis-Lymphedema-Telangiectasia Syndrome.

In a fifth aspect of the invention is provided a method of inhibiting or preventing metastasis of a cancer in a subject including the step of administering to the subject an effective amount of the compound of the first aspect, or a pharmaceutically effective salt, solvate or prodrug thereof, or the pharmaceutical composition of the second aspect, to thereby inhibit or prevent metastasis of the cancer.

Suitably, the cancer is selected from the group consisting of prostate cancer, lung cancer, breast cancer, bladder cancer, renal cancer, colon cancer, gastric cancer, pancreatic cancer, ovarian cancer, melanoma, hepatoma, sarcoma, leukemia, lymphoma, vascular neoplasms (e.g., angioma, angiosarcoma, hemangioma) and any combination thereof.

In a sixth aspect of the invention is provided a method of inhibiting, preventing or reducing a SOX18 activity in a subject comprising the step of administering to the subject an effective amount of the compound of the first aspect, or a pharmaceutically effective salt, solvate or prodrug thereof, or the pharmaceutical composition of the second aspect, to thereby inhibit, prevent or reduce the SOX18 activity in the subject.

Suitably, the SOX18 activity includes contacting and/or binding to a DNA sequence and/or a protein. Preferably, the protein is selected from the list consisting of SOX7, RBPJ, XRCC5, SOX18, ILF3, DDX17 and any combination thereof.

BRIEF DESCRIPTION OF THE DRAWINGS

In order that the invention may be readily understood and put into practical effect, preferred embodiments will now be described by way of example with reference to the accompanying figures wherein.

DETAILED DESCRIPTION

Definitions

Figure 1:
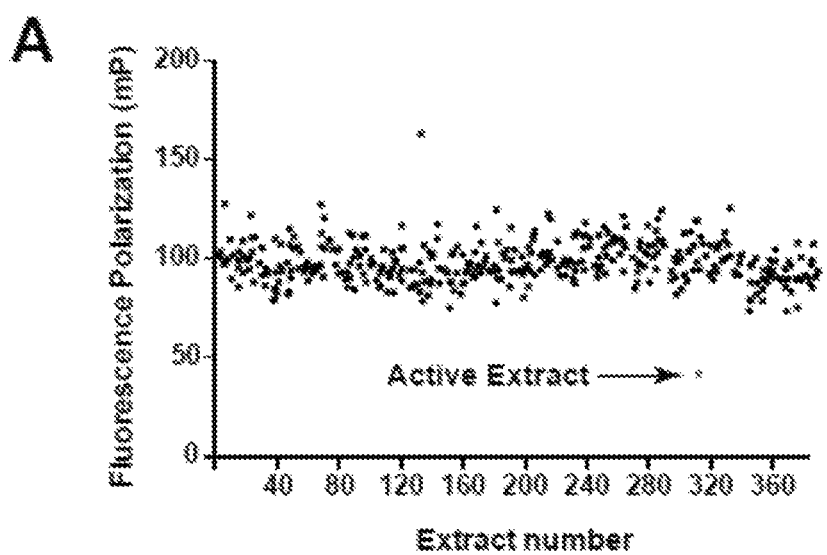
FIG. 1: Natural products, inhibitors of SOX18-DNA binding. A. Representative dataset from high throughput FP screen of 2688 marine extracts at 0.25 mg/mL. The screen was run on full-length mouse SOX18 with FAM-labelled SOX-responsive element (mouse Prox1 intron 1). Competitive binding of a ligand to SOX18 reduces the FP index (arrow pointing to red dot active extract). B. Chemical structure of Sm1 and Sm2. C. FP concentration-response curve of Sm1 and Sm2 (full-length mouse SOX18, mean±S.D. N=3).
Figure 1:
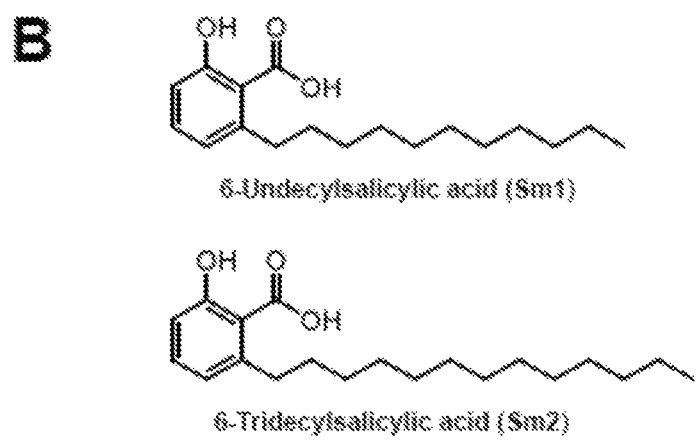
Figure 1:
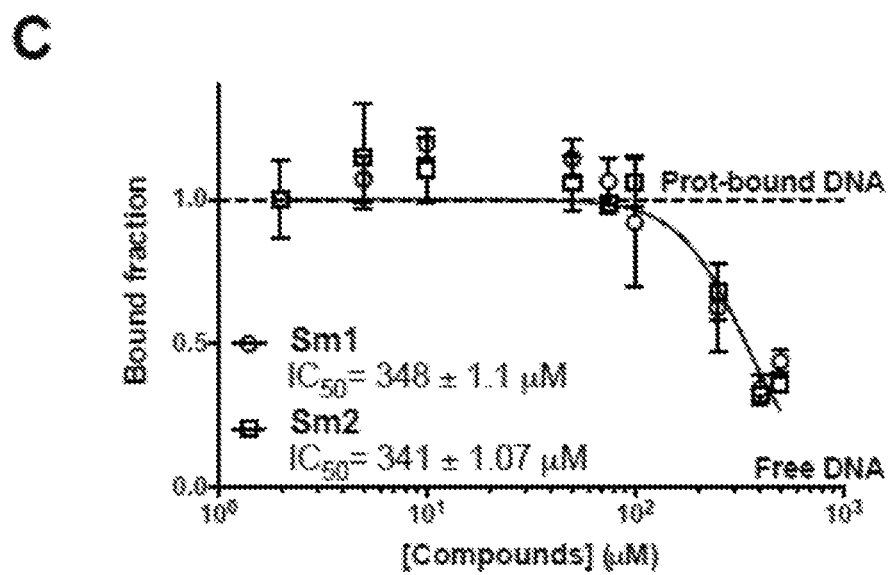

In this patent specification, the terms 'comprises', 'comprising', 'includes', 'including', or similar terms are intended to mean a non-exclusive inclusion, such that a method or composition that comprises a list of elements does not include those elements solely, but may well include other elements not listed.

Unless defined otherwise, all technical and scientific terms used herein have the same meaning as would be commonly understood by those of ordinary skill in the art to which this invention belongs.

The term "alkyl", as used herein, refers to a straight-chain or branched alkyl substituent containing from, for example, 1 to about 8 carbon atoms, preferably 1 to about 7 carbon atoms, more preferably 1 to about 6 carbon atoms, even more preferably from 1 to about 4 carbon atoms. Examples of such substituents may be selected from the group consisting of methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl and the like. The number of carbons referred to relates to the carbon backbone and carbon branching but does not include carbon atoms belonging to any substituents, for example the carbon atoms of an alkyl or alkoxy substituent branching off the main carbon chain.

The term "alkenyl" refers to optionally substituted unsaturated linear or branched hydrocarbon groups, having 2 to 8 carbon atoms, preferably 2 to 7 carbon atoms, more preferably 2 to 6 carbon atoms or 2 to 4 carbon atoms and having at least one carbon-carbon double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. The number of carbons referred to relates to the carbon backbone and carbon branching but does not include carbon atoms belonging to any substituents. Examples of such substituents may be selected from the group consisting of ethenyl, propenyl, isopropenyl, butenyl, s- and t-butenyl, pentenyl, hexenyl, hept-1,3-diene, hex-1,3-diene, non-1,3,5-triene and the like.

The term "alkoxyalkyl" as used herein means straight or branched chain alkyl groups linked by an oxygen atom (i.e., alkyl-O-alkyl otherwise referred to as 'ether' groups), wherein alkyl is as described above. In particular embodiments, alkoxyalkyl refers to oxygen-linked groups comprising 1 to 8 carbon atoms ("C1-8 alkoxyalkyl"). In further embodiments, alkoxyalkyl refers to oxygen-linked groups comprising 2 to 8 carbon atoms ("C2-8 alkoxyalkyl"), 2 to 6 carbon atoms ("C2-6 alkoxyalkyl"), 2 to 4 carbon atoms ("C2-4 alkoxyalkyl") or 2 to 3 carbon atoms ("C2-3 alkoxyalkyl"). The recited number of carbon atoms refers to those in the entire alkoxyalkyl/ether chain.

The term "optionally substituted", as used herein, refers to substituents which may extend from the relevant group, such as a phenyl or napthyl group, and may include such functionalities as halo including F, Cl and Br; $C_1$-$C_4$ alkyl; $OR_{12}$ wherein $R_{12}$ is $C_1$-$C_4$ alkyl; and $NR_{13}R_{14}$ wherein $R_{13}$ and RU are independently selected from H and $C_1$-$C_4$ alkyl.

According to a first aspect of the invention, there is provided a compound of formula (I), or a pharmaceutically acceptable salt, solvate or prodrug thereof:

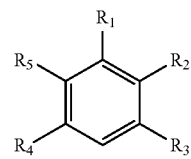

Formula (I)

wherein, $R_1$ is selected from the group consisting of OH and $OR_6$ wherein $R_6$ is $C_1$-$C_4$ alkyl;

$R_2$ is selected from the group consisting of H, $COOR_7$, and $C(O)NR_8R_9$ wherein $R_7$, Re and $R_9$ are independently selected from H and $C_1$-$C_4$ alkyl;

$R_3$ is L-A wherein L is a linker selected from $C_2$-$C_8$ alkyl, $C_2$-$C_8$ alkenyl and $C_2$-$C_8$ alkoxyalkyl and A is selected from optionally substituted phenyl and optionally substituted napthyl;

$R_4$ is selected from the group consisting of H, $OR_{10}$, halo and $C_1$-$C_4$ alkyl wherein $R_{10}$ is selected from H and $C_1$-$C_4$ alkyl; and $R_5$ is selected from the group consisting of H, $OR_{11}$, halo and $C_1$-$C_4$ alkyl wherein $R_{11}$ is selected from H and $C_1$-$C_4$ alkyl, wherein, the compound is for use in the inhibition of a SOX18 activity.

In embodiments, $R_1$ is selected from the group consisting of OH and OMe.

Suitably, $R_2$ is selected from the group consisting of H, COOH, COOMe and

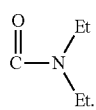

Preferably, R₂ is selected from COOH and

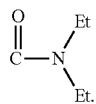

In embodiments, R₄ is selected from the group consisting of H, OH, OMe, Cl and Me.

Suitably, R₅ is selected from the group consisting of H, OH and OMe.

In certain embodiments, R₄ and R₅ are H.

In embodiments, L is a linker selected from $C_2$-$C_6$ alkyl, $C_2$-$C_6$ alkenyl and $C_2$-$C_6$ alkoxyalkyl.

In any of the recited embodiments, R₃ is selected from the group consisting of:

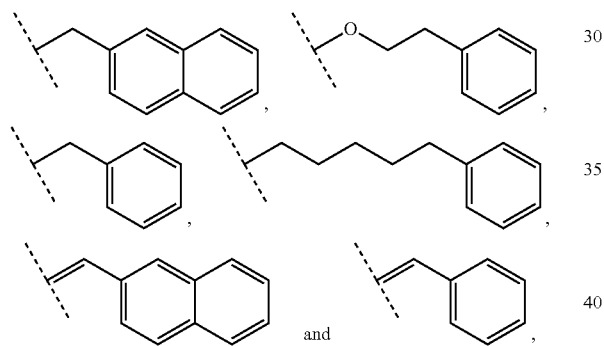

wherein, the broken line indicates the attachment from that adjacent atom to the ring of formula I and the structures shown include E/Z isomers thereof.

In one embodiment, the compound of the first aspect is selected from the group consisting of:

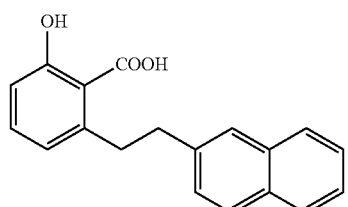

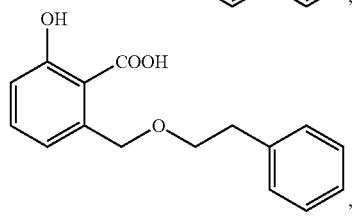

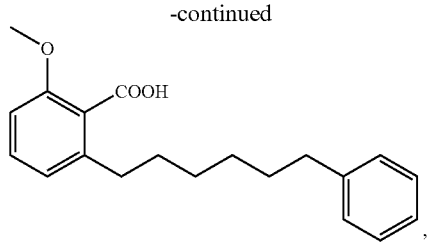

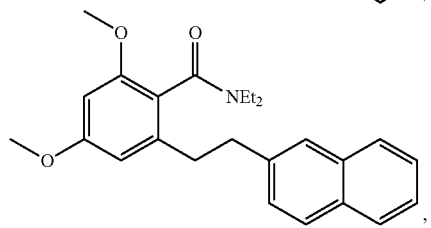

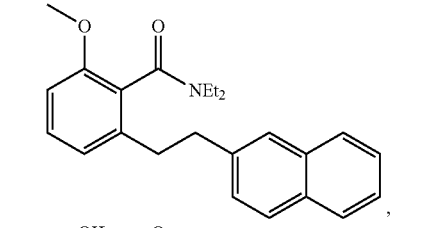

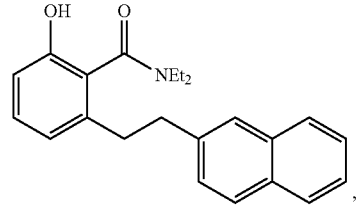

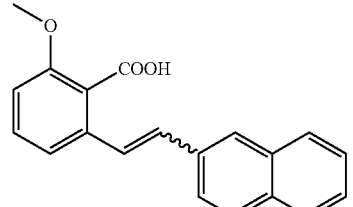

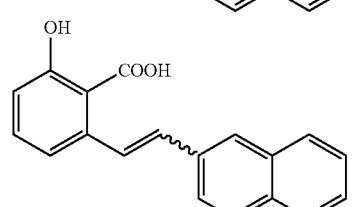

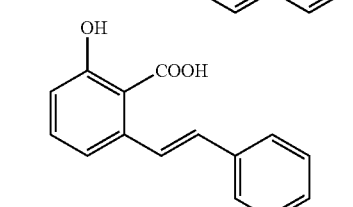

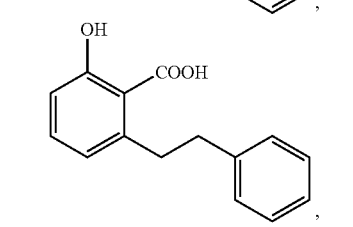

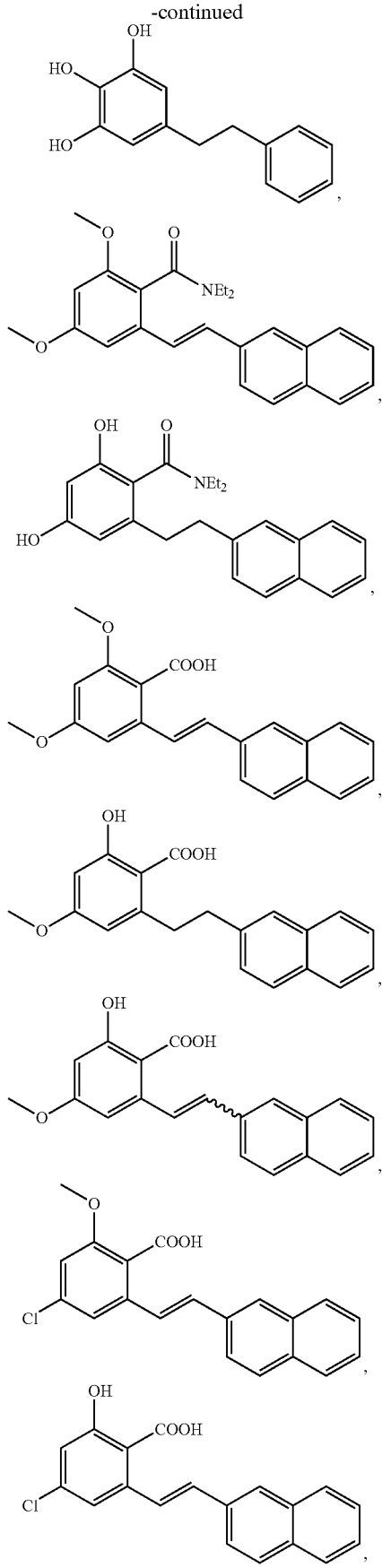
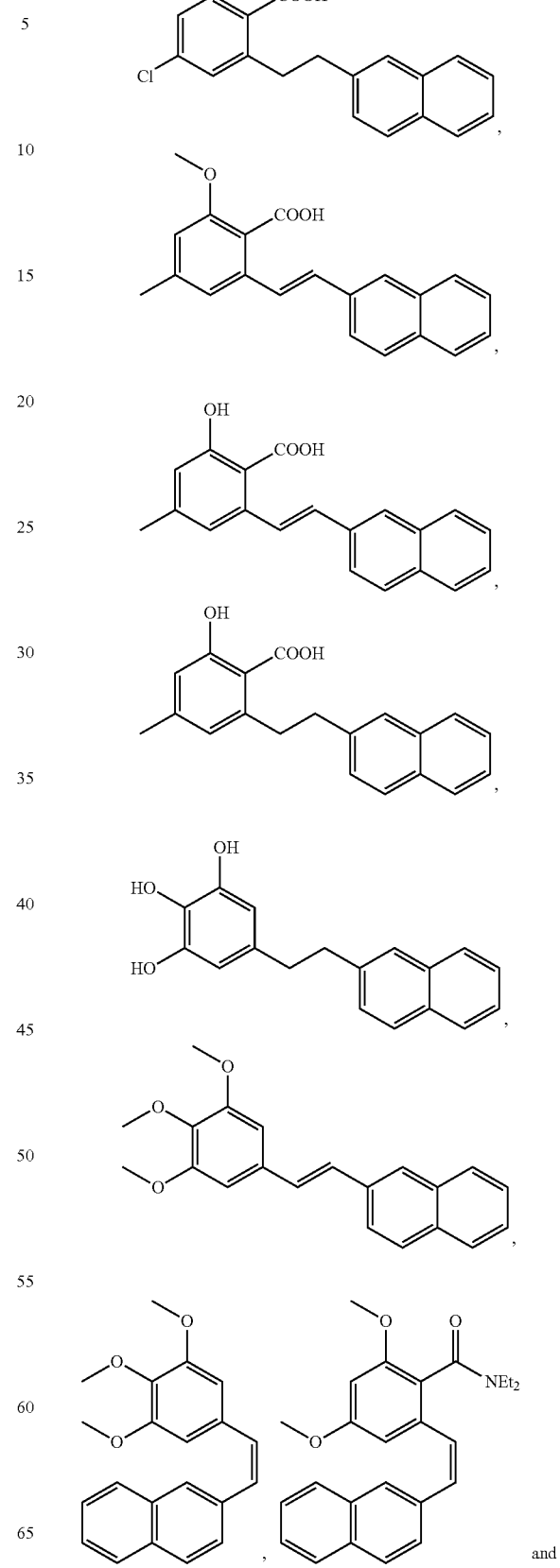

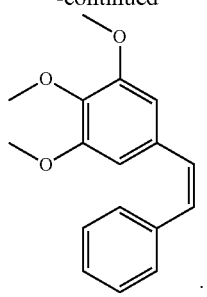
In one preferred embodiment, the compound of the present aspect is selected from the group consisting of:
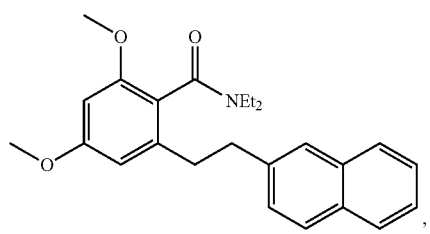,
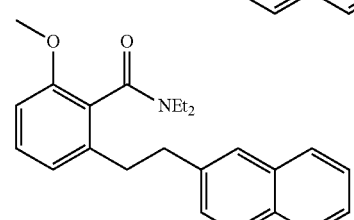,
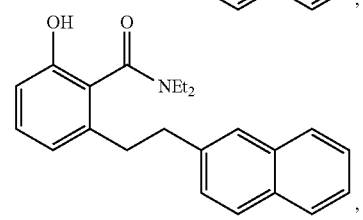,
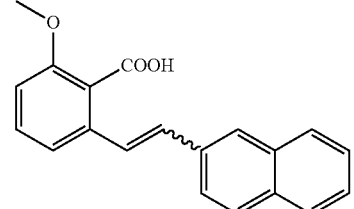,
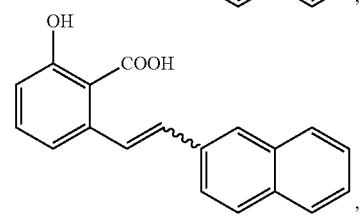,
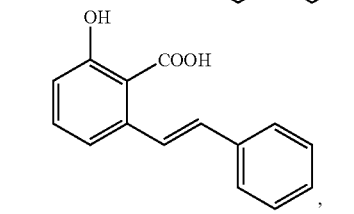,
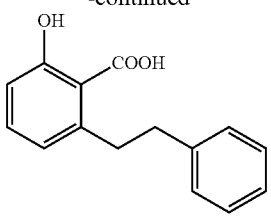
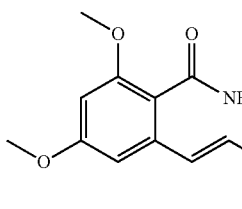,
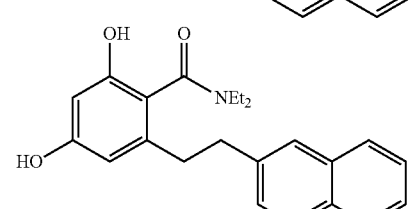,
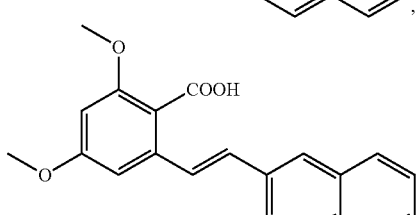,
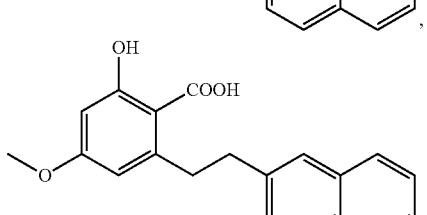,
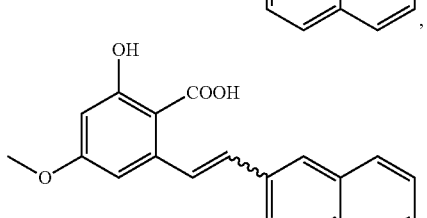,
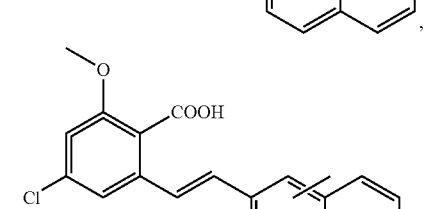,
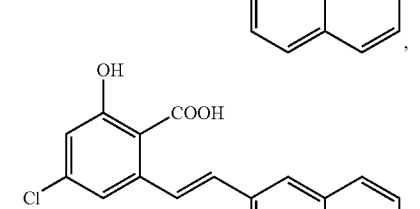,

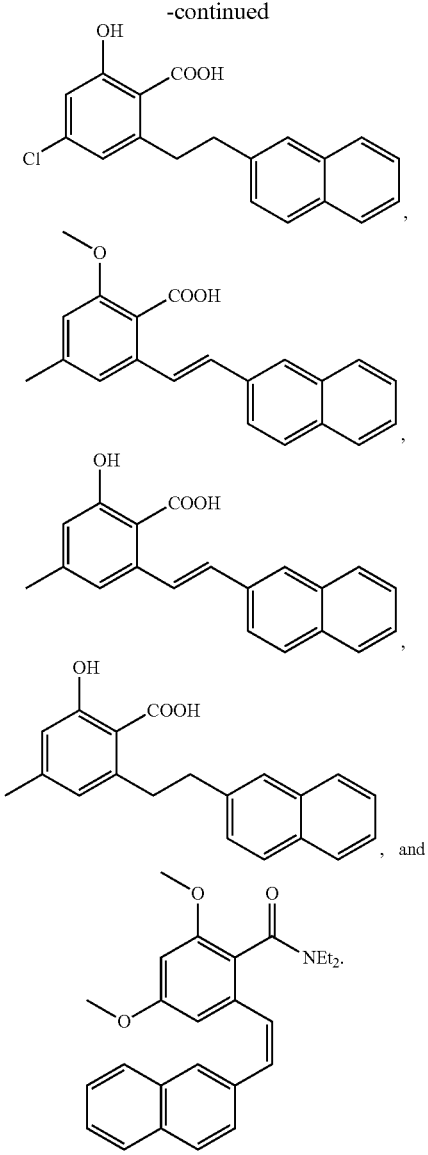

, and

It would be understood by the skilled artisan that SOX18 is a member of the SOX (SRY-related HMG-box) family of transcription factors. These transcription factors are typically involved in the regulation of embryonic development and in the determination of the cell fate. In particular, the SOX18 protein can function as a transcriptional regulator after forming a protein complex with other proteins. It has been shown that SOX18 plays a role in hair, blood vessel, and lymphatic vessel development. Other names for SASH1 may include SRY-box 18, HLTS and HLTRS. Non-limiting examples of Accession Numbers referencing the nucleotide sequence of the SOX18 gene, or its encoded protein, as are well understood in the art, in humans include NG_008095.1, NM_018419.2 and NP_060889.1. As generally used herein, "SOX18" may refer to a SOX18 nucleic acid or encoded protein, unless otherwise specified.

Suitably, the SOX18 activity that is modulated is that of lymphangiogenesis (i.e., the growth of new lymphatic vessels from existing lymphatic vessels), vasculogenesis (i.e., the de novo formation of the embryonic circulatory system) and/or angiogenesis (i.e., the growth of blood vessels from pre-existing vasculature). To this end, in an embodiment of the first aspect, one or more compounds of formula (I) may be useful for treating, decreasing or preventing lymphangiogenesis, angiogenesis and/or vasculogenesis.

Accordingly, one or more compounds of formula (I) suitably have an effect in preventing and/or reducing the severity of the symptoms of an angiogenesis- and/or lymphangiogenesis-related disease, disorder or condition.

In one embodiment, the SOX18 activity includes contacting and/or binding to a DNA sequence and/or a protein. In this regard, the compound of the first aspect may have an effect on one or more of the underlying cellular signalling pathways of the angiogenesis- and/or lymphangiogenesis-related disease, disorder or condition, including, but not limited to, the inhibition of SOX18 DNA binding and/or protein-protein interactions.

With respect to DNA binding, it will be understood that SOX18 is a transcription factor capable of binding to DNA, such as to the consensus sequence 5'-AACAAAG-3' by its HMG box, so as to trans-activate transcription via this binding. Furthermore, the SOX18 protein may act as a transcriptional regulator after forming a protein complex with one or more proteins.

As used herein, a "gene" is a nucleic acid which is a structural, genetic unit of a genome that may include one or more amino acid-encoding nucleotide sequences and one or more non-coding nucleotide sequences inclusive of promoters and other 5' untranslated sequences, introns, polyadenylation sequences and other 3' untranslated sequences, although without limitation thereto. In most cellular organisms, a gene is a nucleic acid that comprises double-stranded DNA.

The term "nucleic acid" as used herein designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylcytosine, methylinosine, methyladenosine and/or thiouridine, although without limitation thereto.

By "protein" is meant an amino acid polymer. As would be appreciated by the skilled person, the term "protein" also includes within its scope phosphorylated forms of a protein (i.e., a phosphoprotein) and/or glycosylated forms of a protein (i.e. a glycoprotein). A "peptide" is a protein having no more than fifty (50) amino acids. A "polypeptide" is a protein having more than fifty (50) amino acids.

Also provided are protein "variants" of SOX18 such as naturally occurring (e.g. allelic variants) and orthologs thereof. Preferably, protein variants share at least 70% or 75%, preferably at least 80% or 85% or more preferably at least 90%, 91%, 92%, 93%, 94%, 95%, 96%, 97%, 98% or 99% sequence identity with an amino acid sequence of SOX18 disclosed herein or known in the art.

As used herein, the term "protein-protein interaction" or "PPI" refers to refers to the close and stable association between two or more proteins. It usually involves the formation of non-covalent chemical bonds, such as hydrogen bonds. PPIs may be binary (two protein binding partners; a dimer) or tertiary (three or more protein binding partners, e.g., a trimer). Proteins within a PPI (i.e., binding partners) may be the same protein (such as a homodimer or homotrimer) or different proteins (such as a heterodimer or hetero trimer). Preferably, the protein interaction is reversible such that dissociation of SOX18 from the protein, or protein subunits, can occur under suitable conditions. Preferably, such forces are weak, e.g. have $K_d$'s in the μM range, such that the compound of the invention can disrupt the interaction between the SOX18 and the protein.

Preferably, the protein is selected from the list consisting of SOX7, RBPJ, XRCC5, SOX18, ILF3, DDX17 and any combination thereof.

In view of the above, it is one advantage of the compounds of the first aspect that, depending on the selection of groups around the core phenyl ring, the clinical effect they display may be somewhat tailored, depending on the choice of groups, towards the inhibition of DNA binding and/or particular protein-protein interactions by SOX18.

In some embodiments, compounds with one or more chiral centers may be provided. While racemic mixtures of compounds of the invention may be active, selective, and bioavailable, isolated isomers may be of interest as well.

The compounds of the present invention also include stereoisomers of the compounds described herein and compositions comprising more than one compound of the invention may, where applicable, include such stereoisomers, for example E/Z isomers, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention. Isomers may include geometric isomers. Examples of geometric isomers include, but are not limited to, trans isomers or cis isomers (E/Z) across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein and other similar tests which are well known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemic, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound of the first aspect may optionally be provided in a composition that is enantiomerically or diastereomerically enriched, such as a mixture of enantiomers or diastereomers in which one enantiomer or diastereomer is present in excess, in particular, to the extent of 95% or more, 96% or more, 97% or more, 98% or more, or 99% or more, including 100%.

The compounds of the first aspect may be utilized per se or in the form of a pharmaceutically acceptable ester, amide, salt, solvate, prodrug, or isomer, as appropriate. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound or prodrug useful according to the present invention may be prepared in a similar manner using a pharmaceutically acceptable base, such as sodium hydroxide, potassium hydroxide, ammonium hydroxide, calcium hydroxide, triethylamine, or the like.

Esters of the compounds according to the present invention may be prepared through functionalization of hydroxyl and/or carboxyl groups that may be present within the compound. Amides and prodrugs may also be prepared using techniques known to those skilled in the art. For example, amides may be prepared from esters, using suitable amine reactants, or they may be prepared from an anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C.

Examples of pharmaceutically acceptable solvates include, but are not limited to, compounds according to the invention in combination with water, isopropanol, ethanol, methanol, DMSO, ethyl acetate, acetic acid, or ethanolamine.

According to a second aspect of the invention there is provided a pharmaceutical composition comprising a compound of the first aspect, or a pharmaceutically acceptable salt, solvate or prodrug thereof, and a pharmaceutically acceptable carrier, diluent and/or excipient.

Suitably, the pharmaceutically acceptable carrier, diluent and/or excipient may be or include one or more of diluents, solvents, pH buffers, binders, fillers, emulsifiers, disintegrants, polymers, lubricants, oils, fats, waxes, coatings, viscosity-modifying agents, glidants and the like.

The salt forms of the compounds of the invention may be especially useful due to improved solubility.

Diluents may include one or more of microcrystalline cellulose, lactose, mannitol, calcium phosphate, calcium sulfate, kaolin, dry starch, powdered sugar, and the like. Binders may include one or more of povidone, starch, stearic acid, gums, hydroxypropylmethyl cellulose and the like. Disintegrants may include one or more of starch, croscarmellose sodium, crospovidone, sodium starch glycolate and the like. Solvents may include one or more of ethanol, methanol, isopropanol, chloroform, acetone, methylethyl ketone, methylene chloride, water and the like. Lubricants may include one or more of magnesium stearate, zinc stearate, calcium stearate, stearic acid, sodium stearyl fumarate, hydrogenated vegetable oil, glyceryl behenate and the like. A glidant may be one or more of colloidal silicon dioxide, talc or cornstarch and the like. Buffers may include phosphate buffers, borate buffers and carbonate buffers, although without limitation thereto. Fillers may include one or more gels inclusive of gelatin, starch and synthetic polymer gels, although without limitation thereto. Coatings may comprise one or more of film formers, solvents, plasticizers and the like. Suitable film formers may be one or more of hydroxypropyl methyl cellulose, methyl hydroxyethyl cellulose, ethyl cellulose, hydroxypropyl cellulose, povidone, sodium carboxymethyl cellulose, polyethylene glycol, acrylates and the like. Suitable solvents may be one or more of water, ethanol, methanol, isopropanol, chloroform, acetone, methylethyl ketone, methylene chloride and the like. Plasticizers may be one or more of propylene glycol, castor oil, glycerin, polyethylene glycol, polysorbates, and the like.

Reference is made to the Handbook of Excipients $6^{th}$ Edition, Eds. Rowe, Sheskey & Quinn (Pharmaceutical Press), which provides non-limiting examples of excipients which may be useful according to the invention.

It will be appreciated that the choice of pharmaceutically acceptable carriers, diluents and/or excipients will, at least in part, be dependent upon the mode of administration of the formulation. By way of example only, the composition may be in the form of a tablet, capsule, caplet, powder, an injectable liquid, a suppository, a slow release formulation, an osmotic pump formulation or any other form that is effective and safe for administration.

Suitably, the pharmaceutical composition is for the treatment or prevention of a disease, disorder or condition in a mammal as described below. Preferably, the pharmaceutical composition is for the treatment or prevention of an angiogenesis- and/or lymphangiogenesis-related disease, disorder or condition in a mammal.

A third aspect of the invention resides in a method of treatment or prevention of an angiogenesis- and/or lymphangiogenesis-related disease, disorder or condition including the step of administering an effective amount of a compound of the first aspect, or a pharmaceutically effective salt, solvate or prodrug thereof, or the pharmaceutical composition of the second aspect, to thereby treat or prevent the angiogenesis- and/or lymphangiogenesis-related disease, disorder or condition.

A fourth aspect of the invention provides for use of a compound of the first aspect, or a pharmaceutically effective salt, solvate or prodrug thereof, in the manufacture of a medicament for the treatment or prevention of a disease, disorder or condition, such as an angiogenesis- and/or lymphangiogenesis-related disease, disorder or condition.

As generally used herein, the terms "administering" or "administration", and the like, describe the introduction of the compound or composition to a mammal such as by a particular route or vehicle. Routes of administration may include topical, parenteral and enteral which include oral, buccal, sub-lingual, nasal, anal, gastrointestinal, subcutaneous, intramuscular and intradermal routes of administration, although without limitation thereto.

As used herein, "treating" (or "treat" or "treatment") refers to a therapeutic intervention that ameliorates a sign or symptom of the angiogenesis- and/or lymphangiogenesis-related disease, disorder or condition after it has begun to develop. The term "ameliorating", with reference to the angiogenesis- and/or lymphangiogenesis-related disease, disorder or condition, refers to any observable beneficial effect of the treatment. Treatment need not be absolute to be beneficial to the subject. The beneficial effect can be determined using any methods or standards known to the ordinarily skilled artisan.

As used herein, "preventing" (or "prevent" or "prevention") refers to a course of action (such as administering a therapeutically effective amount of one or more of the compounds described herein) initiated prior to the onset of a symptom, aspect, or characteristic of the angiogenesis- and/or lymphangiogenesis-related disease, disorder or condition so as to prevent or reduce the symptom, aspect, or characteristic. It is to be understood that such preventing need not be absolute to be beneficial to a subject. A "prophylactic" treatment is a treatment administered to a subject who does not exhibit signs of an angiogenesis- and/or lymphangiogenesis-related disease, disorder or condition or exhibits only early signs for the purpose of decreasing the risk of developing a symptom, aspect, or characteristic of the angiogenesis- and/or lymphangiogenesis-related disease, disorder or condition.

As used herein, "effective amount" refers to the administration of an amount of the relevant compound or composition sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight etc. An appropriate dosage or dosage regime can be ascertained through routine trial.

As used herein, the terms "subject" or "individual" or "patient" may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment for an angiogenesis- and/or lymphangiogenesis-related disease, disorder or condition, as described herein. However, it will be understood that the aforementioned terms do not imply that symptoms are necessarily present.

The term "angiogenesis-related disease, disorder or condition" as used herein denotes any disorder associated with abnormal blood vessel growth, including excessive blood vessel growth. It will be understood that the control of angiogenesis is altered in certain diseases, disorders or conditions. Many such diseases involve pathological angiogenesis (i.e., inappropriate, excessive or undesired blood vessel formation), which supports the disease state and, in many instances, contributes to the cellular and tissue damage associated with such diseases. Angiogenesis-related diseases, disorder or conditions (i.e., those involving pathological angiogenesis) can be many and varied, and may include, for example, various types of cancers, chronic inflammatory diseases, and neovascularization diseases. Examples of chronic inflammatory diseases, disorders or conditions include, but are not limited to, inflammatory bowel disease, such as Crohn's disease and ulcerative colitis, rheumatoid arthritis, lupus, psoriasis, atherosclerosis and diabetes mellitus.

As generally used herein, the term "lymphangiogenesis-related disease, disorder or condition" refers to any disorder associated with abnormal lymphatic vessel growth, including excessive lymphatic vessel growth. Lymphangiogenesis is ultimately controlled by a complex network of growth factors, cytokines and chemokines and can occur under a number of pathological conditions (see, e.g., El-Chemaly, Ann N Y Acad Sci (2008); Patel, Seminars Ophtalmol (2009); El-Chemaly, Lymphatic Res Biol (2009); Pepper, Clin Cancer Res (2001)), including, but not limited to cancer growth and metastasis, inflammation and transplant rejection. With respect to metastasis, cancer cells may metastasize to lymph nodes and distal organs through lymphatic vessels and this often represents the first step in cancer cell spread beyond the primary cancer.

In one embodiment of the third and fourth aspects, the angiogenesis- and/or lymphangiogenesis-related disease, disorder or condition is or comprises an ophthalmic disease, disorder or condition, and in particular those involving neovascularization. To this end, angiogenesis and/or lymphangiogenesis can play a pivotal role in the development of ophthalmic diseases, disorders or conditions, such as age-related macular degeneration, diabetic retinopathy, ischemic retinopathy, retinopathy of prematurity, neovascular glaucoma, iritis rubeosis, corneal neovascularization, cyclitis, sickle cell retinopathy, the vascular response during corneal injury and pterygium. As these ophthalmic diseases, disorders or conditions progress, the blood vessels of the eye may not only proliferate excessively, but the new vessels can also be weak, leaky and prone to hemorrhage. To this end, the new abnormal vessels may bleed and cause subsequent blindness in the subject.

In one embodiment of the third and fourth aspects, the angiogenesis- and/or lymphangiogenesis-related disease, disorder or condition is or comprises a cancer. To this end, the formation and metastasis of a cancer typically involves pathological angiogenesis. Similar to healthy tissues, cancers require new blood vessel formation in order to provide nutrients and oxygen and remove cellular wastes. Thus, pathological angiogenesis is critical to the growth and expansion of a cancer.

As generally used herein, the terms "cancer", "tumour", "malignant" and "malignancy" refer to diseases or conditions, or to cells or tissues associated with the diseases or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumour markers, loss of tumour suppressor expression or activity and/or aberrant or abnormal cell surface marker expression.

Cancer may include any aggressive or potentially aggressive cancers, tumours or other malignancies such as listed in the NCI Cancer Index at http://www.cancer.gov/cancertopics/alphalist, including all major cancer forms such as sarcomas, carcinomas, lymphomas, leukaemias and blastomas, although without limitation thereto. These may include breast cancer, lung cancer inclusive of lung adenocarcinoma, cancers of the reproductive system inclusive of ovarian cancer, cervical cancer, uterine cancer and prostate cancer, cancers of the brain and nervous system, head and neck cancers, gastrointestinal cancers inclusive of colon cancer, colorectal cancer and gastric cancer, liver cancer, kidney cancer, skin cancers such as melanoma and skin carcinomas, blood cell cancers inclusive of lymphoid cancers and myelomonocytic cancers, cancers of the endocrine system such as pancreatic cancer and pituitary cancers, musculoskeletal cancers inclusive of bone and soft tissue cancers, vascular cancers or neoplasms, such as hemangioma, angioma and angiosarcoma, although without limitation thereto.

In particular embodiments, the cancer is selected from the group consisting of prostate cancer, lung cancer, breast cancer, bladder cancer, renal cancer, colon cancer, gastric cancer, pancreatic cancer, ovarian cancer, melanoma, hepatoma, hepatocellular carcinoma, sarcoma, leukemia, lymphoma, vascular neoplasms, such as hemangioma, angioma and angiosarcoma and any combination thereof.

In one particular embodiment, the compound of the first aspect or the pharmaceutical composition of the second aspect prevents and/or inhibits metastasis of said cancer.

As used herein, "metastasis" or "metastatic", refers to the migration or transfer of malignant cancer cells, or neoplasms, via the circulatory or lymphatic systems or via natural body cavities, typically from the primary focus of tumour, cancer or a neoplasia to a distant site in the body, and the subsequent development of one or more secondary tumours or colonies thereof in the one or more new locations. "Metastases" refers to the secondary tumours or colonies formed as a result of metastasis and encompasses micro-metastases as well as regional and distant metastases.

It will be appreciated that pathological angiogenesis and lymphangiogenesis may play an important role in cancer metastasis. To this end, the formation of blood vessels in a primary cancer not only allows cancer cells to enter the blood stream and to circulate throughout the body, but also supports the formation and growth of metastatic cancers seeded by cancer cells that have metastasized from the primary site.

In a further embodiment of the two aforementioned aspects, the angiogenesis- and/or lymphangiogenesis-related disease, disorder or condition is or comprises a renal disease, disorder or condition. Preferably, the renal disease, disorder or condition is selected from the group consisting of chronic renal transplant dysfunction, primary renal fibrotic disorders, proteinuria, diabetic nephropathy, renal inflammation and any combination thereof.

In one particular embodiment of the third and fourth aspects, the angiogenesis- and/or lymphangiogenesis-related disease, disorder or condition is or comprises atherosclerosis. To this end, it would be appreciated by the skilled artisan that the pathological changes in atherosclerosis can at least in part be attributed to chronic inflammation and neovascularisation. Furthermore, a link has been demonstrated between NF-kB-dependent atherogenic inflammatory response, and SOX18 regulation, suggesting that SOX18 may play a role in the development of atherosclerosis (Garcia-Ramirez et al., 2005). Sox18 has also been shown to be overexpressed in atherosclerotic plaques, and hence could be a major component of the disease aetiology (Brown et al., 2014).

In one embodiment of the third and fourth aspects, the angiogenesis- and/or lymphangiogenesis-related disease, disorder or condition is or comprises Hypotrichosis-Lymphedema-Telangiectasia Syndrome. In this regard, it would be appreciated that Hypotrichosis-Lymphedema-Telangiectasia Syndrome is associated with mutations in the SOX18 gene.

In a fifth aspect, the invention provides a method of preventing or inhibiting metastasis of a cancer in a subject including the step of administering to the subject an effective amount of the compound of the first aspect, or a pharmaceutically effective salt, solvate or prodrug thereof, or the pharmaceutical composition of the second aspect, to thereby inhibit or prevent metastasis of the cancer.

Suitably, the cancer is that hereinbefore described.

A sixth aspect of the invention resides in a method of inhibiting, preventing or reducing a SOX18 activity in a subject comprising the step of administering an effective amount of a compound of the first aspect, or a pharmaceutically effective salt, solvate or prodrug thereof, or the pharmaceutical composition of the second aspect, to thereby inhibit, prevent or reduce the SOX18 activity in the subject.

Suitably, the SOX18 activity includes contacting and/or binding to a DNA sequence and/or a protein. Preferably, the protein is selected from the list consisting of SOX7, RBPJ, XRCC5, SOX18, ILF3, DDX17 and any combination thereof.

The various features and embodiments of the present invention, referred to in individual sections above apply, as appropriate, to other sections, mutatis mutandis. Consequently features specified in one section may be combined with features specified in other sections as appropriate.

The following experimental section describes in more detail the characterisation of certain of the compounds of the invention and their efficacy. The intention is to illustrate certain specific embodiments of the compounds of the invention and their efficacy without limiting the invention in any way.

Example 1

Materials and Methods
Compounds Preparation

Marine extract library. A library of n-butanol fractions generated from a marine library collected across Australia and Antarctica was used for screening. Active fractions were fractionated into pure compounds re-assayed in the same way as original fractions.

A library of 2688 samples of marine invertebrate and alga collected across southern Australia and Antarctica was processed to generate an extract library suitable for high throughput bioassay. EtOH extracts were decanted, concentrated, and partitioned into n-BuOH and H2O phases, then transferred to deep 96-well plates, resulting in a >10-fold concentration of small molecules, while removing salts. The n-BuOH fraction (25 mg/mL w/v of dried residue) was used for screening, following 10- and 100-fold dilution (2.5 and 0.25 mg/mL). Active fractions were triturated with hexane, CH2Cl2 and MeOH, and fractionated into pure compounds by HPLC. All compounds were assayed in the same way as fractions.

Sm1 (6-undecyl salicylic acid) and Sm2 (6-tridecyl salicylic acid) were purified from the original aqueous EtOH extract of brown alga sample, Caulocystis cephalornithos (CMB-01671). The aqueous EtOH extract of sample of brown alga, Caulocystis cephalornithos (CMB-01671), was concentrated in vacuo (4.8 g) and partitioned into n-BuOH (0.80 g) and H2O (4.0 g) soluble materials. An aliquot (40 mg) of the n-BuOH soluble partition was subjected to HPLC fractionation (Agilent Zorbax SB C18 5 µm, 250×9.4 mm column, 4 m/min gradient elution from 60% MeOH/H2O to 100% MeOH over 10 min, followed with 100% MeOH for 10 min, with isocratic 0.01% TFA modifier) to yield 6-undecyl salicylic acid (Sm1, 5.9 mg, RT 12.8 min) and 6-tridecyl salicylic acid (Sm2, 11 mg, RT 13.7 min).

Sm4-Sm14-Focused library. The synthetic analogues were purchased from EndoTherm GmbH (Germany) and Princeton BioMolecular Research (USA), and analyzed for purity by HP-LC/MS.

Sm15-Sm44 SAR library. The SAR library was designed to investigate the role of the lipophilic tail and possible substituents of the salicylic acid scaffold. The six-step synthesis outlined below started from a substituted benzoic acid using a Wittig olefination reaction to introduce the lipophilic tail. Partially protected intermediates were also included in the SAR library. All compounds were purified by HPLC (purity >90%, UV/ELSD/MS).

General Materials and Methods. Reagents and anhydrous solvents (THF, dichloromethane, and acetonitrile) were used as received. Reaction progress was monitored by TLC using Merck silica gel 60 F-254 with UV detection. Silica gel 60 (Merck 40-63 μm) was used for column chromatography. The following stain solutions have been used in addition to UV light with fluorescent TLC plates: phosphomolybdic acid, anisaldehyde/EtOH. Reactions requiring anhydrous conditions were performed under nitrogen. NMR data were collected and calibrated in d4-MeOH or CDCl3 at 298K on a Varian Unity 400 MHz or Bruker Avance 600 MHz spectrometers. HPLC and routine mass spectra were acquired on an Agilent Technologies 1200 Series instrument, fitted with a G1316A UV-Vis detector, 1200 Series ELSD and 6110 quadrupole ESI-MS. High resolution mass spectrometry (HRMS) was performed on the Bruker MicroTOF mass spectrometer.

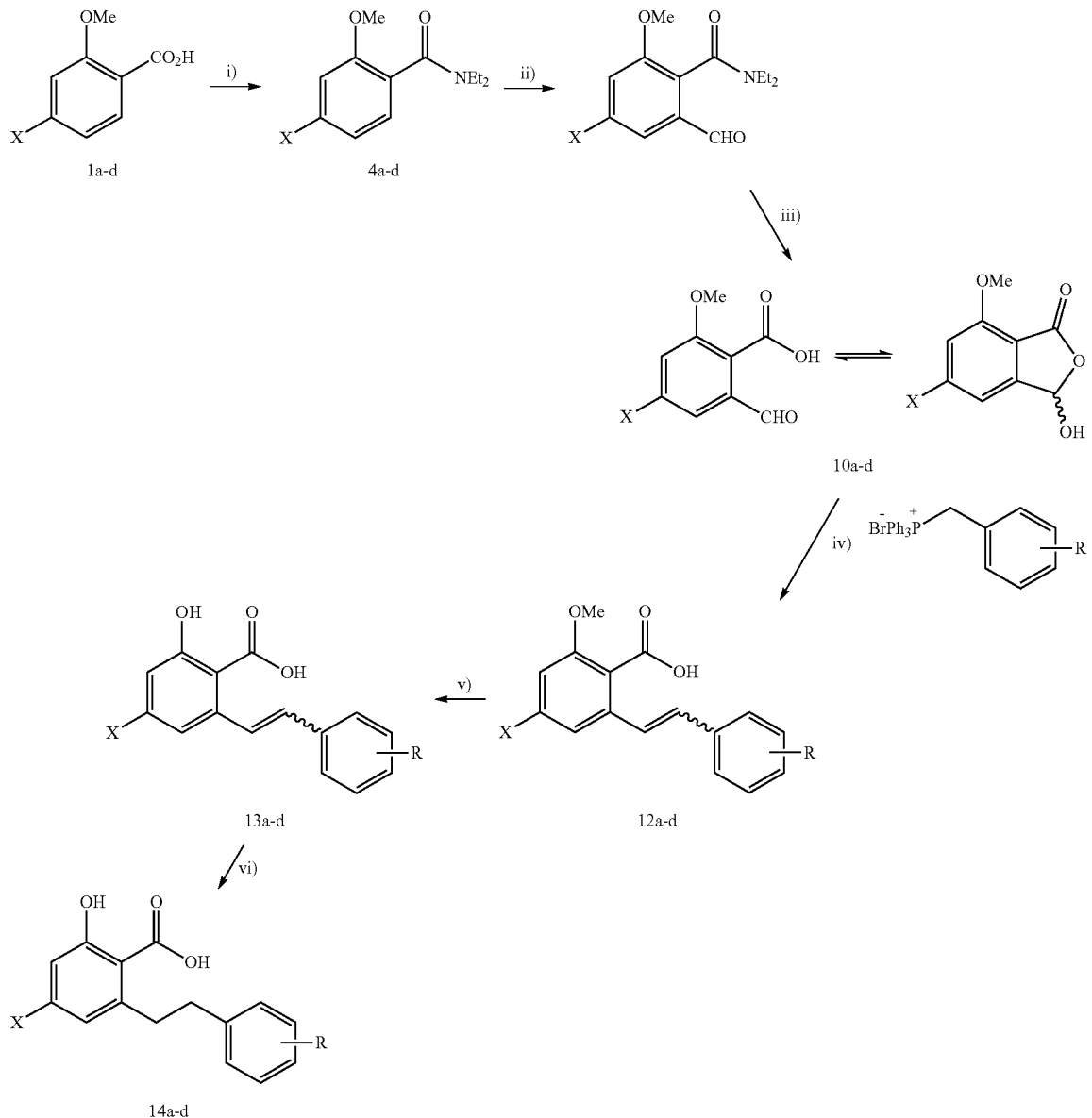

X = H, OCH3, CH3, NO2
i) SOCl2, reflux, 3 h, Et2NH, CH2Cl2, 0° C.-RT, 12 h. ii) sBuLi/TMEDA, -78° C. DMF; iii) AcOH/HCl; iv) NaH, THF, 50° C. 2 h; v) BBr3, CH2Cl2; or 48% aq HBr, reflux 5 h; vi) Pd/C, H2 atm, RT, 1 h.

General procedure for preparation of N,N-diethylbenzamides (4a-d)1. The substituted N,N-diethyl benzamides were prepared from the respective substituted benzoic acids. The acid (5 g, 32.9 mmol) was refluxed with excess thionyl chloride (50 mL) until the evolution of hydrogen chloride was ceased. The excess thionyl chloride was removed under reduced pressure and co-distilled with toluene (3×15 mL). The acid chloride was dissolved in dry $CH_2Cl_2$ (100 mL) and added drop wise diethylamine (13.6 mL, 131.5 mmol) at 0° C. and stirred at room temperature for overnight. The reaction mixture was diluted with $CH_2Cl_2$ (100 mL), washed with water (50 mL), brine solution and dried over anhydrous $MgSO_4$. The organic layer was removed on rotavapor to give the crude compound. The crude compound was purified by flash column chromatography to obtain the pure diethylbenzamide.

General procedure for directed ortho-metalation reaction (5a-d)2. To a solution of TMEDA (0.55 mL, 3.7 mmol) in dry THF (10 mL) was added s-BuLi (2.6 mL, 3.7 mmol, 1.5 M in cyclohexane) at −78° C. and stirred for 15 min., followed by 1-methoxy-N,N-diethylbenzamide (0.35 g, 1.7 mmol) in THF (5 mL). After stirring at the same temperature for 2 h, anhydrous DMF (0.52 mL, 6.8 mmol) was added slowly. The reaction mixture was gradually warmed up to room temperature and stirred for 30 min. The reaction was quenched by addition of 6N aq. HCl solution (10 mL), and extracted with ethyl acetate (3×15 mL). The combined organic layers were washed with brine (10 mL), and dried over MgSO4. After removal of the solvent under vacuum, the residue was purified by a flash column chromatography (n-hexane/ethyl acetate, ½) to give the product.

General procedure for cleaving N,N-diethylbenzamide (10a-d)3N,N-diethylbenzamide (1.3 mmol) was dissolved in glacial AcOH (3 mL), added 10% aq. HCl (3 mL), and the mixture was refluxed for 12 h. After cooling to room temperature, the acetic acid was removed under reduced pressure, diluted with H2O and extracted with EtOAc (30 mL). The organic layer was washed with brine, separated and dried over anhydrous MgSO4. The solvent was removed under reduced pressure to give the product.

General procedure for Wittig olefination reaction (12a-d) 4. To a suspension of Wittig salt (1.0 mmol) in THF (10 mL) was added t-BuOK (2.0 mmol) or NaH (2.0 mmol) at 0° C. and stirred for 30 min. The aldehyde (0.8 mmol) dissolved in THF was added slowly and stirred for overnight at room temperature (at 50° C. for reactions carried using NaH, entries 2, 4, 5, 6). The reaction was quenched with H2O and extracted into EtOAc (30 mL). The organic layer was washed brine (20 mL), dried over MgSO4, filtered, and concentrated in vacuo to give the crude compound. The crude compound was purified by flash column chromatography to obtain pure product.

General procedure for demethylation: Method A (using BBr3)5. A solution of compound (74 mg, 0.192 mmol) in CH2Cl2 (70 mL) at −78° C. was treated with BBr3 (1.0 M in CH2Cl2, 0.576 mL, 0.576 mmol). The mixture was stirred at −78° C. for 2 h, and then quenched with saturated aq. NH4Cl (10 mL). The mixture was allowed to warm up to room temperature and diluted with CH2Cl2 (30 mL). The organic layer was washed with brine (10 mL), dried over MgSO4, filtered, and concentrated in vacuo.

General procedure for the demethylation: Method B (using HBr)6. The solution of compound (100 mg, 0.192 mmol) in 48% aq. HBr (3.0 ml) was heated to reflux for 3 h. After completion of the reaction, was allowed to warm to room temperature and evaporated under reduced pressure to give crude residue. The crude compound was extracted with EtOAc (30 ml) and washed with H2O (20 mL). The organic layer was separated, dried (MgSO4) and concentrated to give the product.

General method for reduction of olefin (14a-d). To a solution of olefin in 1:1 (EtOAc:MeOH) was added 10% Pd/C (10 mol %) and stirred under H2 atmosphere at room temperature for 2 h. after completion of the reaction, filtered through celite bed. The filtrate was removed under reduced pressure to afford the product.

Protein Preparations

Mouse SOX HMG fragments. The HMG domains of mouse SOX2 (Group B), SOX11 (Group C), SOX6 (Group D), SOX9 (Group E), SOX18 (Group F) and SOX15 (Group G) were BP cloned from cDNA templates (IMAGE cDNA clone IDs: Sox18: 3967084; Sox9: 5354229; Sox4: 6822618) into a pDONRTM221 pENTRY vector, sequenced and recombined into a pETG20A or a pHisMBP expression plasmid using Gateway®LR Technology (Ng et al., 2012). Constructs were transformed into *Escherichia coli* BL21 (DE3) cells (Luria-Bertani, 100 µg/ml Ampicillin).

Full-length mouse SOX18. A N-terminally tagged mouse HIS-GST-SOX18 was recombinantly expressed in Sf9 cells, purified on GST resin (GE Healthcare Life Sciences, Sweden) and eluted in Tris buffer (50 mM Tris, 500 mM NaCl, 10 mM reduced glutathione, pH 8.0). cDNA clone of mouse Sox18 was PCR amplified and cloned into the pOPIN-GST vector, to generate N-terminally tagged HIS-GST-SOX18. A sequence verified construct was co-transfected with flash-BACULTRA (Oxford Expression Technologies, Oxford, United Kingdom) baculovirus DNA onto *Spodoptera frugiperda* Sf9 cells to obtain recombinantly expressed HIS-GST-SOX18. High Five cells (BTI-TN-5B1-4) in Sf-900™ II serum-free medium were infected at cell density of 1.5×106 cells/mL with a multiplicity of infection (MOI) of 5 PFU/cell, and incubated at 21° C. for 144 h before harvest. The cell pellet from 100 mL of expression culture was resuspended in 30 mL of phosphate lysis buffer (50 mM sodium phosphate, 500 mM sodium chloride, 1% Triton X-100, 2 mM magnesium chloride, one tablet of cOmplete Protease Inhibitor Cocktail, pH 7.5) and sonicated on ice for 20 s. The cell lysate was centrifuged at 17,000×g for 40 min at 4° C. Supernatant was incubated with Benzonase Nuclease (Merck Millipore) for 1 h at room temperature for DNA degradation, before being mixed with 500 µL GST resin (GE Healthcare Life Sciences, Sweden) and incubated on a rotating wheel at room temperature for 1 h. The sample was centrifuged at 500×g for 1 min to remove unbound protein in the supernatant. The resin was further washed with 50 resin volumes (RV) wash buffer (50 mM sodium phosphate, 500 mM NaCl, pH 7.5), with unbound protein removed by centrifugation as above. Bound protein was eluted from the resin with 3×1 RV elution buffer (50 mM Tris, 500 mM NaCl, 10 mM reduced glutathione, pH 8.0), collecting the supernatant by centrifugation as above.

DNA-Binding Competition Assay Using Fluorescence Polarization (FP)

The DNA-binding competition assay was performed in black 384-well plates, with mouse full length SOX18, or SOX-HMG fragments. All experiments were performed using a fluorescently-labelled Prox1-DNA element. Controls consisted of free labelled DNA (low FP milli-Polarization index, mP), labelled DNA in presence of protein (negative control, high mP), and labelled DNA and protein in presence of competing excess of unlabelled DNA (positive control, low mP)

The DNA-binding competition assay was performed in 25 uL, in black 384-well plates, using either 30 mM HEPES (N-2-Hydroxyethylpiperazine-N'-2-Ethanesulfonic Acid) (pH 7.5, with 100 mM KCl, 40 mM NaCl, 10 mM NH4OAc, 10 mM Guanidinium, 2 mM MgCl2, 0.5 mM EDTA, 0.01% NP-40) for mouse full length SOX18, or Tris-NaCl (10 mM Tris pH 8.0 and 100 mM NaCl) for SOX-HMG fragments. All experiments were performed using a 40 bp double-stranded Prox1-DNA element with 5' fluorescein amidite (FAM) label (Sigma Proligo or InVitrogen). Optimum binding levels were obtained at 200 nM of mouse full length SOX18 and 60 nM of SOX-HMG fragment, in presence of 5 nM labelled DNA. Controls consisted of free labelled DNA (low FP milli-Polarization index, mP), labelled DNA in presence of protein (negative control, high mP), and labelled DNA and protein in presence of 400 time competing excess of unlabelled DNA (positive control, low mP). Depending on compound, final DMSO concentrations ranged from 2 to 3.33% v/v. After mixing protein, DNA probe and compound, plates were sealed and briskly agitated in the dark for 5 minutes at room temperature, 10 minutes at 37° C., and 30 minutes at room temperature, before reading fluorescence polarization on a Tecan M1000Pro ($\lambda$exc=485 nm, $\lambda$em=525 nm). All experiments were performed in triplicates.

Cell-Based Functional Assay.

Monkey kidney fibroblast-like cells (COS-7) were cultured at 37° C., 5% CO2 in DMEM (Life technologies, 11995) with FBS, sodium pyruvate, L-glutamine, penicillin, streptomycin, non-essential amino acids and HEPES. Cells were grown in 96-well plates to 80% confluency, and transfected with mouse plasmids pGL2 Vcam 1 promoter construct (VC1889) and pSG5 Sox18, using X-tremeGENE 9 DNA transfection reagent (Roche, 06365787001) (Hosking et al., 2004, Duong et al., 2014). After 4-6 h transfection, cells were incubated with compounds in 0.5% FBS medium for another 24 h, before lysis and luciferase assay (Perkin Elmer, 6016711).

Cell-Free Expression and ALPHAScreen.

Plasmid preparation and cell free-expression. All proteins were genetically encoded with enhanced GFP (GFP), mCherry and cMyc (myc) tags, and cloned into cell free expression vectors (Gagoski et al., 2015, Sierecki et al., 2013). Translation competent Leishmania tarentolae extract (LTE) was prepared as previously described to co-express protein pairs (Kovtun et al., 2011, Mureev et al., 2009).

Proteins were genetically encoded with enhanced GFP (GFP), mCherry and cMyc (myc) tags, and cloned into cell free expression Gateway destination vectors: N-terminal GFP tagged (pCellFree_G03), N-terminal Cherry-cMyc (pCellFree_G07) and C-terminal Cherry-cMyc tagged (pCellFree_G08) (Gagoski et al., 2015). Human RBPJ (BC020780) and MEF2C (BC026341) Open Reading Frames (ORFs) were sourced from the Human ORFeome collection, version 1.1 and 5.1, and the Human Orfeome collaboration OCAA collection (Open Biosystems), as previously described (Sierecki et al., 2013) and cloned at the ARVEC facility, UQ Diamantina Institute. The entry clones pDONOR223 or pENTR201 vectors were exchanged with the ccdB gene in the expression plasmid by LR recombination (Life Technologies, Australia). The full-length human SOX18 gene was synthesized and the transfer to vectors was realized using Gateway PCR cloning. Translation competent Leishmania tarentolae extract (LTE) was prepared as previously described (Kovtun et al., 2011, Mureev et al., 2009). Protein pairs were co-expressed by adding 30 nM of GFP template plasmid and 60 nM of Cherry template plasmid to LTE and incubating for 3 hours at 27° C.

ALPHAScreen was performed as previously described (Sierecki et al., 2014, Sierecki et al., 2013). The assay for disruption of protein-protein interaction (IC50) was conducted by expressing the protein pairs in LTE and incubating with a dilution range of tested compounds (0.3 to 300 µM) or DMSO (0.7% DMSO final) in buffer B for 1 h. Percentage of interaction was calculated as: (I_cpd/I_DMSO)×100 from 3 independent experiments.

ALPHAScreen was performed as previously described (Sierecki et al., 2014, Sierecki et al., 2013), using the cMyc detection kit and Proxiplate-384 Plus plates (PerkinElmer). The LTE lysate co-expressing the proteins of interest was diluted in buffer A (25 mM HEPES, 50 mM NaCl). For the assay, 12.5 µL (0.4 µg) of Anti-cMyc coated Acceptor Beads in buffer B (25 mM HEPES, 50 mM NaCl, 0.001% NP40, 0.001% casein) were aliquoted into each well. This was followed by the addition of 2 µL of diluted sample, at different concentration, and 2 µL of biotin labeled GFP-Nanotrap in buffer A. The plates were incubated for 45 min at room temperature, then adding 2 µL (0.4 µg) of streptavidin-coated Donor Beads diluted in buffer A, and incubation in the dark for 45 min at room temperature. The ALPHAScreen signal was measured on an Envision Plate Reader (PerkinElmer), using manufacturer's recommended settings ($\lambda$exc=680130 nm for 0.18 s, $\lambda$em=570/100 nm after 37 ms). The resulting bell-shaped curve is an indication of a positive interaction, while a flat line reflects a lack of interaction between the proteins. The measurement of each protein pair was repeated in triplicate.

The Binding Index was calculated as:

$$BI = \left[\frac{I - I_{neg}}{I_{ref} - I_{neg}}\right] \times 100$$

I is the highest signal level (top of the hook effect curve) and Ineg is the lowest (background) signal level. The signals were normalized to the Iref signal obtained for the strongest interaction. The assay for disruption of protein-protein interaction (IC50) was conducted by expressing the protein pairs in LTE and incubating with a dilution range or single concentration of tested compounds (0.3 to 300 µM or 50 µM) or DMSO (0.7% DMSO final) in buffer B for 1 h. Percentage of interaction was calculated as $$\left(\frac{I_{cpd}}{I_{DMSO}}\right) \times 100.$$

Data from 3 independent experiments were fitted in GraphPad Prism version 6.0 using 3-parameter non-linear regression.

Co-Immunoprecipitation (Co-IP).

Co-immunoprecipitation was performed as described previously (Sierecki et al., 2014). Briefly, SOX18-Cherry-cMyc was co-expressed with GFP-RBPJ, GFP-MEF2C or a GFP construct as negative control bait, in Leishmania tarentolae cell-free protein expression system. NaCl was added to the expressed protein (200 mM) and the samples were incubated with 10 µL of GFP-nanotrap coated beads (NHS-activated sepharose coupled with MBP-GFP-Nanotrap) for 30 min at 4° C. with gentle mixing by rotation. Subsequently, the beads were washed 6 times with 200 µL of wash buffer (PBS with 0.1% Triton X-100 and 200 mM NaCl). The proteins were released from the beads by heating for 3 min at 72° C. in 15 µL of 2× NuPAGE LDS loading buffer and resolved on NuPage Novex 4-12% gel (Life Technologies, Australia). The gel was scanned for GFP and Cherry fluorescence using a ChemiDoc MP System (Bio-Rad, Australia).

Critical Micelle Concentration (CMC).

Critical micelle concentration was determined based on the incorporation of fluorescent 1,6-diphenyl-1,3,5-hexatriene (DPH) into micelles (Chattopadhyay and London, 1984). Small molecules and positive controls (neutral detergent Triton X100 and anionic detergent SDS) were cascade diluted in low binding 96-well plates from 1000 μM to 0.1 μM. Dilutions were performed in 200 mM NaCl or FP buffer. DPH was supplemented at 5 μM into black 384-well plates. Fluorescence intensity ($\lambda$exc=360 nm, $\lambda$em=430 nm) was measured following a 30-min incubation at room temperature, to graphically estimate CMC transition.

Cytotoxicity Assay.

Cell toxicity was determined using Alamar blue, as previously described (McMillian et al., 2002). COS-7 cells were seeded as 7000 cells per well in black wall clear bottom 96-well plates in DMEM medium (Life Technologies Australia) with 10% FBS. HepG2 and HEK293 cell lines, from ATCC, were seeded as 5000 cells per well in black wall clear bottom 384-well cell culture plates in DMEM with 1% FBS. Cells were cultured for 24 h at 37° C., 5% CO2. A serial dilution of compounds was added, with a final DMSO concentration adjusted to 0.5% v/v. Cells were incubated for another 24 h. 1% Triton X-100 was used as negative control, and 0.5% DMSO as positive control. 5 μM Alamar blue was added to each well and fluorescence was measured ($\lambda$exc=560 nm, $\lambda$em=590 nm) after 2 h incubation at 37° C. Data were analysed using Prism software.

Direct DNA-Binding Assay, Using Surface Plasmon Resonance (SPR).

Compounds were tested at a 1% v/v DMSO in HBS-EP buffer (10 mM HEPES, 150 mM NaCl, 3 mM EDTA, 0.005% v/v polysorbate 20, pH 7.4). The same buffer supplemented with 1% v/v DMSO was used as a mobile phase. DNA minor groove binder DAPI (4',6-diamidino-2-phenylindole), DNA intercalator and minor groove binder actinomycin D, and DNA intercalator ethidium bromide were used as positive controls. Biotinylated (one tag per probe) double strand DNA probes were prepared using a standard annealing routine (5 min at 100° C., room temperature overnight and stored at −20° C.) of single strand anti-parallel DNA Probes purchased from Geneworks and were immobilized on CM5-SA streptavidin chips as per manufacturer's recommendations. Running buffer flow was set at 25 μL/min, cycles consisted of 4 min association, 4 min dissociation, followed with a pulse of 10 s of 10 mM Gly-HCl pH 2.5 for regeneration, and a 1 min stabilization, for compounds and actinomycin D. DAPI did not require any regeneration, whereas for ethidium bromide, a 40 s pulse at 25 μL/min of 0.5% v/v SDS was required for regeneration before stabilization. All sample and control cycles were performed in triplicate. DMSO calibration was performed as per manufacturer's recommendations. After each injection, an extra flow system wash was performed with 50% v/v DMSO to avoid carryover. Experiments were run on a Biacore T200 (GE Healthcare, USA), with one flow cell kept as a reference.

Direct Protein Binding Assay (Thermal Aggregation).

Differential static light scattering studies were conducted on a Harbinger Biotech StarGazer using mouse SOX18-HMG (109aa) in the presence and absence of either Prox1-DNA or putative small molecule ligands. An initial experiment was conducted to evaluate the compound concentration for which the change in aggregation temperature was no longer dependent on concentration. The final concentration that was used ranged from 500 μM (Sm4 and Sm14) to 1.5 mM (Sm5), depending on the necessity to limit the concentration of DMSO to 3%. A 17 bp Prox1-DNA oligonucleotide was used at a final concentration of 10 μM. Binding was performed in triplicate and detected by an increase in Tagg (aggregation temperature) of >2° C. in the presence of the ligand. Tagg was measured with the same protein batch in one single run. The reaction was carried out in Tris-NaCl buffer (10 mM Tris-HCL, 150 mM NaCl, pH 8) with 3% v/v DMSO, in a final reaction volume of 45 μl and with a mouse SOX18-HMG concentration of 154 μM. These were incubated for 1 h at room temperature before measurement. The protein was heated from 25° C. to 80° C. at a rate of 1° C. per min. Total intensities were plotted against temperature for each sample, and fitted to the Boltzmann equation by non-linear regression.

In Silico Docking and Molecular Dynamics

Ligand-protein docking. In silico docking of Sm4 into the SOX18/DNA complex was performed using LeadIT/FlexX (BioSolveIT, Germany). The docking was performed by removing all the water molecules from the structure of SOX18-HMG/Prox1-DNA (pdb: 4Y60) and defining the whole protein/complex as possible binding site: The best 20 docking poses of Sm4 were analysed and grouped into 4 clusters. As the SOX18/DNA does not contain a classic binding pocket, each pose cluster was further validated by a 200 ns long MD simulation. The MD simulation was performed using the full SOX18/DNA structure with Sm4 in its different binding pose. Analysis of the MD simulations revealed three of the poses as unstable, with the Sm4 breaking its interaction with the protein within the first 3 to 14 ns of the simulation, remaining in the water solvent for the remaining of the simulation. Only for one of the poses the MD simulation produced a stable binding poses for Sm4 during the entire 200 ns simulation. Similarly, docking and MD simulations were performed with Sm4 and SOX18 without DNA. However, none of the 4-pose cluster produced a stable binding orientation during the MD simulation. For comparison, MD simulations were performed for SOX18/DNA and SOX18 without DNA, without Sm4, producing similar conformations and dynamic behaviour as the structures with Sm4 ligand.

Protein-protein docking. The protein-protein docking between Notch1 transcription complex and SOX18 was performed with ClusPro online server version (cluspro.b-u.edu), using pdb: 3V79 and pdb: 4Y60 for the structures of Notch1 transcription complex and SOX18-HMG, respectively. DNA molecules were removed before docking, as ClusPro is unable to process them, and restored after docking. Docking solutions with clashing DNA molecules were rejected. The resulting top docking pose was used as starting conformation in a 50 ns long MD simulation to optimize the docking pose, and validate the stability of the multi protein complex.

MD simulations. Any MD simulation was carried using the AMBER MD software "pmemd", using the ff99SB force field for the protein and DNA, TIP3 for implicit water, and applying periodic boundary conditions (NTP), particle-mesh Ewald (PME) method for long-range electrostatic interactions, isotropic pressure coupling and Langevin thermostat (gamma_ln=1/ps) for temperature coupling. The simulations were run with 2fs step size, constraining bonds involving hydrogens using the SHAKE algorithm. For MD simulations with Sm4, Antechamber from the AMBER package was used to calculate the force field parameter for the ligand. All MD simulations were performed by minimizing the structures and equilibrating them by reducing the position constrains slowly over 5 ns. Each simulation was done in triplicate, using different random number for the assignment of the initial velocities.

COX1/COX2 Enzymatic Assay

COX inhibition activity was measured using COX1 and COX2 inhibitor screening assay kits from Cayman Chemical Company (Ref #701090 and 701080). All compounds were tested in quadruplicate at a single 200 µM concentration in 2% v/v final DMSO. Compounds were preincubated with ovine COX1 or human COX2 at 37° C. for 10 min before incubation with COX substrate arachidonic acid for another 3 min. Reactions were stopped by addition of concentrated hydrochloric acid. Prostanoid standard curve was prepared and enzyme immunoassay performed as per manufacturer's description. A DMSO control, a 100% inhibition control with heat-inactivated COX enzyme, as well as a 200 µM meclofenamate positive control (potent non-selective COX1/2 inhibitor), were included for reference. Prostanoid standards values were plotted as log it (B/B0) versus log concentrations and fitted with linear regression using Graph-Pad Prism version 6.0. Standard curve linear fit was used to calculate each samples concentrations.

SOX18 Single Molecule Tracking

Figure 24:
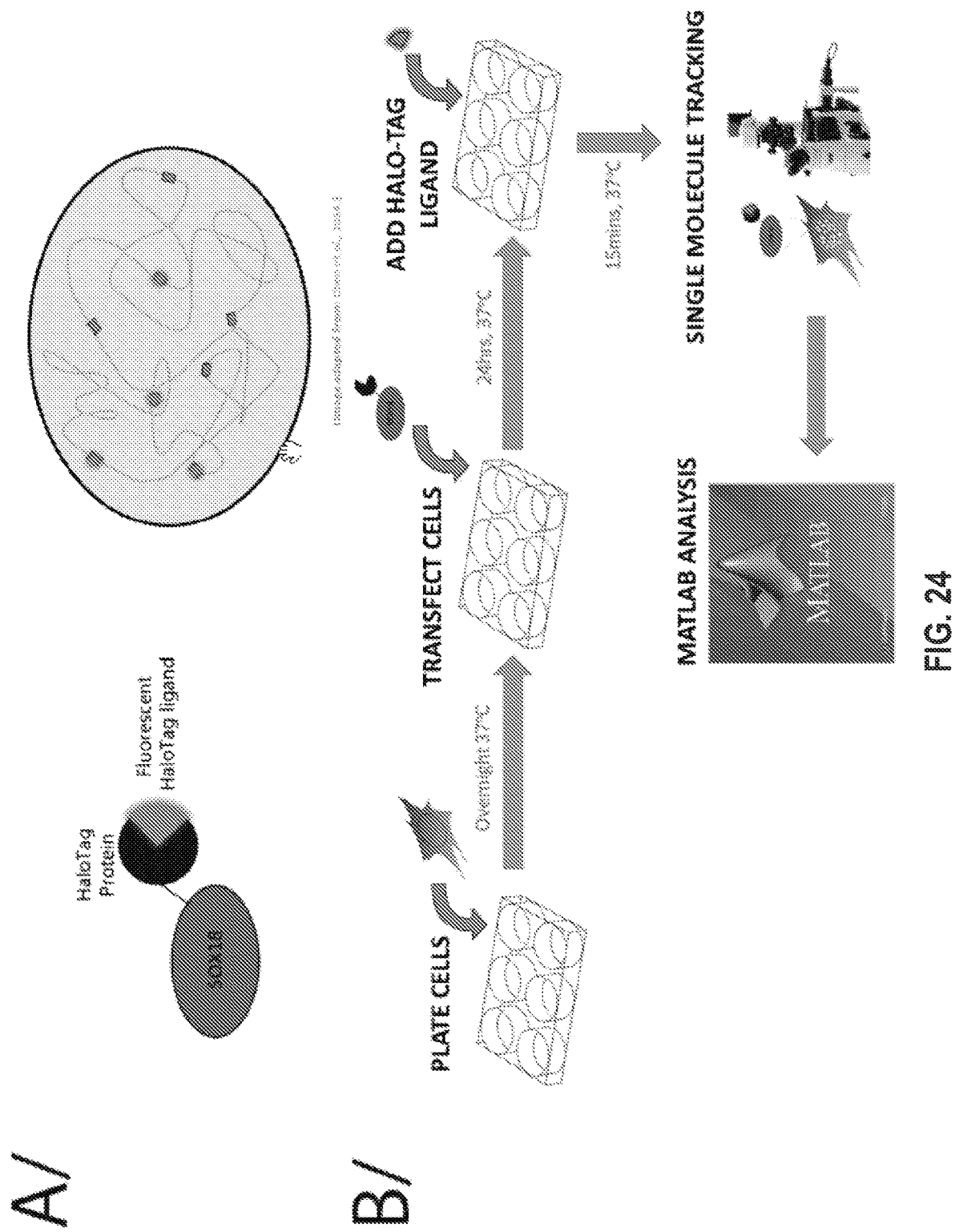
FIG. 24: (A) describes the principle for Single Molecule Tracking (SMT) which allows real-time imaging in live cells of chromatin binding dynamics of transcription factors, such as SOX18. The SOX18-Halotag reporter construct is shown. SMT determines a search pattern of the SOX18 protein while it scans the genome to bind to specific responsive elements of its target genes. (B) depicts the experimental workflow. Cells are plated overnight prior to transfection with the SOX18-Halotag protein and incubated overnight. The Halo-tag ligand is then added to the cells. SOX18 molecules are either bound to DNA (immobile) or are unbound and freely diffusing in the nucleus. Within the immobile fraction it is possible to define 2 populations either specific binding or non-specific binding based on the dwelling time on the chromatin. This enables detection of a single molecule of SOX18 protein upon addition of the ligand which becomes fluorescent after enzymatic processing by the Halotag system. Real time imaging is performed using a modified version of TIRF microscopy (HiLo) using a ZEISS ELYRA super-resolution microscope. Analysis was performed using the MATLAB programming algorithm (C) Top; Sm4 increases SOX18 specific bound fraction at the expense of the non-specific bound fraction in a concentration-dependent manner. The % shown in the pie charts shows specific and non-specific immobile DNA bound fraction depending on the dwelling time in one same DNA position, whereby a short time of less than 1 sec is considered to be non-specific binding and specific binding is considered 5-6 secs of SOX-18 DNA binding. Bottom; Sm4 increases the dwell time of the specifically bound SOX18 fraction while decreasing the dwell time of the non-specifically bound fraction. (D): Top; Sm4 selectively engage SOX18 dominant negative mutant Ra$^{op}$ "Ragged Opossum" mutant contributing to its partial rescuing as, conversely, it decreases Ra$^{op}$ specific bound fraction at the benefit of the non-specific bound fraction, in a concentration-dependent manner. Bottom; Sm4 has the same effect on dwell times of specifically and non-specifically bound Ra$^{op}$ fractions than on SOX18 fractions, but the effect is more marked.
Figure 24:
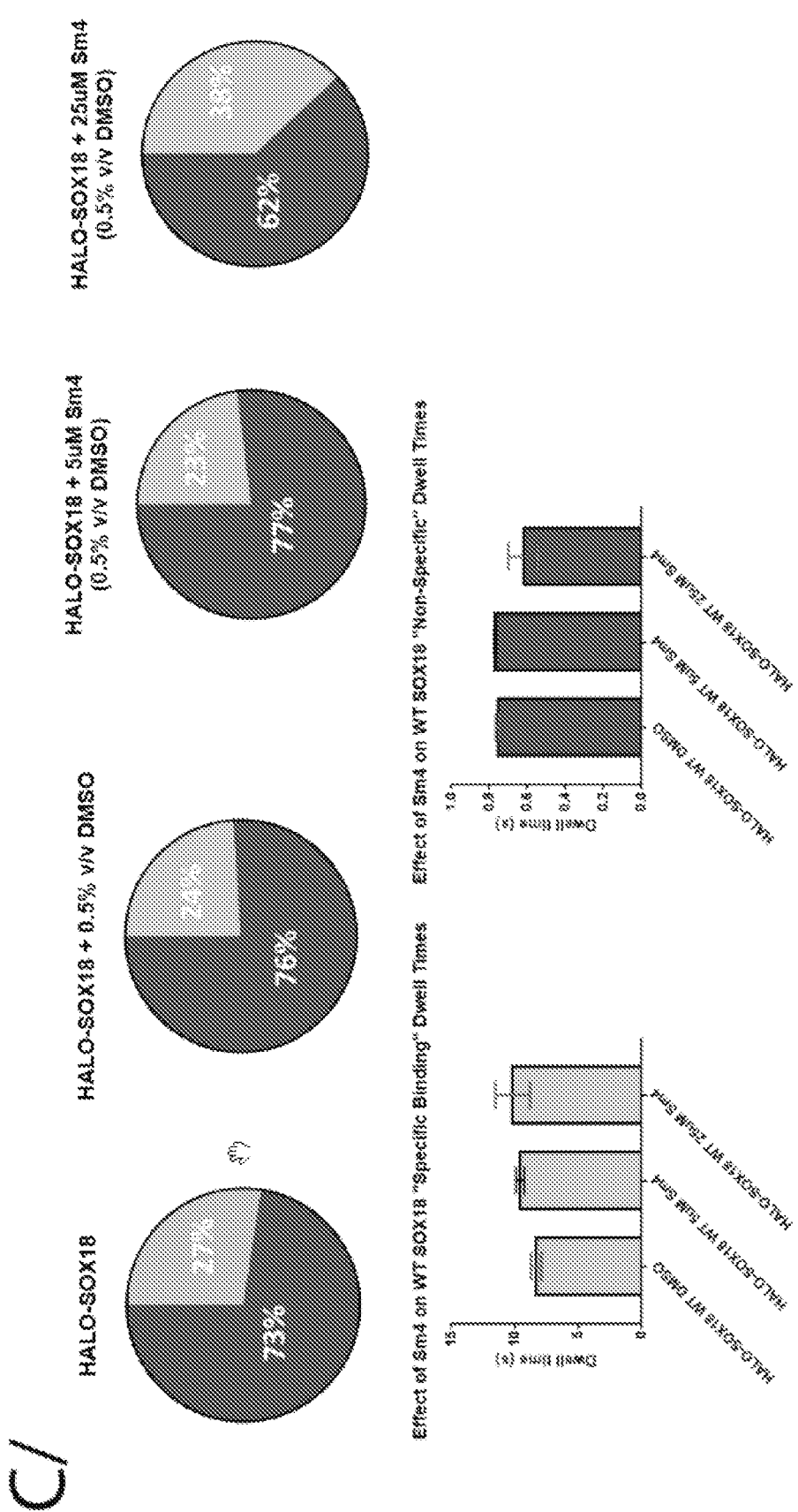
Figure 24:
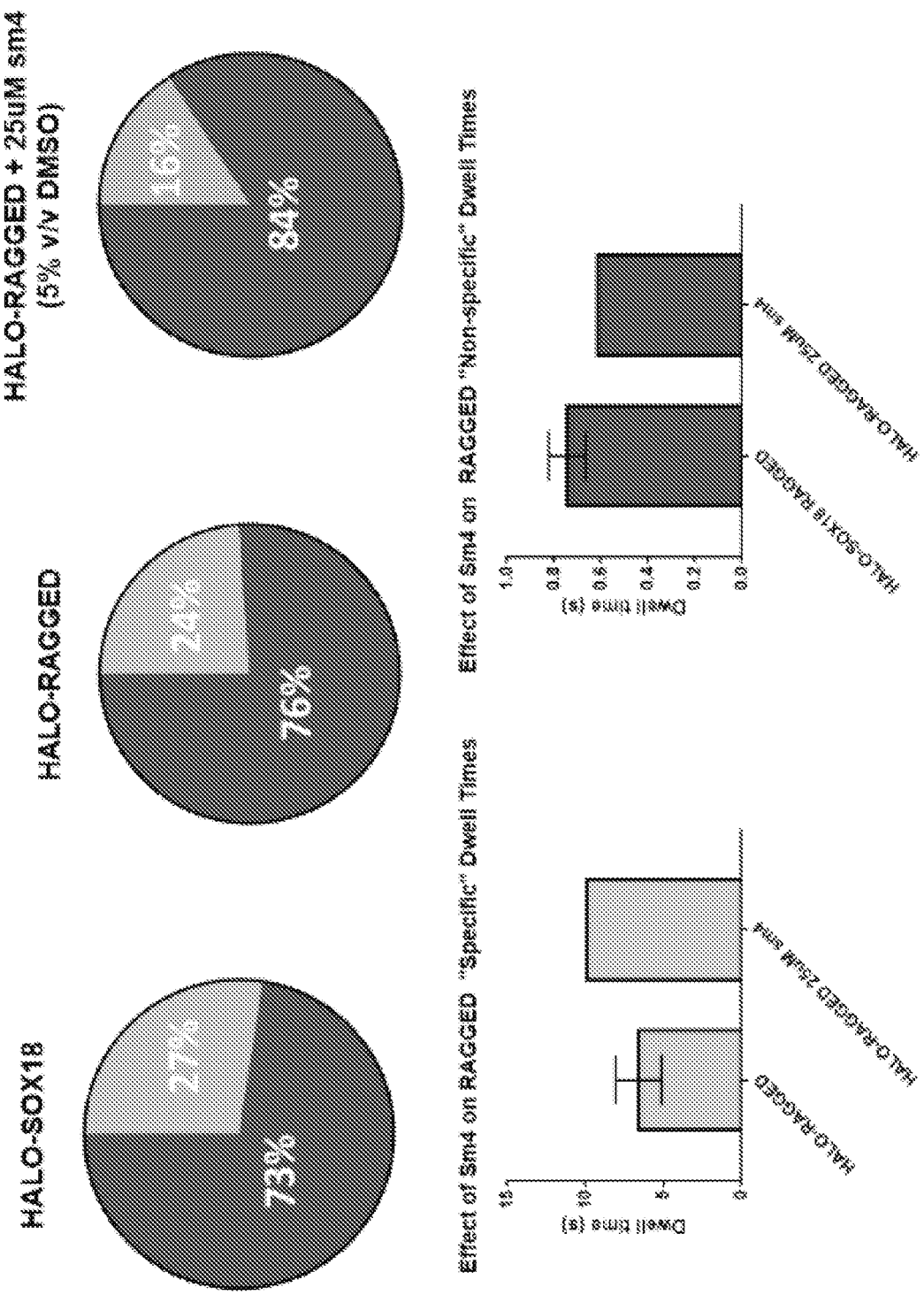

FIG. 24B depicts the experimental workflow, which involves bi-dimensional tracking of molecule trajectory and analysis using MATLAB, as outlined in Chen et al. (Cell 156, 1274-1285; 2014). We note that the immobile DNA bound fraction (%, shown in pie graphs) is of two types, specific and non-specific, depending on the dwelling time in one same DNA position; if of a short time (less than 1 second average) this is considered to be non-specific binding (i.e., transient binding to random DNA sites), and if of a long time (greater than 5-6 seconds average) this is considered to be specific binding (i.e., longer binding to target DNA sites with transcriptional effect). The dwell times of immobile DNA bound fractions (shown as bar graphs) is also of two types, specific and non-specific: The length of time in seconds that SOX18 molecules bind to DNA non-specifically (on average less than 1 second) or specifically (on average greater than 5-6 seconds). Single molecule tracking is performed after transfection of Hela cells with a SOX18-Halotag reporter construct. This expression vector enables us to detect single molecule of SOX18 protein upon addition of a ligand which becomes fluorescent after enzymatic processing by the Halotag system. Real time imaging is performed using a modified version of TIRF microscopy (HiLo) using a ZEISS ELYRA super-resolution microscope.

Results

Screening of Natural Products for Inhibition of SOX18-DNA Binding.

A marine extract library was screened for inhibitors of SOX18 protein (full-length murine) binding to DNA, using a fluorescence polarization-based assay (FP). We selected a fluorescently labelled oligonucleotide harbouring a consensus SOX motif, found in the first intron of Prox1 gene, a SOX18 direct target (Francois et al., 2008) (FIG. 1A). The library includes 2,000 purified metabolites, as well as 2,688 marine extracts, containing in excess of 50,000 structures. This primary screening identified sixteen active extracts collected from various phyla, namely sponges (10), algae (5) and tunicate (1) (hit rate 0.6%, primary screening Z'-factor=0.62) (Zhang et al., 1999). Subsequent extracts deconvolution was prioritized based on potency and abundance of biologically active molecule(s), with the most active extract, from the brown algae Caulocystis cephalornithos, producing two active compounds: 6-undecyl salicylic acid (Sm1), and 6-tridecyl salicylic acid (Sm2) (FIG. 1B). Dose response screening for both Sm1 and Sm2 resulted in inhibitory effects (IC50) in the high micromolar range (FIG. 1C). Both active compounds contain a salicylic acid scaffold with a large aliphatic group.

Design and Primary Screening of Focused Library.

In the next step, we designed a small library of analogues to validate the salicylic acid (hydroxyl benzoic acid) active scaffold, and investigate its structure-activity relationship profile. The selection, shown in FIG. 2A, also included compounds with a similar resorcinol scaffold (replacing the carboxyl acid with an additional hydroxyl), as well as a number of approved NSAID that contain a similar salicylic acid or anthranilic acid scaffold (replacing the hydroxyl with an amine). The library was purchased, and screened for inhibition of SOX18-DNA binding, using the FP assay. In this assay, disruption of high affinity protein-DNA interaction requires an inhibitor concentration in the high micromolar range, at which aggregation can occur, especially in the case of amphiphilic and high log P molecules (Irwin et al., 2015). Therefore, the compounds were counter-screened for critical micelle concentration (CMC), to eliminate aggregate- or micelle-forming compounds as false positives (Table 1, columns 2 and 5, and FIG. 2B).

Figure 2:
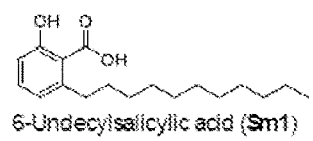
FIG. 2: Focused library of structural analogues and counter-screen with in-silico aggregation predictor and critical micelle concentration (CMC) assay. A. First group is based on the ortho-hydroxybenzoic (salicylic acid) motif apparent in compounds Sm1 and Sm2. Second group is based on a similar resorcinol scaffold. Third group consists in approved NSAIDs that contain a similar salicylic acid or anthranilic acid scaffold. B. Typical CMC data for neutral detergent Triton X100 control and two compounds Sm4 and Sm10. C. SOX18-DNA binding inhibition by Sm4, meclofenamic, niflumic and flufenamic acids.
Figure 2:
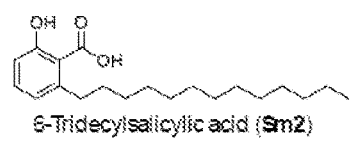
Figure 2:
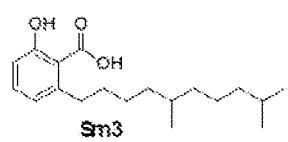
Figure 2:
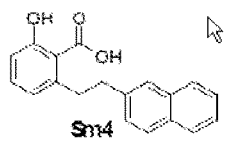
Figure 2:
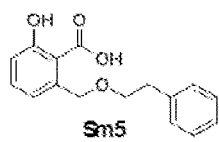
Figure 2:
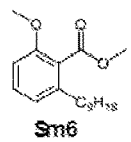
Figure 2:
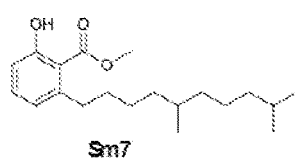
Figure 2:
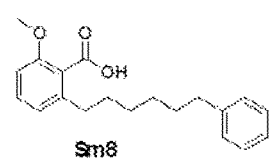
Figure 2:
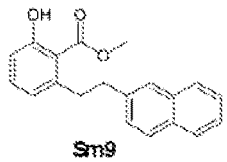
Figure 2:
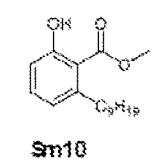
Figure 2:
Figure 2:
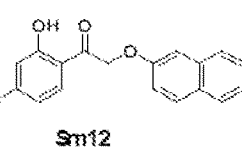
Figure 2:
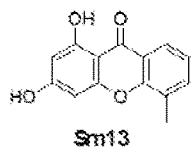
Figure 2:
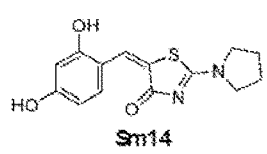
Figure 2:
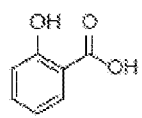
Figure 2:
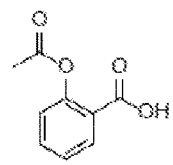
Figure 2:
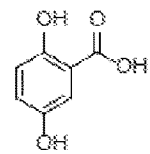
Figure 2:
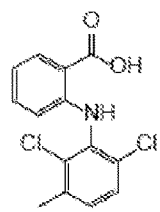
Figure 2:
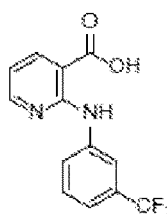
Figure 2:
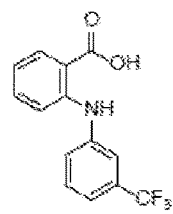
Figure 2:
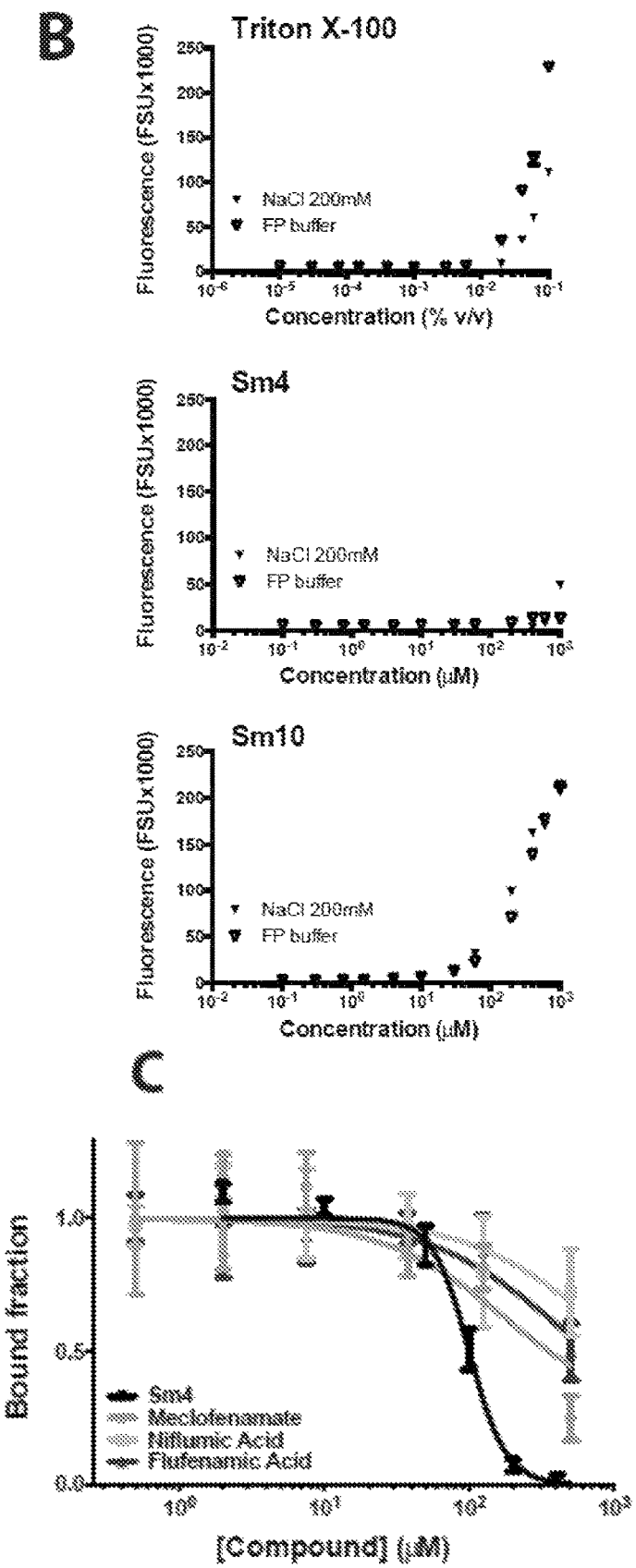

The CMC assay eliminated five compounds, Sm3, Sm6, Sm7, Sm9 and Sm10, displaying a CMC at 20 and 30 µM (Table 1, column 2). The remainder displayed no micelle formation up to 1000 µM and were included in the SOX18-DNA binding assay. The CMC of Sm1 and Sm2 could not be determined due to short supply of compounds. The SOX18-DNA binding assay identified 7 compounds with IC50 values below 1000 µM, with 2, Sm4 and Sm14, showing improved IC50 values of around 100 µM compared to the original hits Sm1 and Sm2 (IC50 of around 350 µM) (Table 1, column 1; FIG. 2C). Interestingly, all three anthranilic acid analogues, meclofenamate, niflumic acid and flufenamic acid, also display activity with IC50 values in the 100-400 µM range (Table 1, column 1; FIG. 2C).

In order to pinpoint the possible binding site of the small molecules, the FP assays were repeated with a shorter, DNA-binding centred protein fragment. The DNA binding domain of SOX TFs consists of the 79 amino acid long High Mobility Group (HMG) box. The 109 amino-acid long SOX18 fragment (SOX18[109]) corresponds to residues 69-177 (numbering by mouse SOX18), which includes the HMG box (residues 78-149) and N- and C-terminal flanking sequences of 9 and 28 amino-acids, respectively. FP assay with the SOX18[109] fragment displayed almost identical IC50 values to full length SOX18 (data not shown) suggesting that small molecules interfere with this 109 aa portion of the protein.

Binding Selectivity.

Figure 3:
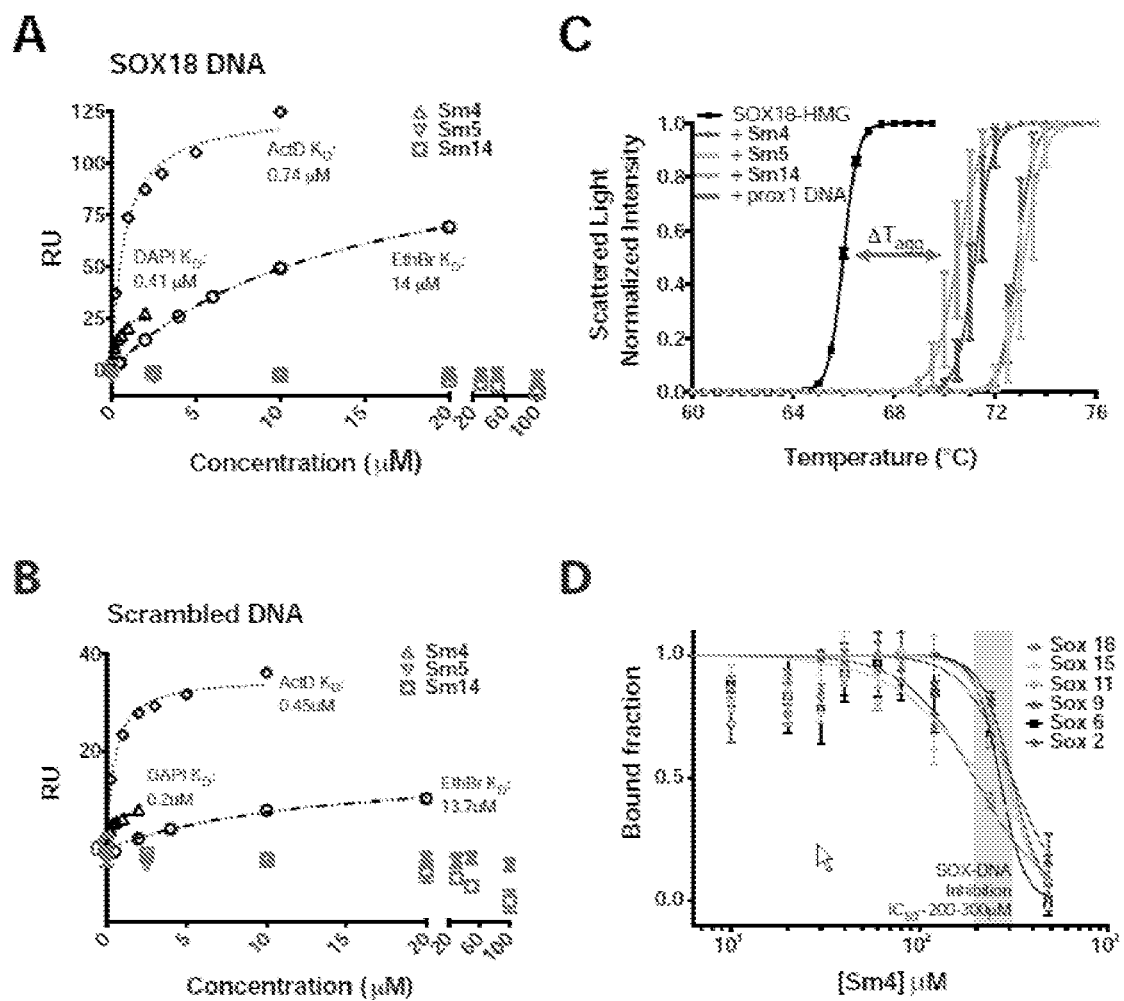
FIG. 3: Compounds interact with SOX protein but not DNA. A., B. Biotinylated double-strand DNA probes, approximately 40 base pair-long, with a SOX18 consensus element (A.) or a scrambled sequence (B.), and flanked with genomic DNA, were used to test small molecules DNA binding. Probes were immobilized on an SPR streptavidin chip. Positive controls DAPI, ethidium bromide, and actinomycin D bind to DNA in a manner consistent with literature. Small molecule inhibitors (Sm4, 5 and 14) do not bind to consensus, or scrambled DNA. C. Thermostability of SOX18[109] HMG fragment in the presence of either Prox1-DNA, Sm4, 5 or Sm14, as measured by differential static light scattering of protein complex heated from 25 to 80° C. The binding of small molecules promotes protein stability ($\Delta Tagg>3°$ C. is considered a significant stabilization). Boltzmann curve fits of normalized light scattering triplicate data (Fitting goodness $R_2>0.97$). D. Sm4 inhibits DNA binding of SOX2, 6, 9, 11, 15, and 18-HMG fragments as measured with FP-based DNA-binding competition assay.

From a molecular viewpoint, an inhibitor of SOX18-DNA binding could act either by interacting directly with the DNA, or the protein, or at the interface between protein and DNA. Binding of small molecules directly to the DNA, even though reported for other TFs (Leung et al., 2013), has the potential for unspecific DNA binding, leading to possible genotoxicity, mutagenicity, or carcinogenicity. For this reason, we developed a direct binding assays to determine whether the active compounds interact directly with DNA or protein. A surface plasmon resonance-based method was developed to analyse the binding of small molecules to biotinylated double stranded DNA immobilized on the surface of a streptavidin chip. The method measures the rate of binding (kon), dissociation (koff) and binding constant (KD), and was used to measure the binding to two different DNA sequences: SOX binding site consensus DNA, and scrambled DNA. Intercalating agents ethidium bromide and Actinomycin D, and the minor groove-binding agent 4',6-diamino-2-phenylindole (DAPI) were used as positive controls for unselective DNA binding. All positive controls displayed KD independent of DNA sequence and consistent with literature. This analysis showed that none of the SOX18 inhibitors displayed any binding to either consensus or scrambled DNA (FIGS. 3A and 3B).

To investigate whether the inhibitors interact directly with the protein, we measured the resulting increase in SOX18 thermostability, by assessing the shift to higher temperature of protein unfolding equilibrium (Shrake and Ross, 1992, Shrake and Ross, 1990, Brandts and Lin, 1990, Fukada et al., 1983). For this, we used static light scattering as a readout of protein-inhibitor complexes aggregation (Mittal et al., 2014, Senisterra et al., 2006, Senisterra et al., 2008, Senisterra and Finerty, 2009, Senisterra et al., 2012). Thermal stability was measured using HMG only SOX18[109] fragment, and a DNA probe decorated with SOX motifs, as positive control. Sm4, Sm5 and Sm14 were tested at concentrations saturating all SOX18 potential binding sites, respectively 500 µM for Sm4 and Sm14 and 1.5 mM for Sm5. In these maximum ligand binding conditions, temperature-dependent protein aggregation is no longer limited by binding site occupancy and was measured until a plateau was reached. Each inhibitor displayed an increase in Tagg of more than 3° C., consistent with direct interaction of inhibitors to protein (FIG. 3C). Taking both binding studies together, results suggest that small molecule inhibitors interact with SOX18 protein, without interacting directly with DNA. In addition, combined data from the FP assay and the thermal stability assay suggest that the inhibitor-protein interaction site is located in or in close proximity of the SOX18-HMG box.

SOX DNA-Binding Inhibition Selectivity.

The DNA binding domains of all SOX proteins are highly conserved, sharing 46% sequence identity with the HMG domain of mammalian testis-determining factor SRY (Bowles et al., 2000, Gubbay et al., 1990), while the remaining domains of the SOX TFs, flanking the HMG domain, show low levels of similarity. To investigate the selectivity of the SOX18 inhibitors, HMG only protein fragments from different SOX proteins were used in the DNA-binding FP based assay, using a fluorescently labelled oligonucleotide harbouring a known SOX motif, 5'AACAAT3'. The different SOX TFs include: SOX2 (Group B), SOX11 (Group C), SOX6 (Group D), SOX9 (Group E), SOX18 (Group F), and SOX15 (Group G). The most active inhibitor Sm4 was assessed against all different SOX TFs, displaying DNA-binding inhibition in all cases (IC50 around 200-300 µM) with a slight preference for SOX18 and SOX15 (IC50 around 200 to 220 µM versus 270 to 310 µM for others), suggesting that for DNA-binding disruption the inhibitor is non selective amongst SOX TFs (FIG. 3D).

Off Target Analysis.

COX inhibition. Salicylates are an important class of NSAIDs acting via direct or indirect suppression of cyclooxygenase (COX) dependent production of pro-inflammatory prostaglandins (Pillinger et al., 1998). In this study, we identified SOX18 inhibitors with structural similarities to COX inhibitors, and in order to investigate any functional overlap between NSAID and the novel SOX18 inhibitors, we included structurally similar NSAID in the SOX18 investigation. Similarly, we investigated whether novel SOX18 inhibitors would inhibit COX1/2 enzymatic activities. COX-1 and COX-2 inhibitory effects of Sm4, Sm5, Sm8, Sm11, Sm12, Sm13 and Sm14 were assessed using a commercial COX-1/2 ELISA assay, and using meclofenamic acid as positive control. None of the SOX18 inhibitor display any COX-1 or COX-2 inhibitory activity up to a concentration of 200 µM (FIG. S1A, S1B).

Off-target profiling. We further explored potential SOX18-independent effects of our lead Sm4 with a Eurofins-CEREP/Panlabs panel of radioligand binding assays to various receptors, enzymes and transporters, including G-protein-coupled receptors (GPCRs), ion channels, membrane receptors, kinases and non-kinase enzymes, and nuclear receptors, involved in a broad range of potential off-target effects (Table 4). A number of epigenetic modifiers were also tested using a series of recombinant-enzyme fluorimetry assays. No significant inhibition (>50%) was observed at 10 µM, demonstrating Sm4 selectivity and potential for further drug development.

SOX18 Protein-Protein Interaction

The highly conserved HMG domain of SOX transcription factors has been reported to be involved in both protein-DNA and protein-protein interaction (Agresti and Bianchi, 2003, Prokop et al., 2012, Huang et al., 2015). Hence, compounds that bind directly to or in close proximity of the HMG domain have the potential to modulate both SOX18-DNA and SOX18-protein interactions, either directly or by allosteric changes to the conformation of the SOX18 protein. To investigate the potential of our small molecules to modulate SOX18-protein interactions, we selected two SOX18 PPIs known to be involved in the transcriptional regulation of endothelial cells: MEF2C, reported to bind to SOX18 in a GST-pull down assay (Hosking et al., 2001), and RBPJ, reported to interact genetically with SOX18, while no direct binding has been identified yet (Sacilotto et al., 2013). In addition, XRCC6 (ATP-Dependent DNA Helicase II) was selected as negative control, as a non-binding partner.

Figure 4:
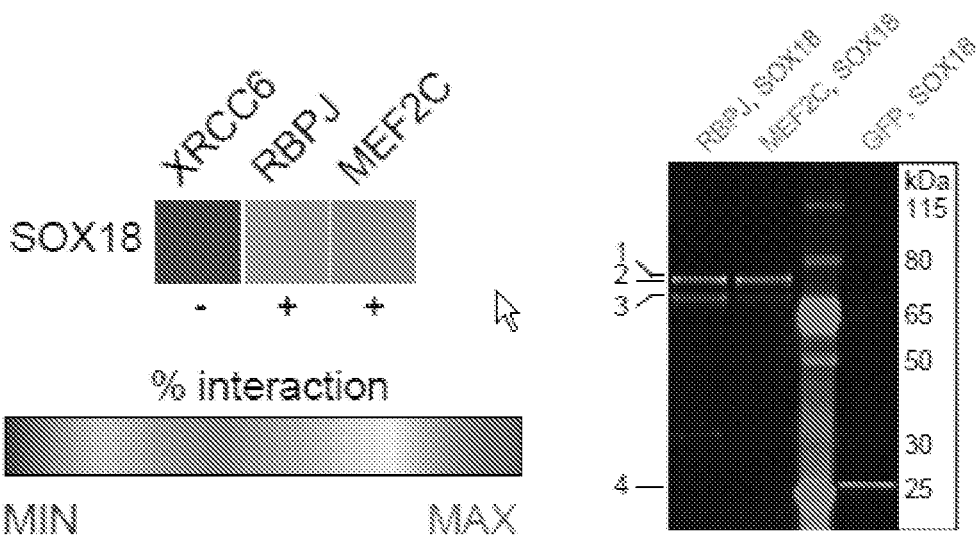
FIG. 4: Effect of Sm4, niflumic, flufenamic, and meclofenamic acids on SOX18 protein-protein interactions. A. Left Panel: Heatmap of SOX18 pairwise protein-protein interactions as tested by ALPHAScreen, on XRCC6 (negative control) and two proteins known to interact with SOX18, RBPJ and MEF2C. Right Panel: Coimmunoprecipitation of protein complex. SOX18-mCherry-cMyc was co-expressed with either GFP-RBPJ, GFP-MEF2C, or GFP-only (negative control) under cell-free conditions and immunoprecipitated with GFP Nanotrap beads. Bands: 1. RBPJ-GFP, 2. MEF2C-GFP, 3. SOX18-mCherry, 4. GFP. B. Effect of Sm4, niflumic, flufenamic and meclofenamic acids on SOX18 interaction with MEF2C and RBPJ.
Figure 4:
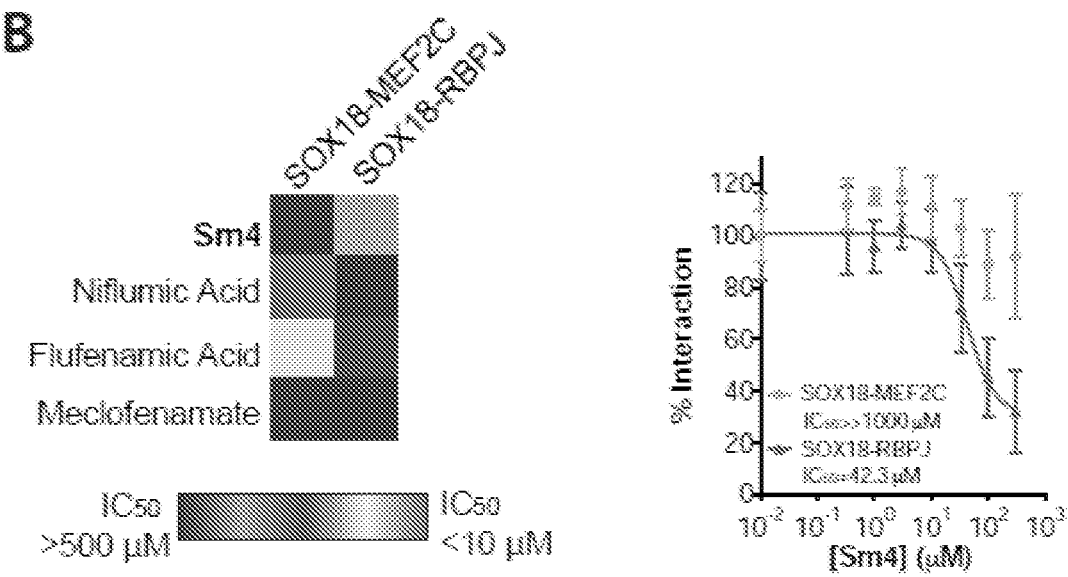
Figure 4:
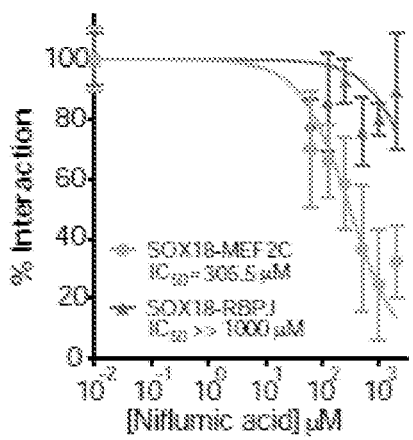
Figure 4:
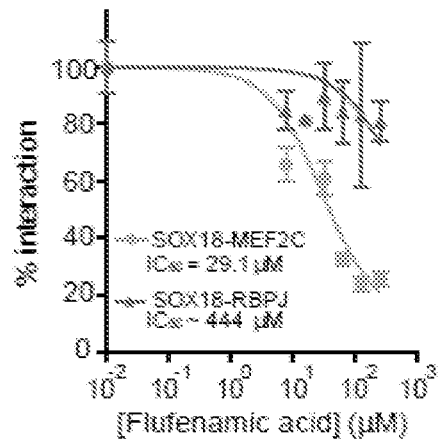

We analysed PPI inhibition using a cell-free expression system to express tagged proteins, and combined it with ALPHAScreen technology (Amplified Luminescent Proximity Homogeneous Assay) enabling us to measure tagged proteins propinquity (Sierecki et al., 2013). This approach confirmed direct pairwise interaction between SOX18 and its known partner MEF2C, and revealed a direct PPI between SOX18 and RBPJ (FIG. 4A, Left Panel). Direct physical interaction was further validated using standard co-immunoprecipitation (FIG. 4A, Right Panel). Next, we investigated the ability of our most potent small compound, Sm4, as well as meclofenamic acid, niflumic acid and flufenamic acid, to disrupt SOX18-MEF2C or SOX18-RBPJ interactions. Sm4 disrupts SOX18-RBPJ interaction with an IC50 of 42.3 µM, but has no effect on SOX18-MEF2C interaction (FIG. 4B, Top Left and Top Right Panels). Conversely, flufenamic disrupts the SOX18-MEF2C interaction (IC50 of 29.1 µM), while only weakly the SOX18-RBPJ interaction (IC50 of ~444 µM) (FIG. 4B, Top Left and Bottom Right Panels). The other NSAID showed little or no effect on any of the PPI.

SAR Library.

Figure 5:
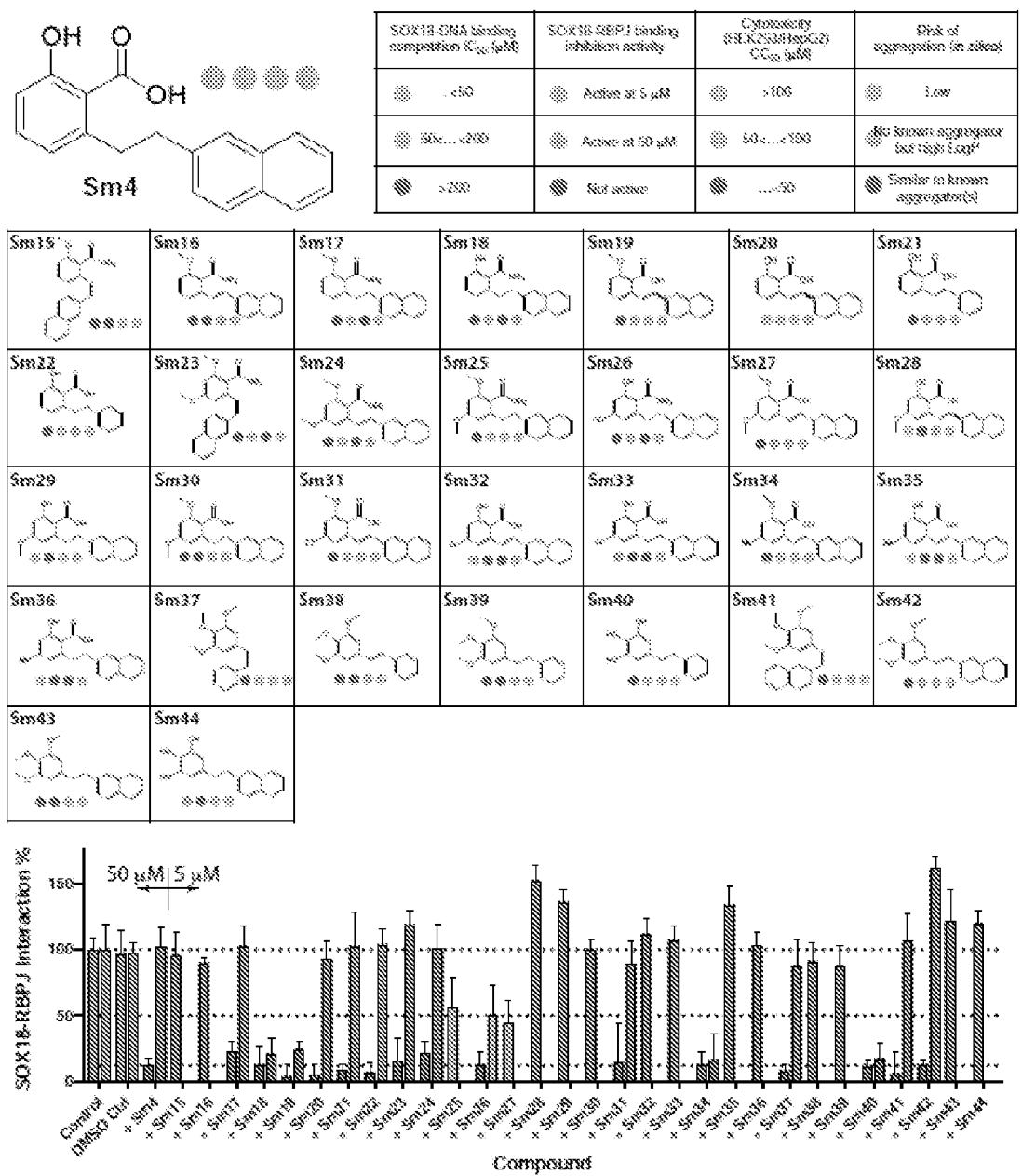
FIG. 5: Contribution of Sm4 chemical motives to SOX18 DNA binding inhibition, SOX18-RBPJ binding inhibition, cytotoxicity and aggregation. Top-panel table depicts Sm14-44 compounds and summarizes in a colour-coded manner results obtained for four activity markers, namely, protein-DNA and protein-protein binding inhibition, cytotoxicity and aggregation risk. The second bottom bar graph details SOX18-RBPJ protein-protein binding inhibition results at 50 µM and 5 µM where available (N=4, mean±SD). (DNA-binding inhibition, cytotoxicity and cLogP raw data are summarised in Table 3). The bottom bar graph illustrates SOX18-RBPJ protein-protein interaction (PPI) inhibition as measured by ALPHAScreen assay. Results are shown at 50 µM (left bars for PBS Ctrl, DMSO Ctrl and Sm4) and 5 µM (right bars for Sm4-Sm44). Of note results are shown when compound available (N=4, mean±SD). Comparison of PPI disruption of the Sm4 series tested at 5 µM using SOX18 homodimer and SOX18/RBPJ heterodimer formation as a readout in ALPHAScreen assay. Some compounds preferentially disrupt SOX18 homodimer formation whereas some other are more specific to SOX18 heterodimer formation and some other are pan disruptors of both homo- and heterodimer complex.
Figure 5:
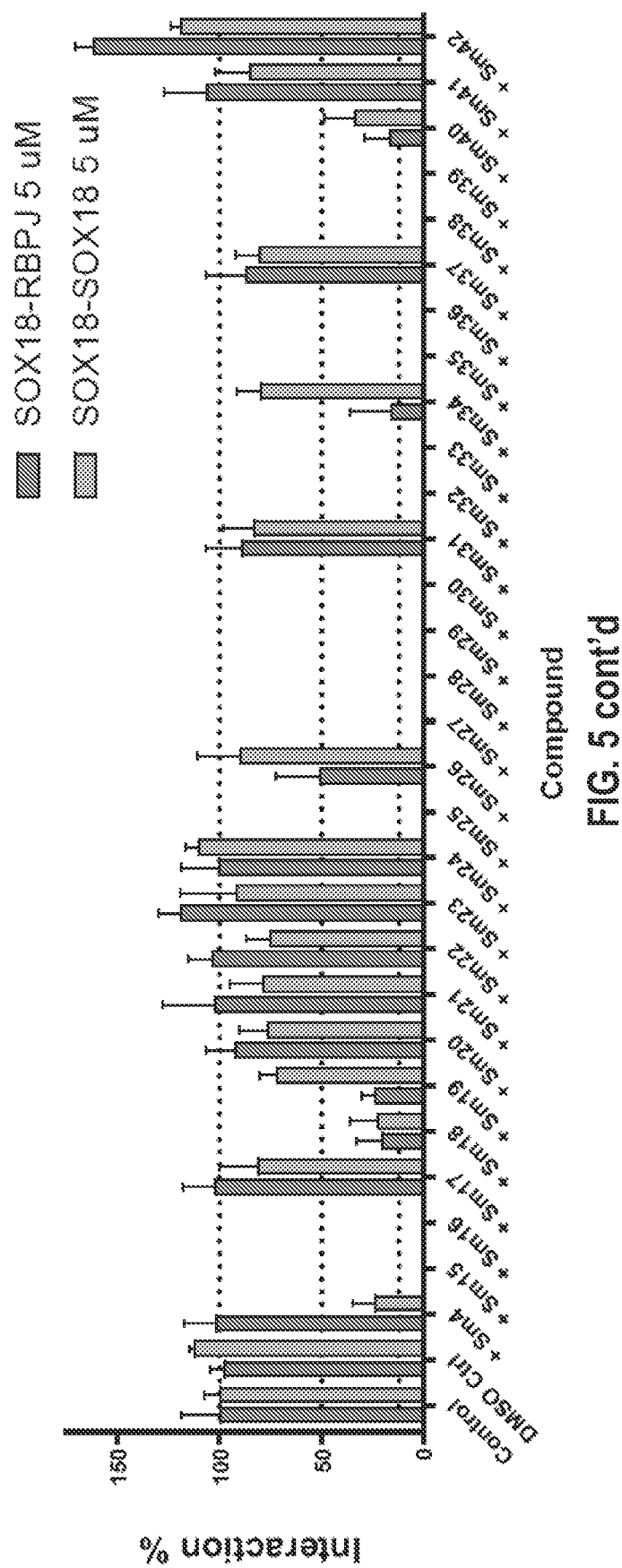

The structure-activity relationship (SAR) of the salicylic acid type inhibitors of SOX18-DNA binding and SOX18/RBPJ PPI has been investigated in more detail with a separate library of analogues. This library was designed to query the significance of some of Sm4 and other salicylates distinctive features, including: electron density of the salicylate aromatic ring, significance of the two acidic hydrogen of the ß hydroxyl carboxylic acid motif, saturated- or ethylene-linkage with lipophilic tail, as well as structure and lipophilicity of the lipophilic tail. We synthesized 30 analogues, Sm15-Sm44 (FIG. 5), which were screened for inhibition of DNA binding to the HMG only SOX18[109] fragment and disruption of SOX18-RBPJ interaction (upper and lower panels). Additionally, a number of these analogues (i.e., Sm4, Sm17 to Sm24, Sm26, Sm31, Sm34, Sm37 and Sm40 to Sm42) were also tested for disruption of SOX18-SOX18 homodimerization interactions using the aforementioned ALPHAScreen assay. As shown in FIG. 5, Sm4, Sm17 to Sm23, Sm26, Sm31, Sm34, Sm 37, Sm40 and Sm41 demonstrated some inhibitory activity in respect of SOX18-SOX18 homodimerization at a concentration of 5 uM. This library was also screened for general cytotoxicity against two cell lines, HEK293 and HepG2, to evaluate their development potential (Table 3).

Potential PAINS (Pan Assay Interference Compounds) chemical moieties, common in promiscuous frequent hitters, which act as false positives in many biochemical high throughput screens, were analysed using the in silico predictor "FAF-Drugs3" (http://fafdrugs3.mti.univ-paris-diderot.fr/) (Baell and Holloway, 2010, Lagorce et al., 2008). In total only 3 compounds were flagged with PAINS moiety (Sm14, Sm40 and Sm44). Sm14 contains a methylene-thiazolone motif, or reactive α,β-unsaturated carbonyl group, while both Sm40 and Sm44 contain a oxidative labile catechol group (Table 2). While Sm40 and Sm44 were not active in the FP assay, Sm14 was not pursued beyond the binding assays. In addition, the new library was analysed for potential aggregators using the "Aggregator Advisor" database, however none showed similarity to known aggregator and all showed moderate lipophilicity, with log P values below 5.8 (Table 3).

SAR for SOX18-DNA binding inhibition. Activity data display some clear SAR for SOX18-DNA binding inhibition, with a reduction or elimination of activity by any etherification, esterification or amidification of both or either one of ß hydroxyl or carboxylic acid. Interestingly, replacement of the carboxylic acid with hydroxyl is tolerated, even though it reduces the inhibitory activity of the compounds. Similarly, salicylic acids para-substituted with small electron donating groups are tolerated displaying similar activity; however, the reduced acidity seems to increase cytotoxicity. For the aromatic tail, replacing the naphtyl with a phenyl (Sm22) completely eliminated all activity. From this small library, only Sm20, an unsaturated analogue of Sm4, displayed SOX18-DNA binding inhibiting activity and low cytotoxicity, similar to Sm4 (FIG. 5).

SAR for SOX18-RBPJ protein-protein binding inhibition. Analogues were first tested at 50 µM. Compounds displaying more than 50% inhibition were then retested at a lower 5 µM. Activities are compared to control levels of SOX18-RBPJ in presence of vehicle solvent with or without lead compound Sm4, also tested at both concentrations. As expected from IC50 plot depicted in FIG. 4B (Top Right Panel), inhibition by Sm4 at 50 µM is almost complete (11.9±5.6%, FIG. 5, Bottom Panel) and marginal at 5 µM. At high concentration of 50 µM, half of all tested compounds displayed strong activity, however, only Sm18, Sm19, Sm26, Sm34 and Sm40 remained highly active at 5 µM, with Sm26 remaining moderately active. Interestingly, none of these five potent PPi inhibitors, inhibit protein-DNA binding as well.

The pattern in the inhibition of SOX18-RBPJ protein-protein interaction is less clear as in the inhibition of SOX18-DNA interaction. Several of the compounds containing the vinyl naphthalene are active in PPI inhibition; it is however, unclear whether the activity is due to increase rigidity of the linker or due to the reactivity of the vinyl-aromatic group as Michael acceptor. A distinct feature of this library is that the free carboxylate is not required for PPI activity, as di-ethyl amides or poly hydroxyl/methoxy containing compounds show PPI inhibition at 50 µM, however no inhibition of the DNA binding. Lastly, there is little overlap between PPI and DNA-binding inhibition, with the exception of Sm4 and Sm20, which inhibit both DNA and PPI.

Structural Investigation

The three-dimensional structure of mouse SOX18-HMG domain bound to DNA harbouring a SOX motif has been recently resolved by X-ray crystallography (Klaus et al., 2016), showing high similarity to other HMG domains. However, attempts to co-crystallize SOX18 HMG domain bound to DNA in presence of Sm4 failed to identify a binding pocket for the inhibitor, as no electron density for the inhibitor could be detected. This was likely due to the protein/DNA disruption properties of Sm4. To evaluate possible binding sites for Sm4, we used in silico docking and molecular dynamics calculation, using the SOX18/DNA crystal structure. In the absence of a defined binding pocket in the SOX18-HMG domain, the in silico docking produced several possible binding poses, which were further validated by molecular dynamics (MD) simulations. These simulations identified one binding pose that remained stable during the entire simulation time of 200 ns. In comparison, in all other poses the inhibitor broke its protein interaction after 3 to 14 ns, remaining in the surrounding solvent without protein contact. Similarly, no stable Sm4 binding poses were found using the SOX18-HMG structure without DNA.

Figure 6:
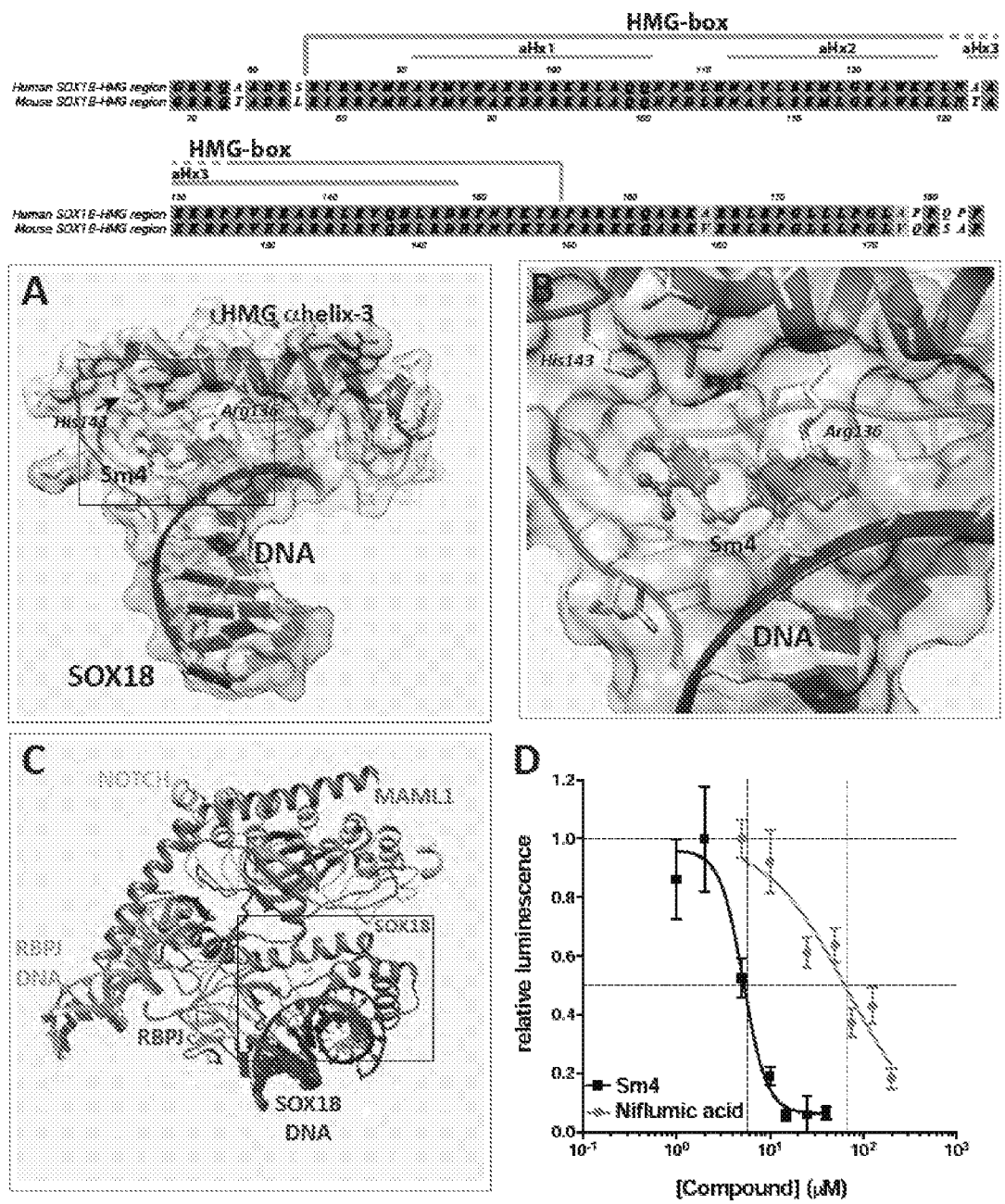
FIG. 6: In silico modelling of Sm4 at the interface between SOX18-HMG and RBPJ. Inhibition of SOX18-dependent transactivation in vitro. A., B. Stable binding pose for Sm4 in the SOX18/Prox1 DNA X-ray crystal structure, putting the inhibitor in an 'open' pocket between protein and DNA. C. Docking of the SOX18/DNA structure into the structure of the Notch transcription complex. D. Luciferase reporter assay in COS7 cells transiently transfected with Sox18 and a vector containing Vcam1 promoter merged to firefly luciferase gene (Hosking et al., 2004). Cells were treated with small molecules at concentration below CC10 (10% cytotoxicity) for 24 hours in culture medium containing a maximum of 1% DMSO (v/v). Results are depicted for Sm4 and niflumic acid. Meclofenamic and flufenamic acids were inactive at concentrations below CC10.
Figure 7:
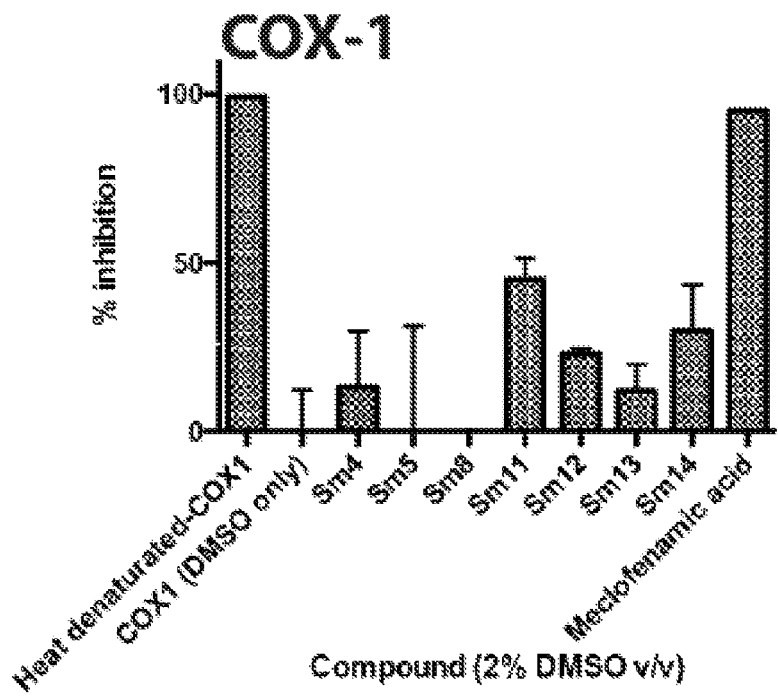
FIG. 7: COX-1/2 enzyme inhibition. Inhibition of COX-1 and COX-2 enzyme by SOX18 inhibitors, including meclofenamic acid as positive control. Inhibition of COX enzyme is measured by the amount of $PGH_2$ prostanoid produced from arachidonic acid conversion.
Figure 7:
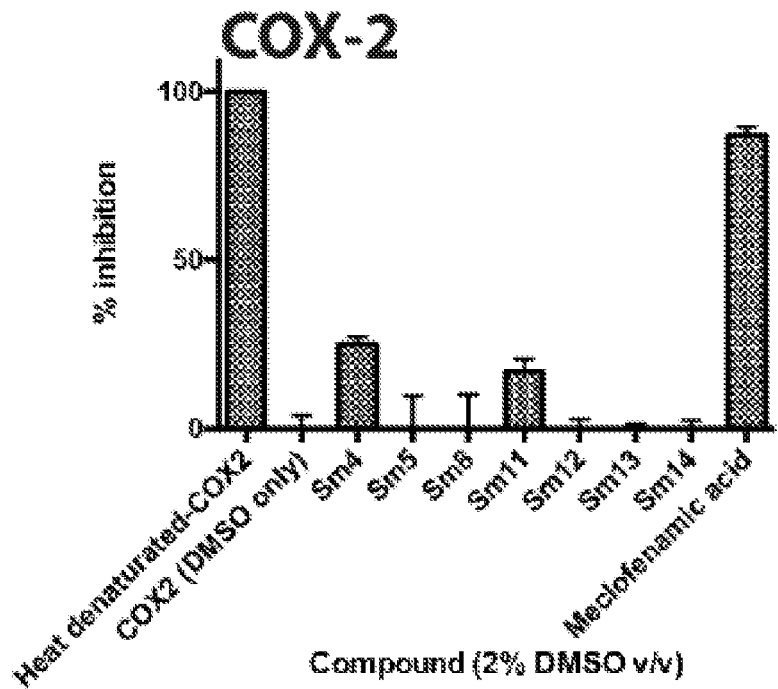
Figure 8:
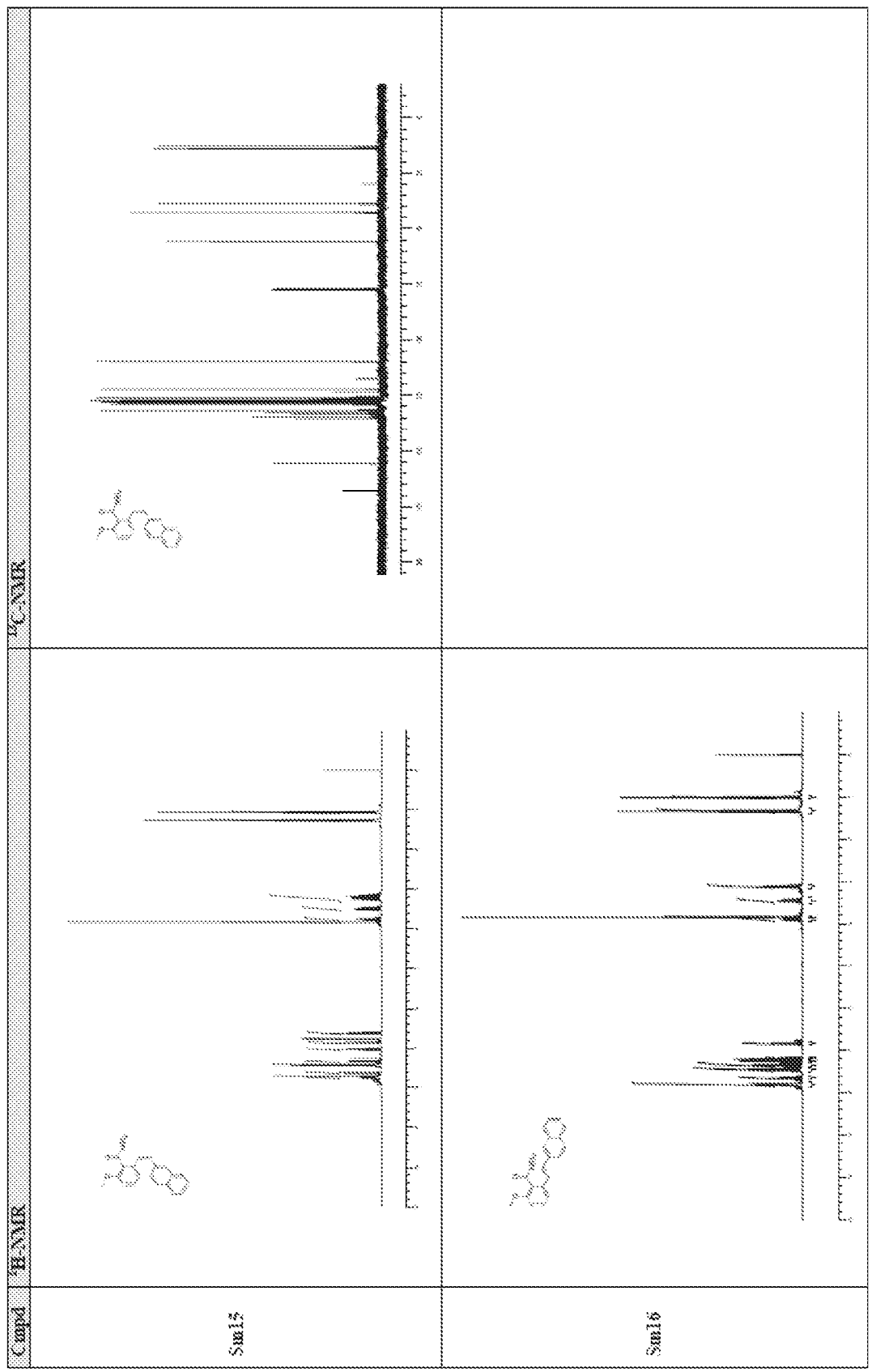
FIG. 8: NMR spectra of Sm14-44.
Figure 8:
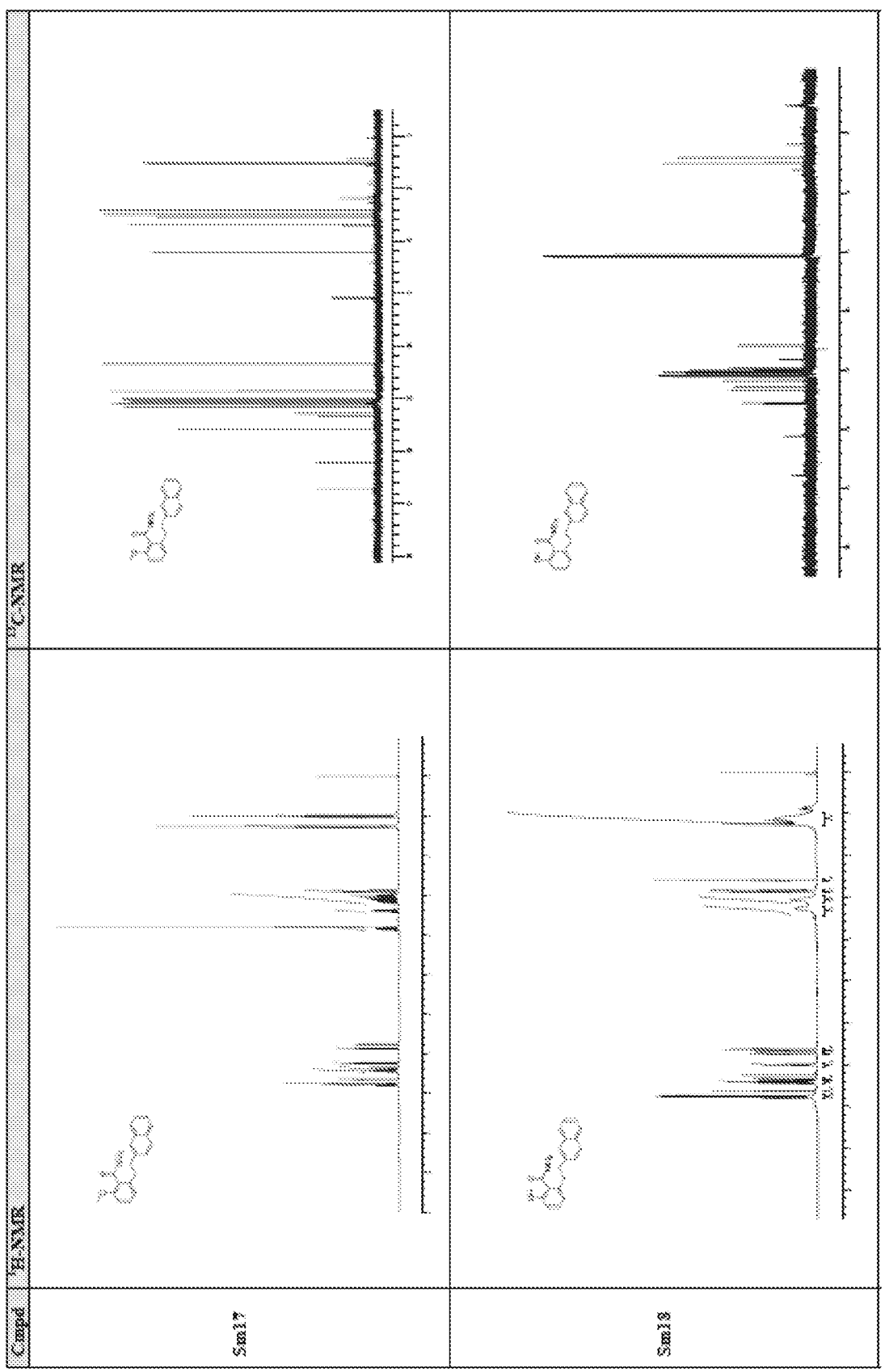
Figure 8:
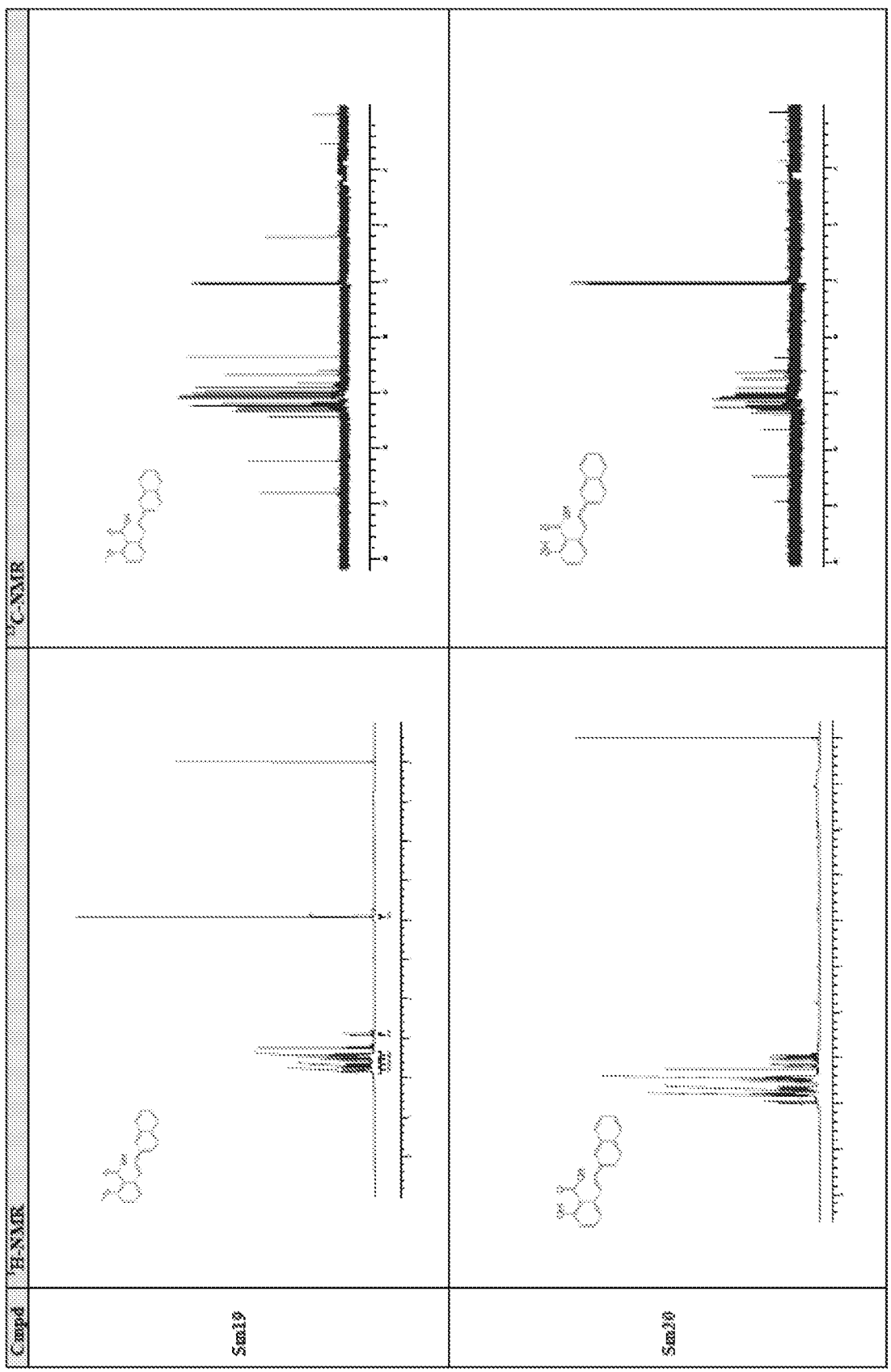
Figure 8:
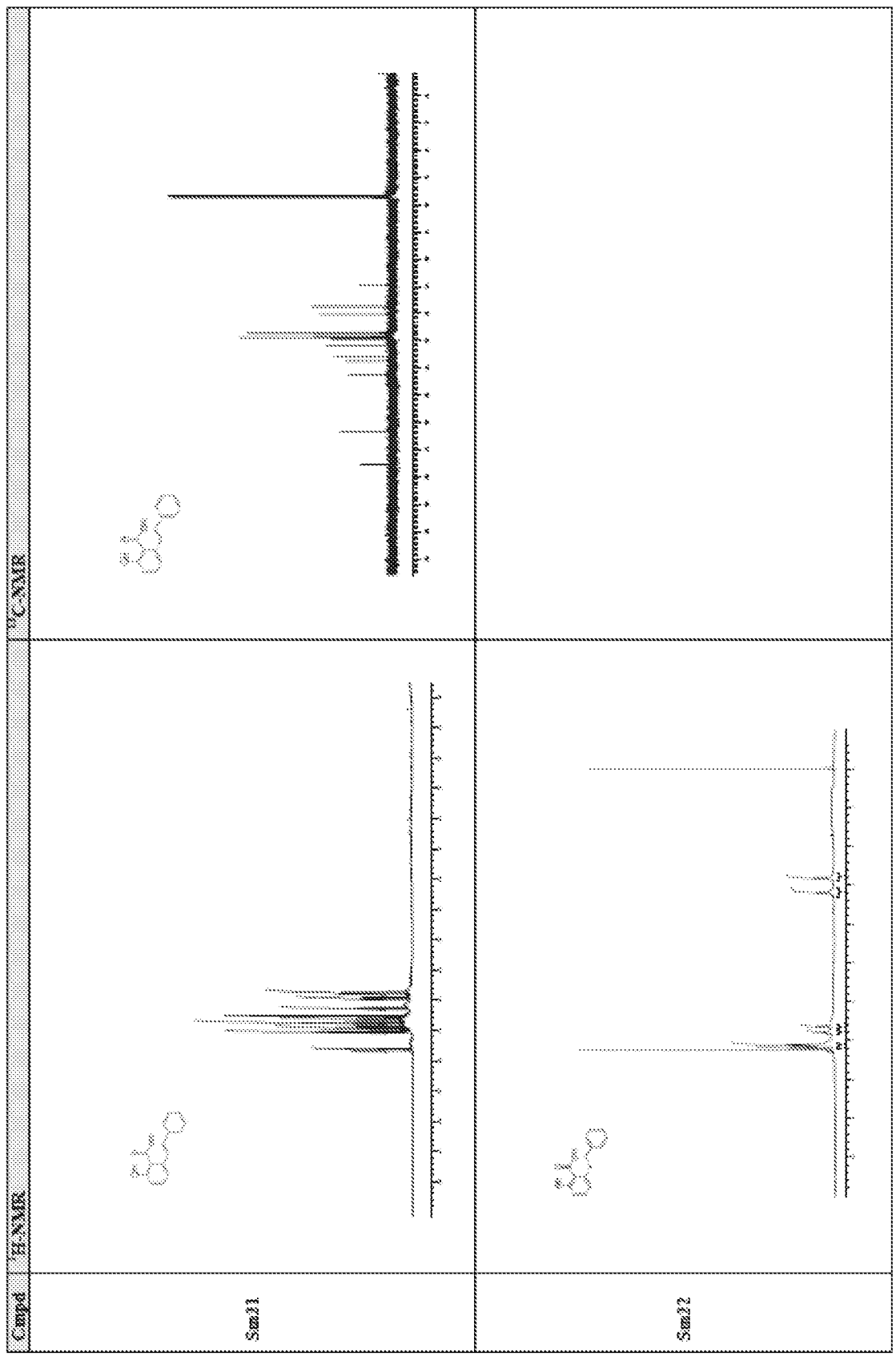
Figure 8:
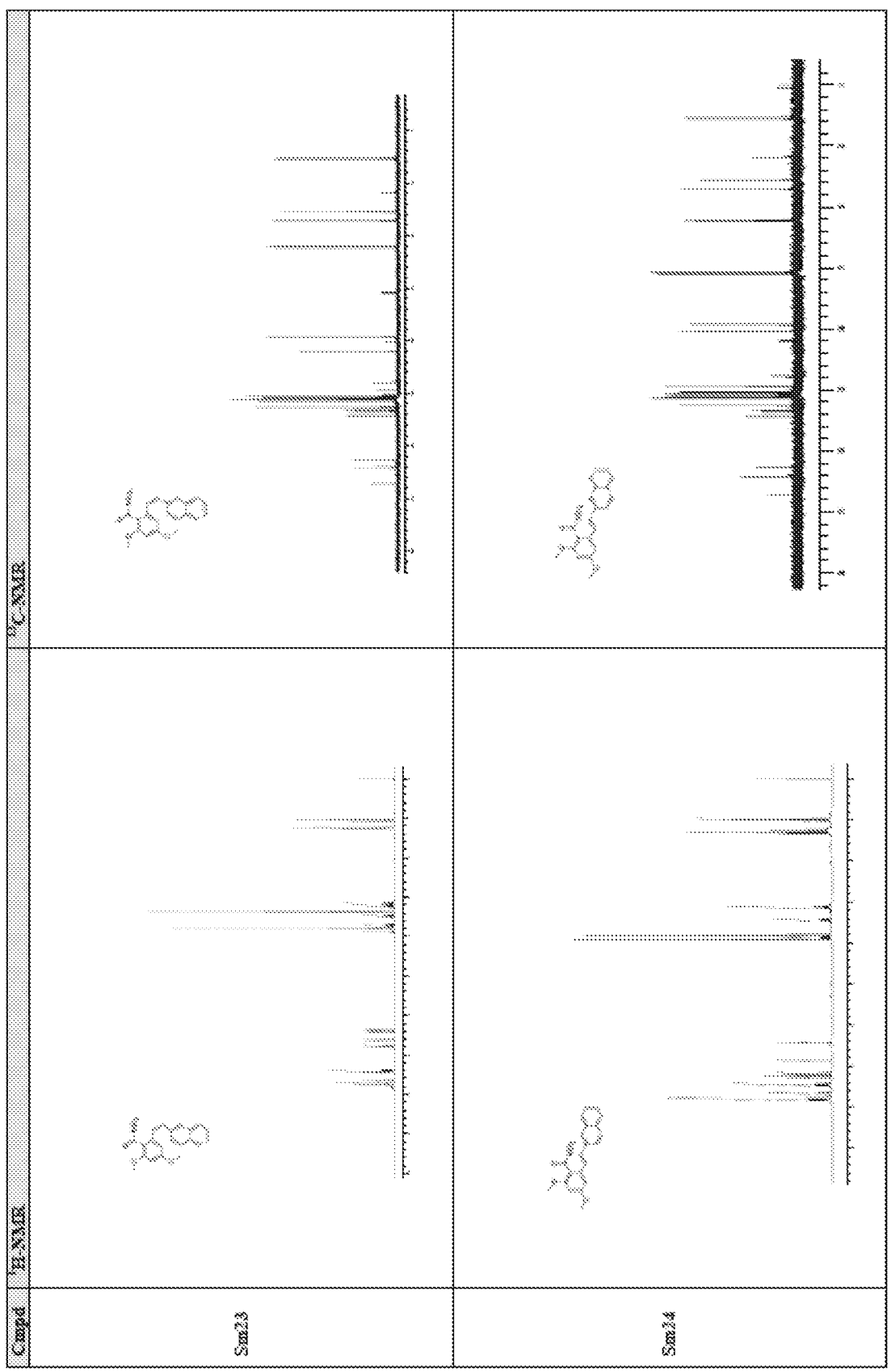
Figure 8:
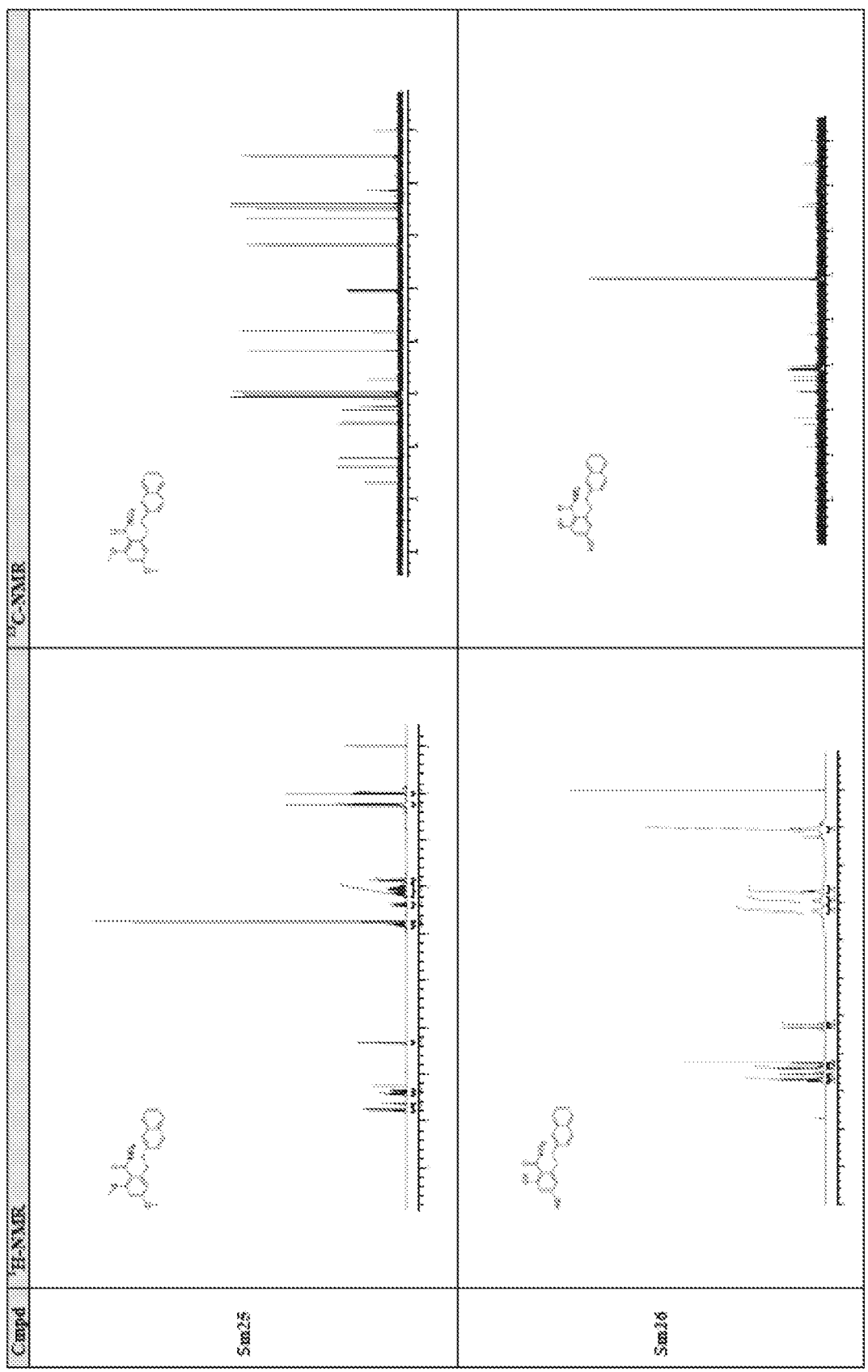
Figure 8:
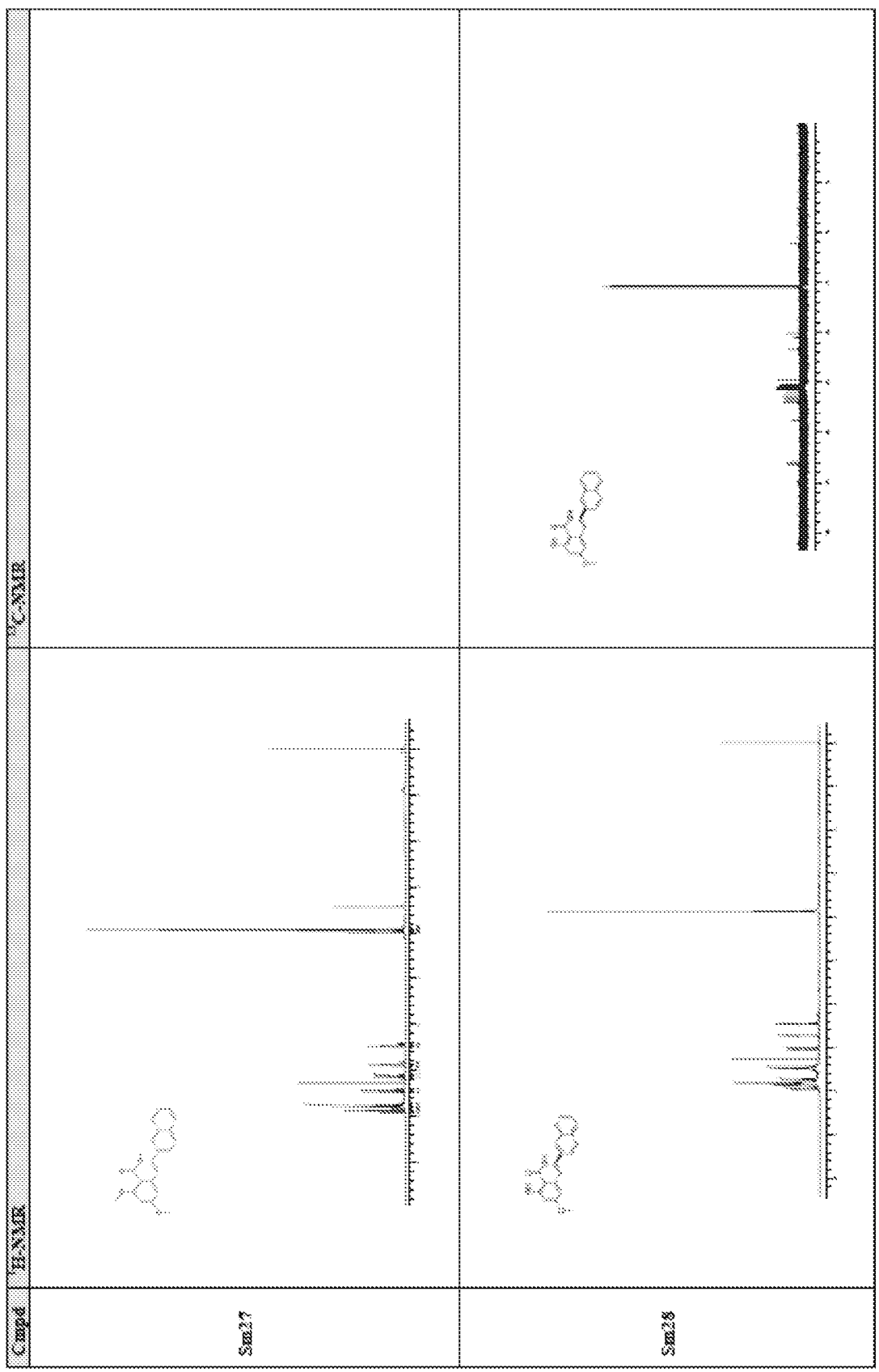
Figure 8:
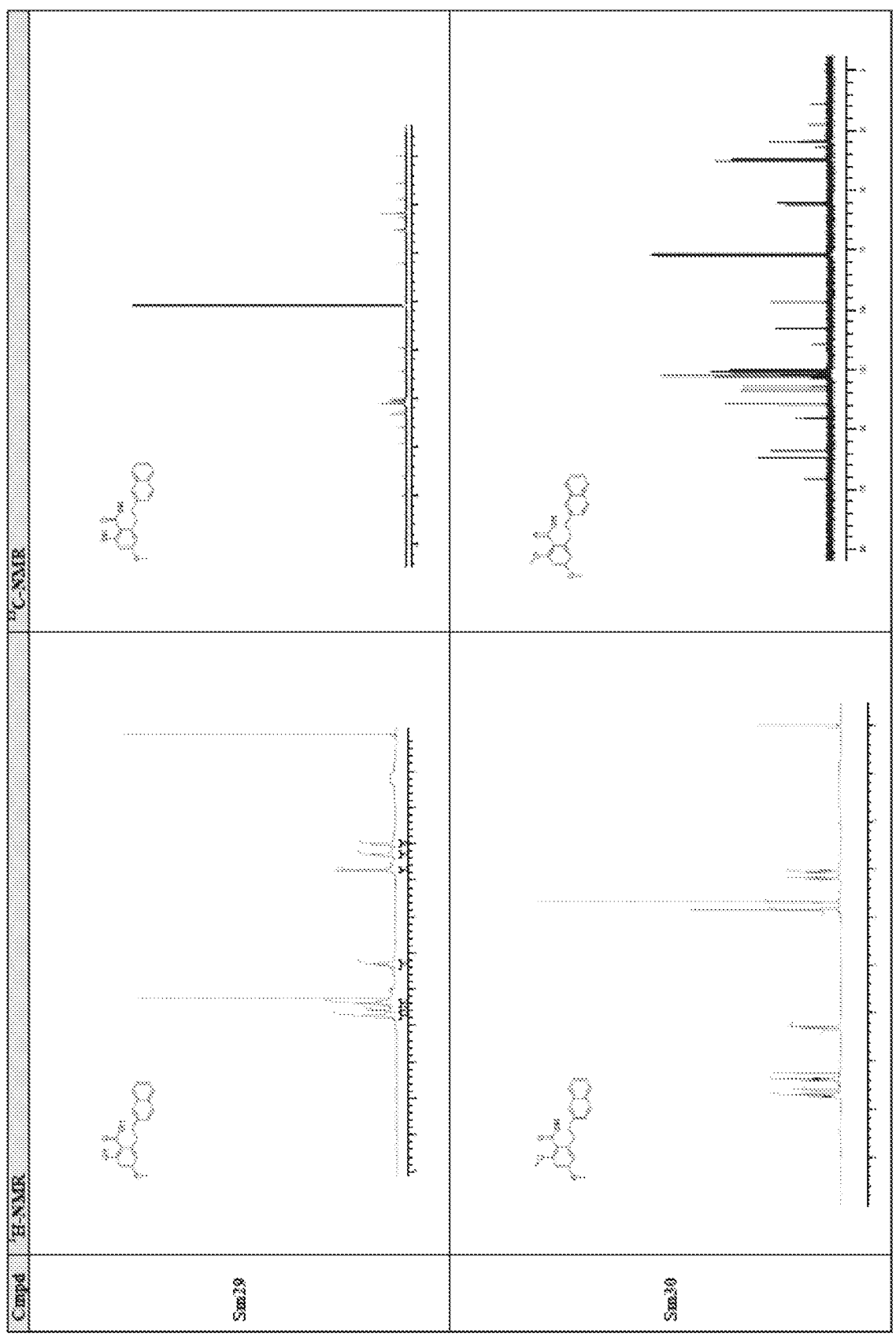
Figure 8:
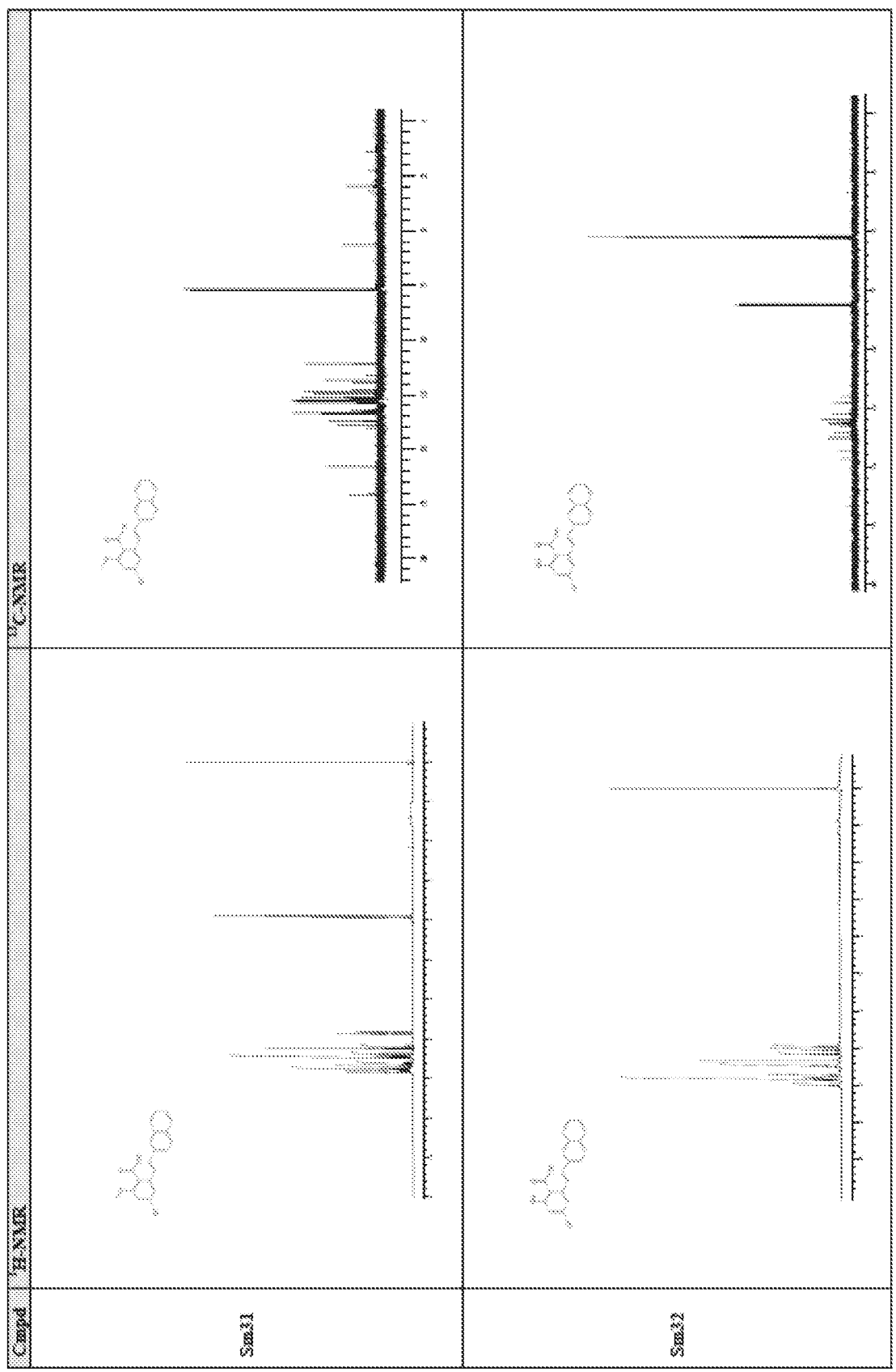
Figure 8:
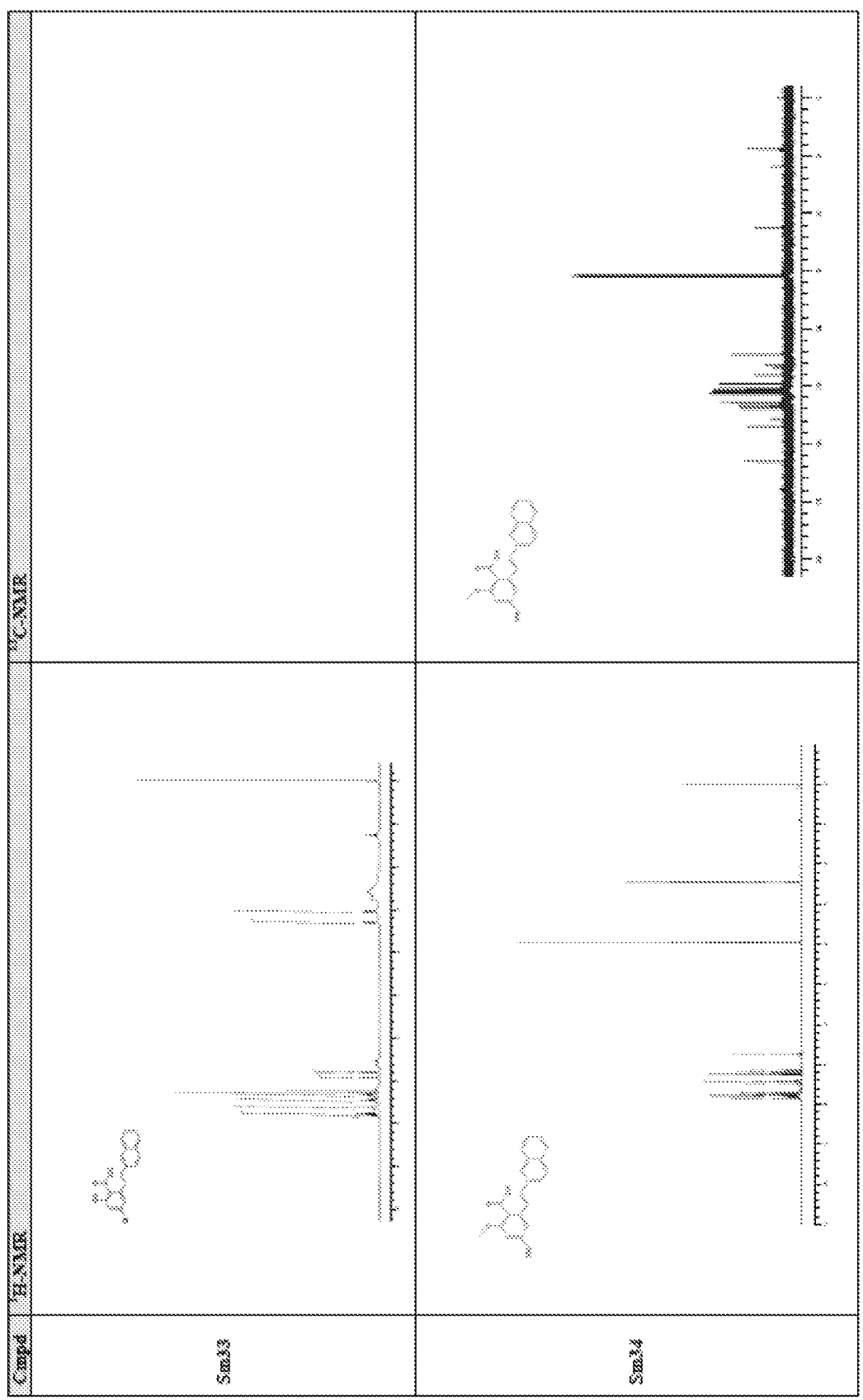
Figure 8:
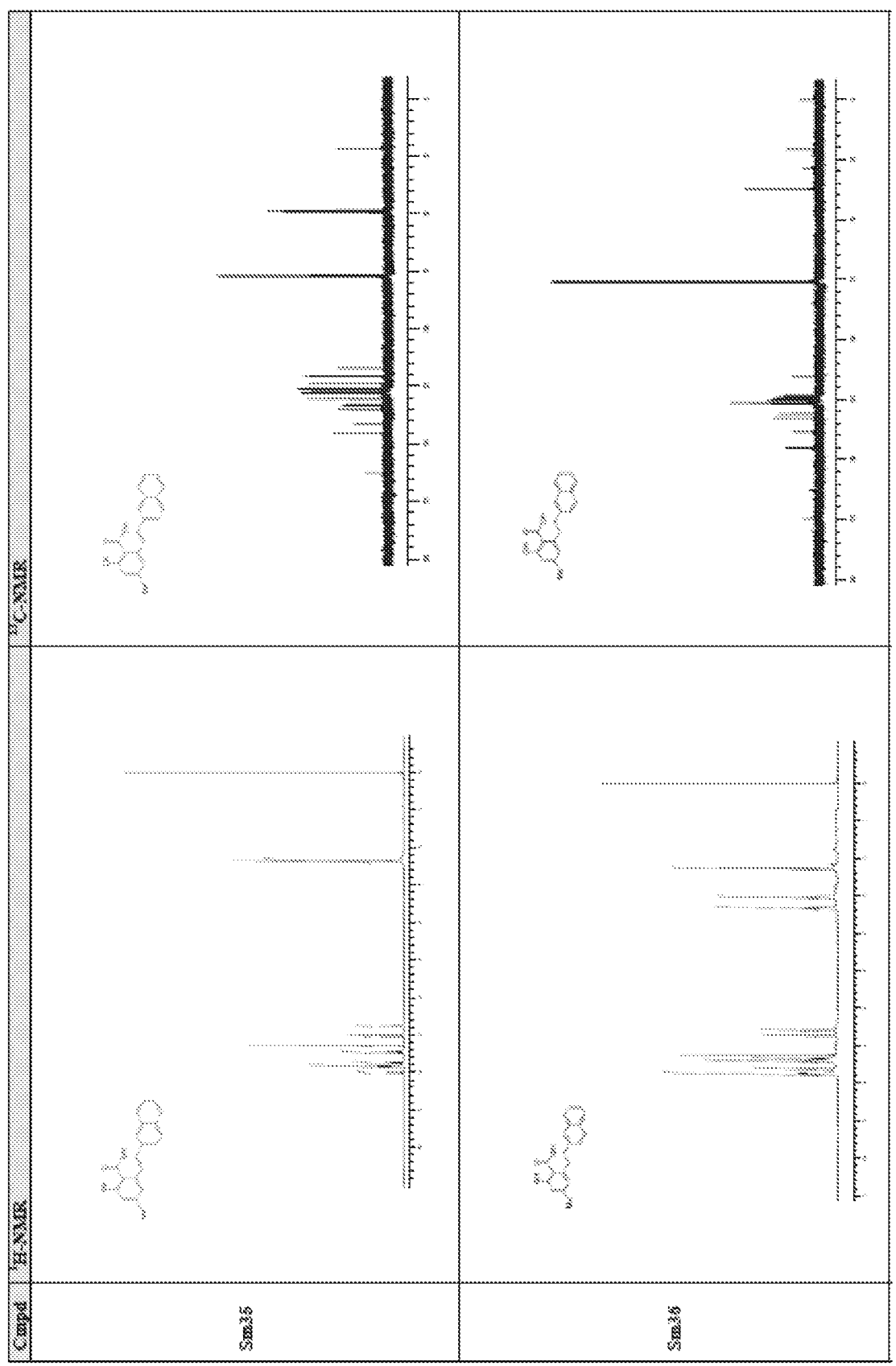
Figure 8:
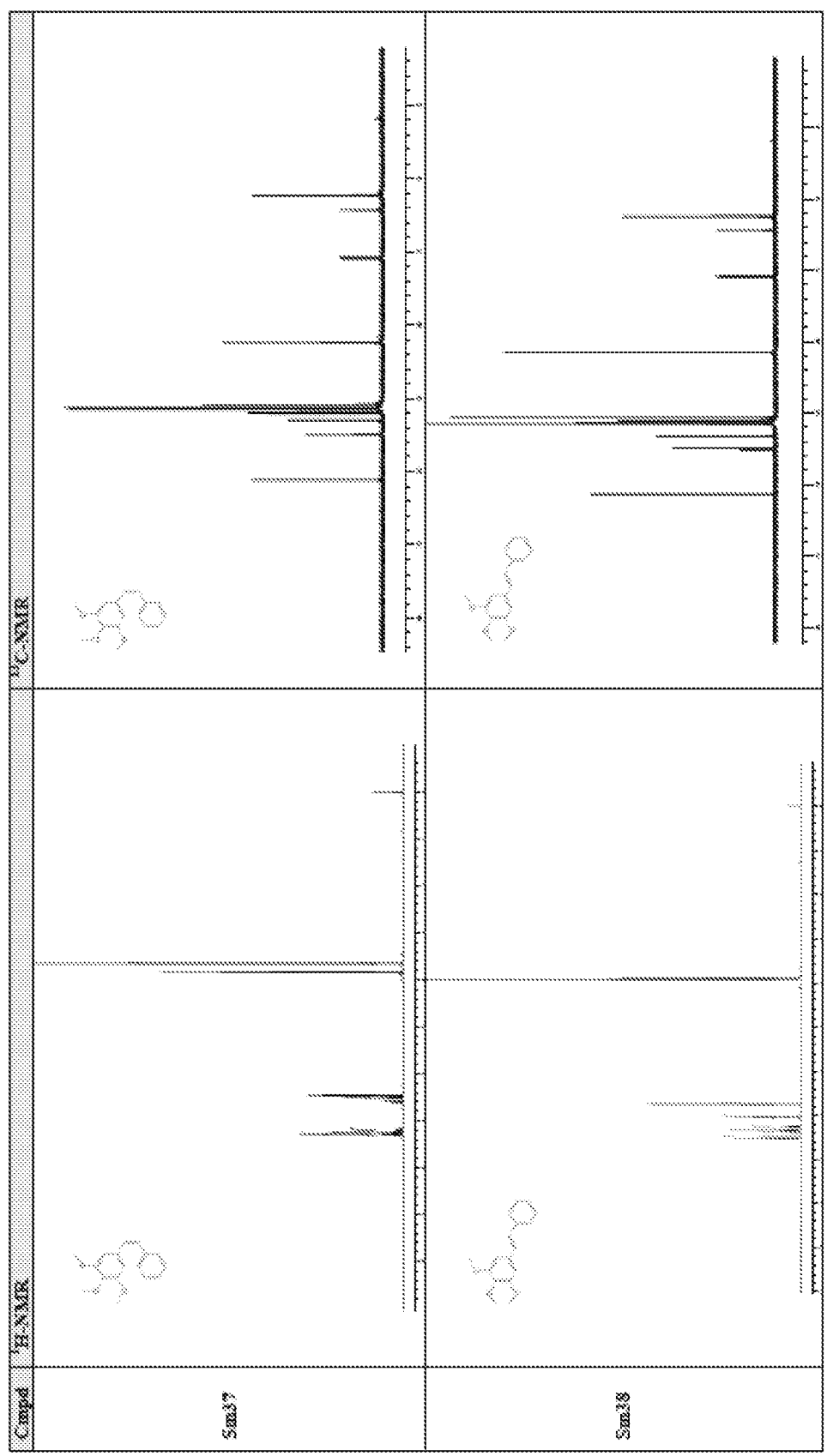
Figure 8:
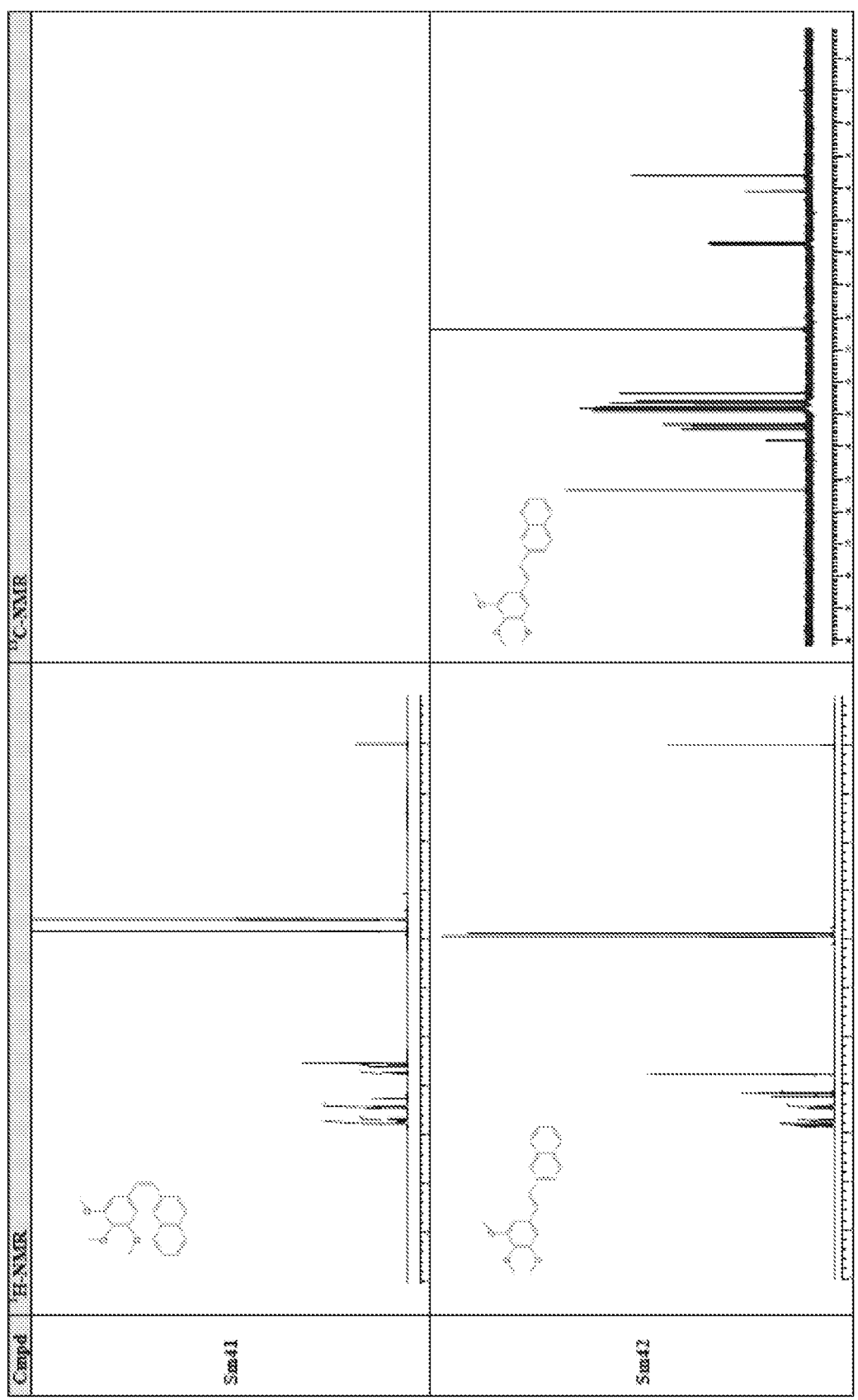
Figure 8:
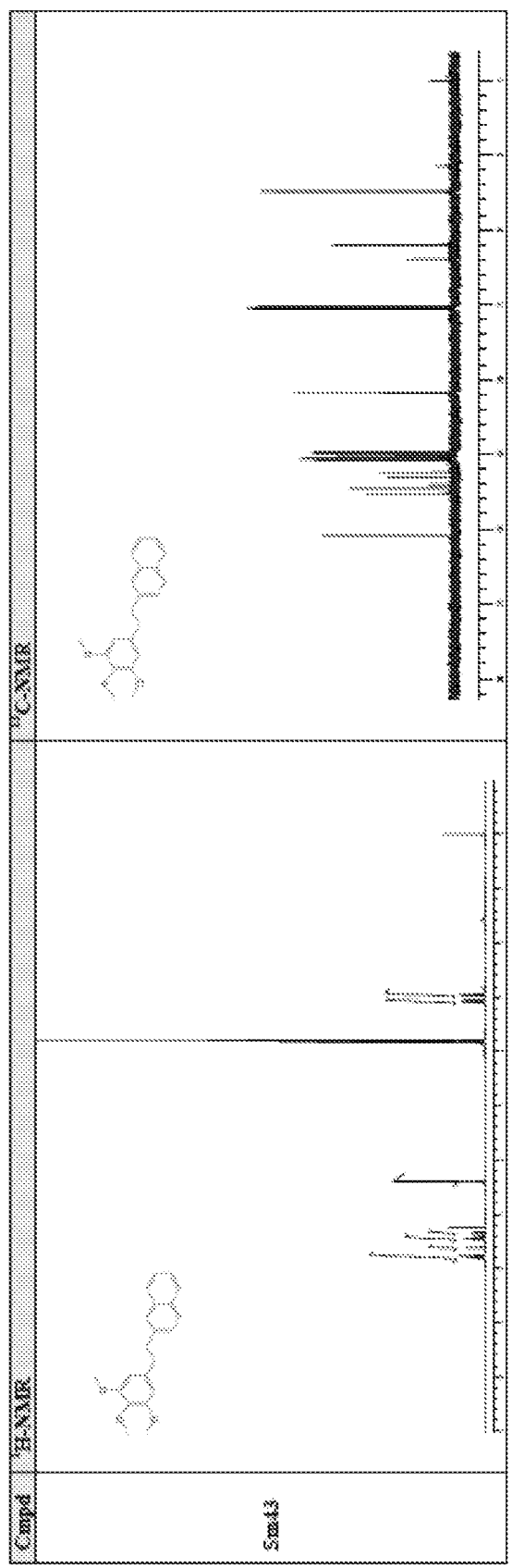

The stable binding pose for Sm4 in the SOX18/DNA structure puts the inhibitor in a solvent accessible pocket between protein and DNA that is otherwise occupied by water molecules in the X-ray crystal structure. Sm4 main polar interactions are with Arg136 and Lys147, which swaps its interaction with dG15, and with some induced conformational changes to His143, rotating its side chain towards Sm4 (FIG. 6A, B). However, no other major conformational changes could be observed that would directly explain Sm4's mode of DNA binding inhibition.

To investigate possible protein-protein interaction sites of SOX18, we used in silico protein-protein docking, in combination with MD simulations, to build a complex model of SOX18/DNA with its protein partner RBPJ. For RBPJ we used the X-ray crystal structure of a section of the human Notch transcription complex, elucidated in 2012 (Choi et al., 2012). This section contains the ankyrin (ANK) repeat domain, the RBPJ-J-associated molecule (RAM) domain of the Notch intracellular domain, bound to coactivator MAML1, as well as the transcription factor RBPJ bound to its consensus DNA. Docking the SOX18/DNA structure into the structure of this Notch transcription complex with subsequent MD simulation for optimization, resulted in a complex model shown in FIG. 6C. This model indicates that RBPJ/SOX18 complex can be mediated by the HMG domain and is able to form a protein complex with no interference by both DNA molecules. Indeed, both DNA strands, from RBPJ and SOX18, are orientated nearly parallel to each other, similar to the DNA orientation on a nucleosome. In addition, both C and N-terminal tails of the HMG domain are orientated towards the solvent, allowing addition of the missing SOX18 domains without immediate interference with the RBPJ complex.

The interaction between SOX18 and RBPJ is provided by the C-terminal part of helix 3 and residues from the C-terminal tail (residues Gln138, Arg141, Asp142 and His143) of the HMG domain. This protein-protein interface is thereby opposite to the DNA-binding interface of that region. Mapping the putative binding site of Sm4 onto the RBPJ/SOX18 complex positions the inhibitor right into SOX18 DNA-binding region of helix-3 and C-terminal tail, opposite its main protein-protein interface, suggesting the possibility that binding of Sm4 could perturb both protein-protein and protein-DNA interactions.

Modulation of SOX18 Transcriptional Activity

To further assess the functional effects of the SOX18 inhibitors, we used an in vitro cell-based reporter system, as a readout of SOX18 transcriptional activity. COS-7 cells were transfected with constructs containing a Vcam-1 promoter fragment fused to a luciferase reporter gene and a SOX18 expression vector. Sm4, our lead compound in term of PPI disruption specificity was tested in this cell-based assay, along with meclofenamic, niflumic and flufenamic acids. Of these four small molecules, Sm4 displayed the most effective inhibition of SOX18 transcriptional activity, with an IC50 value of 5.2 µM (FIG. 6D). Meclofenamic acid and flufenamic acid cytotoxicity was reached before any concentration-dependent SOX18 inhibition could be observed. All other tested compounds displayed lower potency (20 µM<IC50<50 µM, Table 1, column 3).

The observation that Sm4 selectively perturbs a particular PPI in a concentration range similar to the one required to inhibit its transcriptional activity in vitro suggests that the mode of action of this small compound is likely to be via interference with protein partner recruitment.

Assessing SOX18 target engagement by SM4 using Single Molecule Tracking (SMT). SMT technology enables us to visualize in real time in live cell nuclei the search pattern of the SOX18 protein for its target genes on chromatin at a single molecule of resolution. The fact that it is possible to visualize SM4 perturbation on SOX18 chromatin binding dynamics is a clear demonstration of SM4 on-target engagement. This effect is observed at concentrations devoid of any cytotoxicity. The effect of SM4 causes SOX18 to dwell longer on the chromatin at specific sites, this change in the protein dynamics is likely to be the consequence of changes in SOX18 protein-protein interaction which is impaired by SM4 (as shown previously by the ALPHAScreen assay). Transcription factor mode of action is driven by a code of protein-protein interaction that instructs gene target selectivity. If this code is altered the transcription factor activity is invalidated.

DISCUSSION

Transcription factors are proteins that have a DNA-binding domain, multiple protein partners, and in some cases even an endogenous ligand. The notion that TFs rely on this type of interactions for their activity opens up different avenues for the discovery of molecules modulating their function, such as screening for protein-DNA or protein-protein interaction inhibitors. While there is a wealth of information on the genetic pathways in which TF are involved, little is reported on their molecular mode of action, and more particularly, on the recruitment of multiple protein partners. Hence, screening for DNA binding inhibitors has, until recently, provided the main option to find TF modulators, even though DNA-binding domains are highly conserved within TF families and constitute a region with low potential for selectivity.

In this study, we used a high-throughput DNA-binding assay to screen a chemically diverse natural products library, identifying compounds able to inhibit the DNA-binding of transcription factor SOX18. The screening identified two compounds of similar structure, both with a salicylic acid core and a lipophilic tail. A focused library designed around the two active compounds identified a wider range of similar compounds, with varying degrees of activity, proving that the compounds form a cluster of SOX18 DNA-binding inhibitors. With the focused library, we further demonstrated that the inhibitory activity was due to binding of the small compounds to the protein and not to the DNA itself. The active molecules interact with the SOX18 protein, increasing its thermal stability upon binding. In addition, using either SOX18 full length or HMG box-only proteins, we proved that the compounds interact directly with the DNA-binding domain or in its immediate vicinity.

We argued previously that using disruption of DNA-binding as a filter would yield compounds with low selectivity between SOX transcription factors due to a high level of sequence conservation of the HMG-box. In agreement with this, our lead compound, Sm4, was able to disrupt the DNA binding activity of a wide range of HMG-box from various SOX proteins when used at high concentration (200-300 µM). The HMG box of SOX proteins consists of three α-helices, with two providing the main interface for DNA-binding. However, SOX9 HMG box has been reported to be involved in protein-protein interaction as well (Huang et al., 2015, Agresti and Bianchi, 2003, Prokop et al., 2012), with the third α-helix proposed as the main interface for the partner proteins. In this study, we applied an in vitro method of protein-protein interaction (PPI) detection to investigate the disruption of TF protein partner recruitment. Direct protein-protein interaction for transcription factor SOX18 has only been reported for MEF2C (Hosking et al., 2001), while a genetic interaction with RBPJ has only been shown in the transactivation of Dll4 gene (Sacilotto et al., 2013). Both proteins display direct binding to SOX18 in the Cell-free/ALPHAScreen and Co-IP assay. Importantly, some of the small molecules differentially disrupt specific PPIs. Sm4 with a salicylic acid scaffold is, thereby, more selective in disrupting the SOX18/RBPJ complex, whereas flufenamic acid with an anthranilic acid scaffold is more selective for the SOX18/MEF2C complex. Further, in silico docking provides a putative binding pocket for Sm4, close to the C-terminal tail of the HMG box, wedged in between DNA and the third helix of the protein. This location suggests that an inhibitor like Sm4 would be able to alter the conformation of the SOX18 protein to not only affect DNA binding, but also the interaction surfaces with protein partner such as RBPJ.

Further investigation of the effect of small compounds on SOX18 transcriptional activity, revealed that Sm4 is able to block SOX18-dependent Vcam-1 promoter activity, when fused to a luciferase reporter gene. Flufenamic acid displays only little effect on SOX18 transcriptional blockade. This reporter assay was conducted in COS-7 cells that were transfected with both Sox18 and luciferase expression vectors, hence limiting the interpretation of a potential disruption of SOX18 endogenous partner recruitment. Nevertheless, the inhibition of SOX18 regulated transcription by Sm4 is a clear indicator that a small molecule can interfere with a transcription factor activity in a cell-based environment.

Synthesis and screening of an extended library further indicated some clear structure-activity relationships for inhibiting the SOX18/DNA binding. While some degree of variation is tolerated in the lipophilic tail and its linker, both hydroxyl or carboxylic acid groups have to retain their hydrogen-bond donating capabilities, as any esters, ethers or amides abolish the activity. Variation of the carboxylic acids with para substituted electron donating groups has little effect, as does the replacement of the acid with hydroxyl (resorcinol scaffold), both retaining their ability to inhibit SOX18 DNA binding. Compounds with an anthranilic acid scaffold were selected as an extension of the chemical similarity of the salicylic acid scaffold to NSAID compounds. While the study showed that, SOX18 inhibitors have no inhibitory activity against COX1 or COX2, some NSAID compounds display SOX18 DNA binding inhibition. However, difference in SOX18-protein binding inhibition (SOX18-MEF2C inhibition instead of SOX18-RBPJ) suggests a different mode of binding or action.

The efficacy of a compound to inhibit the transcriptional activity of a TF depends on the concentration of both TF and compound in the nucleus. The concentration of TFs can reach almost millimolar levels in the nucleus (Chen et al., 2014), while compound concentration depends on its ability to partition through both cell and nucleus membranes. For initial drug discovery it is more informative (i.e. to build SAR models) to measure the IC50 in homogenous assay, where the compound concentration is defined. However, for further drug optimisation the penetration of the compound into the nucleus needs to be considered as well, either with predictive models or with cell-based assays, measuring the effective inhibition concentration (IC50) of compounds.

The other consideration to be made when developing TF inhibitors is which PPIs are predominately affected by the compound. Protein-protein interactions, including interaction between TFs, are relatively weak. For example, the interaction between p32 and HDM2 has a KD in the low to mid micromolar range (Dawson et al., 2003, Chen et al., 2013). In comparison, antibody-antigen interactions or interactions between endogenous peptide ligand and receptors (e.g. EGF-EGFR) are much stronger, with KD in the low nanomolar to high picomolar range (Mian et al., 1991, Lax et al., 1988). Similarly, interactions between protein and DNA are in the low nanomolar range, mostly due to strong electrostatic interactions between negatively charged DNA and a usually positively charged DNA-binding domain. Sm4 is able to inhibit both SOX18/DNA and SOX18/RBPJ interactions, however, the inhibitory effect is greater on the weaker PPI.

An important consideration in the development of TF inhibitors is the ability to selectively inhibit PPI, especially since TFs are capable of recruiting half a dozen different protein partners (Gamper and Roeder, 2008). Even though TFs are intrinsically disordered (Wright and Dyson, 2015), these proteins display domains modularity for different protein-protein interfaces (Reichmann et al., 2005). This implies that some interactions share structural similarities, while activating different downstream pathways. Similar to other regulatory proteins and enzymes, such as kinases, the selectivity profile of TF protein-protein inhibition needs to be considered. While blockade of all PPIs might not be desirable, maximum efficacy might not be achieved with single PPI inhibition, but by simultaneously inhibiting the recruitment of a subset of selected protein partners.

In conclusion this study identified salicylic acid derivatives as a major pharmacophore for SOX18 inhibition, and Sm4 as a lead compound. Future drug-optimization should be performed following cues from both protein-DNA binding and PPI assays to further refine selectivity and potency.

TABLE 1

Focused library compounds ability to inhibit SOX18-DNA binding and SOX18-dependent transactivation in vitro.

| Compound | FP $IC_{50}$ = SD μM | CMC μM | In vitro efficacy in cell $IC_{50}$ = SD μM CO57(Luc) | In vitro cytotoxicity $CC_{50}$ = SD μM CO57 | Aggregator advisor logP |
|---|---|---|---|---|---|
| Natural products | | | | | |
| Sm1 | 348 ± 1.1 | — | — | — | 6.8[#] |
| Sm2 | 341 ± 1.1 | — | — | — | 7.8[#] |
| Salicylic acid analogues | | | | | |
| Sm3 | — | 30 | — | — | 6.1[#] |
| Sm4 | 97.5 ± 1 | >1000 | 5.2 ± 1.1 | 117 ± 29.4 | 4.6[#] |
| Sm5 | 1,105 ± 1 | >1000 | 21 ± 14 | >200 | 3.2[#] |
| Sm6 | — | 20 | — | — | 6.1[#] |
| Sm7 | — | 20 | — | — | 6.3[#] |
| Sm8 | 327 ± 1.1 | >1000 | ~50 | >200 | 5.5[#] |
| Sm9 | — | 20 | — | — | 4.8[#] |
| Sm10 | — | 20 | — | — | 6.1[#] |
| Resorcinol analogues | | | | | |
| Sm11 | 3,803 ± 1 | >1000 | ~50 | >200 | 2.6[*] |
| Sm12 | 2,880 ± 1.1 | >1000 | 33 ± 3.7 | 98.6 ± 17.4 | 3.8[*] |
| Sm13 | 481 ± 1.1 | >1000 | ~30 | >200 | 3.2[#] |
| Sm14 | 120 ± 1.1 | >1000 | 25 ± 9 | >200 | No aggregation |
| NSAID analogues | | | | | |
| Salicylic acid | — | — | — | — | No aggregation |
| Aspirin | — | — | — | — | No aggregation |
| Gentinic acid | — | — | — | — | No aggregation |
| Meclofenamic acid | 163 ± 17.7 | — | >>$CC_{10}$ | 16 ± 0.3 | 5.6[#] |
| Niflumic acid | 375 ± 84 | — | 58.3 ± 7.6 | >200 | 3.4[#] |
| Flufenamic acid | 220 ± 68.6 | — | >$CC_{10}$ | 65 ± 2.7 | 4.8[#] |

[*]similar to known aggregator
[#]no know aggregators, "high" LogP; possible aggregator With respect to Table 1 above, in the first column, compounds FP IC50 were estimated using variable Hill slope curve fitting. Different concentration ranges were tested in the FP-based DNA binding competition assay (0.2-200 uM, 10-500 uM, 10 uM-3 mM), with DMSO concentrations ranging from 0 to 3.33% v/v. Experiments were performed in three independent replicates. The second column summarizes threshold concentrations at which compounds Sm1-14 start forming micelles in saline (200 mM NaCl) or fluorescence polarization buffer (30 mM HEPES pH 7.5, 100 mM KCl, 40 mM NaCl, 10 mM NH4OAc, 10 mM Guanidinium, 2 mM MgCl2, 0.5 mM EDTA, 0.01% NP-40). The third and fourth columns summarise 50% inhibitory concentration —IC50— of cell-based luciferase SOX18-dependent transactivation as well as cytotoxicity —CC50— for all active compounds, in COS 7 fibroblasts. In the last column, we used "Aggregator Advisor" (Irwin et al., 2015) to predict aggregators, based on physical properties (CLog P>3) and likeness to a 12,600 compound-strong library of known aggregators (*: compound similar to known aggregator, #: not similar to any known aggregator, but possible risk because of "high" Log P.: no predicted risk of aggregation).

TABLE 3

DNA-binding and cytotoxicity
Experimental data for Sm15-Sm44 for inhibition of SOX18/DNA binding (FP) and cytotoxicity against two mammalian cell lines. Also shows the predicted lipophilicity as cLogP.

| Cmpd | FP bound fraction (%) | | Cytotoxicity ($CC_{50}$ μM) | | cLogP |
|------|---|---|---|---|---|
|      | 200 μM | 50 μM | HEK 293 | HepG2 | |
| Sm15 | 120.8 ± 4.7 | 102.6 ± 7.4 | >100 | 59.1 | 5.2 |
| Sm16 | 108.9 ± 4.9 | 99.3 ± 6.2 | >100 | 45.1 | 5.2 |
| Sm17 | 117.0 ± 10.9 | 100.3 ± 6.0 | 62.6 | 38.5 | 4.8 |
| Sm18 | 106.9 ± 21.3 | 98.7 ± 5.0 | 38.7 | 28.0 | 4.7 |
| Sm19 | 107.6 ± 4.5 | 99.2 ± 6.8 | >100 | >100 | 5.0 |
| Sm20 | 11.9 ± 8.5 | 10.3 ± 4.1 | 97.1 | 71.3 | 5.0 |
| Sm21 | 98.1 ± 2.1 | 103.4 ± 8.8 | >100 | >100 | 3.8 |
| Sm22 | 93.1 ± 9.5 | 98.1 ± 6.1 | >100 | >100 | 3.4 |
| Sm23 | 106.4 ± 1.7 | 102.5 ± 9.7 | 36.0 | 20.3 | 5.2 |
| Sm24 | 102.8 ± 16.6 | 97.4 ± 9.0 | 30.6 | 36.5 | 5.2 |
| Sm25 | 106.8 ± 0.4 | 97.3 ± 8.2 | 85.8 | 35.8 | 4.8 |
| Sm26 | 128.3 ± 17.2 | 98.5 ± 5.9 | 23.5 | 16.8 | 4.2 |
| Sm27 | 92.8 ± 21.7 | 97.0 ± 6.1 | >100 | >100 | 5.0 |
| Sm28 | 19.3 ± 8.4 | 76.5 ± 2.3 | 65.1 | 78.9 | 5.0 |
| Sm29 | 2.0 ± 7.2 | 73.0 ± 1.9 | 64.4 | 71.2 | 4.6 |
| Sm30 | 109.4 ± 2.8 | 99.0 ± 7.6 | >100 | >100 | 4.6 |
| Sm31 | 91.7 ± 2.1 | 97.7 ± 5.9 | 92.7 | >100 | 5.7 |
| Sm32 | 10.9 ± 5.2 | 3.9 ± 6.0 | 37.6 | 24.0 | 5.6 |

TABLE 2

PAINS analysis
Evaluation of compounds Sm1-Sm44 for containing PAINS substructures, listing the three compounds found with possible promiscuous binding structure.

| Compound | PAINS substructure | Comments |
|---|---|---|

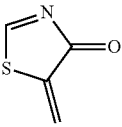

Sm14 — ene_five_het_B(90) — Methylene-thiazolone motif: a frequent hitter in biophysical assays, that can be further oxidized into a reactive metabolite, and is potentially a CYP450 covalent binder.

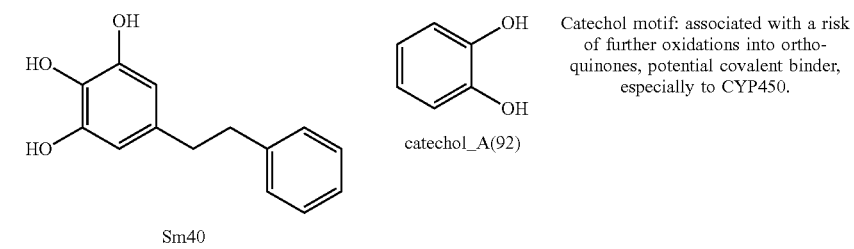

Sm40 — catechol_A(92) — Catechol motif: associated with a risk of further oxidations into ortho-quinones, potential covalent binder, especially to CYP450.

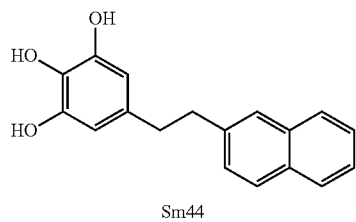 [SMILES: Oc1cc(CCc2ccc3ccccc3c2)cc(O)c1O ; "Sm44"]

Sm44

TABLE 3-continued

DNA-binding and cytotoxicity
Experimental data for Sm15-Sm44 for inhibition of SOX18/DNA binding (FP) and cytotoxicity against two mammalian cell lines. Also shows the predicted lipophilicity as cLogP.

| Cmpd | FP bound fraction (%) 200 μM | FP bound fraction (%) 50 μM | Cytotoxicity ($CC_{50}$ μM) HEK 293 | Cytotoxicity ($CC_{50}$ μM) HepG2 | cLogP |
|---|---|---|---|---|---|
| Sm33 | 9.9 ± 2.3 | 50.1 ± 54.6 | 33.4 | 34.5 | 5.2 |
| Sm34 | 100.9 ± 1.5 | 94.2 ± 1.9 | >100 | >100 | 5.4 |
| Sm35 | −3.7 ± 7.9 | −1.5 ± 3.5 | 52.2 | 30.3 | 5.4 |
| Sm36 | −3.9 ± 6.8 | 10.9 ± 9.6 | 39.9 | 37.7 | 5.0 |
| Sm37 | 103.5 ± 10.4 | 98.2 ± 7.4 | >100 | >100 | 4.1 |
| Sm38 | 119.5 ± 6.6 | 101.6 ± 11.2 | >100 | >100 | 4.1 |
| Sm39 | 116.6 ± 8.1 | 101.7 ± 9.7 | >100 | >100 | 3.6 |
| Sm40 | 92.7 ± 14.7 | 101.0 ± 12.1 | >100 | >100 | 2.7 |
| Sm41 | 90.2 ± 46.1 | 100.3 ± 10.0 | >100 | >100 | 5.3 |
| Sm42 | 104.5 ± 7.7 | 100.7 ± 7.2 | >100 | >100 | 5.3 |
| Sm43 | 113.1 ± 3.6 | 105.5 ± 9.5 | >100 | >100 | 4.7 |
| Sm44 | 53.5 ± 9.6 | 107.6 ± 10.1 | >100 | >100 | 3.8 |

TABLE 4

Off-target activity profile of Sm4
Off-target activity profile for Sm4 at 10uM, using Hit Profilingscreen® package from Eurofins CEREP/Panlabs (France, USA, Taiwan)

| Assay Name | Species | Family | Sub-Family | Inhibition at 10 μM (%) |
|---|---|---|---|---|
| Adenoxine A1 | Human | GPCR | Adenosine | −8 |
| Adenoxine $A_{2A}$ | Human | GPCR | Adenosine | 30 |
| Adrenergic $\alpha_{1A}$ | Rat | GPCR | Adrenergic Receptors | 0 |
| Adrenergic $\alpha_{1B}$ | Rat | GPCR | Adrenergic Receptors | −1 |
| Adrenergic $\alpha_{2A}$ | Human | GPCR | Adrenergic Receptors | 0 |
| Adrenergic $\beta_1$ | Human | GPCR | Adrenergic Receptors | 6 |
| Adrenergic $\beta_2$ | Human | GPCR | Adrenergic Receptors | 2 |
| Cannabinoid $CB_1$ | Human | GPCR | Cannabinoid | 3 |
| Dopamine $D_1$ | Human | GPCR | Dopamine | 12 |
| Dopamine $D_{2s}$ | Human | GPCR | Dopamine | 15 |
| Histamine $H_1$ | Human | GPCR | Histamine | 2 |
| Muscarinic $M_2$ | Human | GPCR | Muscarinic | 13 |
| Muscarinic $M_3$ | Human | GPCR | Muscarinic | 8 |
| Opiate μ (OP3, MOP) | Human | GPCR | Opioid & Opioid-like | 3 |
| Prostanoid $EP_4$ | Human | GPCR | Prostanoid | 27 |
| Serotonin 5-$HT_{2B}$ | Human | GPCR | Serotonin | −2 |
| Calcium Channel L-Type | Rat | Ion Channels | $Ca^{2+}$ Channels | −8 |
| $GABA_A$, Flunitrazepam | Rat | Ion Channels | GABA Channels | −6 |
| $GABA_A$, Muscimal | Rat | Ion Channels | GABA Channels | 6 |
| Glutamate, NMDA | Rat | Ion Channels | Glutamate Channels | −5 |
| Nicotinic Acetylcholine | Human | Ion Channels | Nicotinic Channels | 3 |
| Potassium Channel [$K_{ATP}$] | Hauster | Ion Channels | K+ Channels | 10 |
| Potassium Channel hERG | Human | Ion Channels | K+ Channels | −14 |
| Sodium Channel, Site 2 | Rat | Ion Channels | Na+ Channels | −13 |
| Phorbol Ester | Mouse | Kinases | AGC | 15 |
| Nicotinic Acetylcholine α1 | Human | Nicotinic Channels | Nicotinic Channels | −4 |
| Imidazoline $I_2$ | Rat | Non-Kinase enzymes | Imidazoline | 11 |
| Rolipram | Rat | Non-Kinase enzymes | Phosphodiesterases | 1 |
| Androgen (Testosterone) | Human | Nuclear Receptors | Steroid NR | 1 |
| Estrogen ERalpha | Human | Nuclear Receptors | Steroid NR | −10 |
| Glucocarticoid | Human | Nuclear Receptors | Steroid NR | 12 |
| Thyroid Hormone | Rat | Nuclear Receptors | Non-steroid NR | 36 |
| Sigma1 | Human | Other Receptors | Sigma | −6 |
| Norepinephrine (NET) | Human | Transporters | Norepinephrine | 34 |
| HDAC3 | Human | Epigenetics | HDACS | −4.8 |
| HDAC4 | Human | Epigenetics | HDACS | 5.1 |
| HDAC6 | Human | Epigenetics | HDACS | 1.1 |
| HDAC11 | Human | Epigenetics | HDACS | −29.1 |
| Sirtuin 1 | Human | Epigenetics | HDACS | 0.0 |
| Sirtuin 2 | Human | Epigenetics | HDACS | −5.2 |

TABLE 5

Chemical characterization of synthesized compounds Sm15-Sm44

| Cmpd | Molecular Formula | Chemical Name | HighRes MS Calculated Mass | Found Mass | HPLC Purity by UV 254 nm | NMR |
|---|---|---|---|---|---|---|
| Sm15 | $C_{24}H_{23}NO_2$ | (Z)-N,N-diethyl-2-methoxy-5-(2-(naphthalen-2-yl)vinyl)benzamide | 359.189 | 360.234 [M + H] | >95 | $^1$H $^{13}$C |
| Sm16 | $C_{24}H_{25}NO_2$ | (E)-N,N-diethyl-2-methoxy-6-(2-(naphthalen-2-yl)vinyl)benzamide | 359.189 | 360.234 [M + H] | >95 | $^1$H |
| Sm17 | $C_{24}H_{27}NO_2$ | N,N-diethyl-2-methoxy-6-(2-(naphthalen-2-yl)ethyl)benzamide | 361.204 | 362.250 [M + H] | >95 | $^1$H $^{13}$C |
| Sm18 | $C_{22}H_{25}NO_2$ | N,N-diethyl-2-hydroxy-6-(2-(naphthalen-2-yl)ethyl)benzamide | 347.189 | 348.245 [M + H] | >95 | $^1$H $^{13}$C |
| Sm19 | $C_{20}H_{16}O_3$ | (E/Z)-2-methoxy-6-(2-(naphthalen-2-yl)vinyl)benzoic acid | 304.110 | 305.219 [M + H] | 92 E/Z | $^1$H $^{13}$C |
| Sm20 | $C_{19}H_{14}O_3$ | (E/Z)-2-hydroxy-6-(2-(naphthalen-2-yl)vinyl)benzoic acid | 290.094 | 289.079 [M − H] | 91 E/Z | $^1$H $^{13}$C |
| Sm21 | $C_{15}H_{12}O_3$ | (E)-2-hydroxy-6-styrylbenzoic acid | 240.079 | 239.067 [M − H] | >95 | $^1$H $^{13}$C |
| Sm22 | $C_{15}H_{14}O_3$ | 2-hydroxy-6-phenethylbenzoic acid | 242.094 | 241.100 [M + H] | >95 | $^1$H |
| Sm23 | $C_{29}H_{27}NO_3$ | (Z)-N,N-diethyl-2,4-dimethoxy-6-(2-(naphthalen-2-yl)vinyl)benzamide | 389.199 | 390.222 [M + H] | >95 | $^1$H $^{13}$C |
| Sm24 | $C_{25}H_{27}NO_3$ | (E)-N,N-diethyl-2,4-dimethoxy-6-(2-(naphthalen-2-yl)vinyl)benzamide | 389.199 | 390.222 [M + H] | >95 | $^1$H $^{13}$C |
| Sm25 | $C_{25}H_{29}NO_3$ | N,N-diethyl-2,4-dimethoxy-6-(2-(naphthalen-2-yl)ethyl)benzamide | 391.215 | 392.240 [M + H] | >95 | $^1$H $^{13}$C |
| Sm26 | $C_{23}H_{25}NO_3$ | N,N-diethyl-2,4-dihydroxy-6-(2-(naphthalen-2-yl)ethyl)benzamide | 363.183 | 364.226 [M + H] | >95 | $^1$H $^{13}$C |
| Sm27 | $C_{21}H_{18}O_4$ | (E)-2,4-dimethoxy-6-(2-(naphthalen-2-yl)vinyl)benzoic acid | 334.121 | 335.193 [M + H] | >95 | $^1$H |
| Sm28 | $C_{29}H_{16}O_4$ | (E/Z)-2-hydroxy-4-methoxy-6-(2-(naphthalen-2-yl)vinyl)benzoic acid | 320.105 | 319.093 [M − H] | 91 E/Z | $^1$H $^{13}$C |
| Sm29 | $C_{29}H_{18}O_4$ | 2-hydroxy-4-methoxy-6-(2-(naphthalen-2-yl)ethyl)benzoic acid | 322.121 | 321.120 [M − H] | 90 | $^1$H $^{13}$C |
| Sm30 | $C_{21}H_{20}O_4$ | 2,4-dimethoxy-6-(2-(naphthalen-2-yl)ethyl)benzoic acid | 336.136 | 337.143 [M + H] | >95 | $^1$H $^{13}$C |
| Sm31 | $C_{20}H_{15}ClO_3$ | (E)-4-chloro-2-methoxy-6-(2-(naphthalen-2-yl)vinyl)benzoic acid | 338.071 | 339.139 [M + H] | >95 | $^1$H $^{13}$C |
| Sm32 | $C_{19}H_{13}ClO_3$ | (E)-4-chloro-2-hydroxy-6-(2-(naphthalen-2-yl)vinyl)benzoic acid | 324.055 | 325.045 [M + H] | 90 | $^1$H $^{13}$C |
| Sm33 | $C_{19}H_{13}ClO_3$ | 4-chloro-2-hydroxy-6-(2-(naphthalen-2-yl)ethyl)benzoic acid | 326.071 | 325.062 [M − H] | 85 | $^1$H |
| Sm34 | $C_{22}H_{18}O_3$ | (E)-2-methoxy-4-methyl-6-(2-(naphthalen-2-yl)vinyl)benzoic acid | 318.126 | 319.218 [M + H] | >95 | $^1$H $^{13}$C |
| Sm35 | $C_{20}H_{16}O_3$ | (E)-2-hydroxy-4-methyl-6-(2-(naphthalen-2-yl)vinyl)benzoic acid | 304.110 | 305.223 [M + H] | >95 | $^1$H $^{13}$C |
| Sm36 | $C_{20}H_{18}O_3$ | 2-hydroxy-4-methyl-6-(2-(naphthalen-2-yl)ethyl)benzoic acid | 306.126 | 307.235 [M − H] | 90 | $^1$H $^{13}$C |
| Sm37 | $C_{17}H_{18}O_3$ | (Z)-1,2,3-trimethoxy-5-styrylbenzene | 270.126 | 271.136 [M + H] | >95 | $^1$H $^{13}$C |
| Sm38 | $C_{17}H_{18}O_3$ | (E)-1,2,3-trimethoxy-5-styrylbenzene | 270.126 | 271.136 [M + H] | >95 | $^1$H $^{13}$C |
| Sm39 | $C_{15}H_{20}O_3$ | 1,2,3-trimethoxy-5-phenethylbenzene | 272.141 | 273.150 [M + H] | >95 | $^1$H $^{13}$C |
| Sm40 | $C_{14}H_{14}O_3$ | 5-phenethylbenzene-1,2,3-triol | 230.094 | n.d. | >95 | $^1$H $^{13}$C |
| Sm41 | $C_{21}H_{20}O_3$ | (Z)-2-(3,4,5-trimethoxystyryl)naphthalene | 320.141 | 321.149 [M + H] | >95 | $^1$H |
| Sm42 | $C_{21}H_{22}O_3$ | (E)-2-(2-(3,4,5-trimethoxycyclohexa-1,3-dien-1-yl)vinyl)naphthalene | 322.157 | 321.149 [M + H] | >95 | $^1$H $^{13}$C |
| Sm43 | $C_{21}H_{22}O_3$ | 2-(3,4,5-trimethoxyphenethyl)naphthalene | 322.157 | 323.164 [M + H] | >95 | $^1$H $^{13}$C |
| Sm44 | $C_{18}H_{16}O_3$ | 5-(2-(naphthalen-2-yl)ethyl)benzene-1,2,3-triol | 280.110 | n.d. | >95 | $^1$H $^{13}$C |

Chemical analysis of compounds Sm15-Sm 44. Compound purity was determined by HPLC (ESI-MS/UV/ELSD) and their molecular formulae determined by HighRes MS (ESI microTOF-LC). $^1$H and $^{13}$C NMR experiments were used to confirm the structure (see Appendix A).

REFERENCES

AGRESTI, A. & BIANCHI, M. E. 2003. HMGB proteins and gene expression. *Cuff Opin Genet Dev*, 13, 170-8.

BAELL, J. B. & HOLLOWAY, G. A. 2010. New substructure filters for removal of pan assay interference compounds (PAINS) from screening libraries and for their exclusion in bioassays. *J Med Chem*, 53, 2719-40.

BASS, A. J., WATANABE, H., MERMEL, C. H., YU, S., PERNER, S., VERHAAK, R. G., KIM, S. Y., WARDWELL, L., TAMAYO, P., GAT-VIKS, I., et al. 2009. SOX2 is an amplified lineage-survival oncogene in lung and esophageal squamous cell carcinomas. *Nat Genet*, 41, 1238-42.

BOWLES, J., SCHEPERS, G. & KOOPMAN, P. 2000. Phylogeny of the SOX family of developmental transcription factors based on sequence and structural indicators. *Dev Biol,* 227, 239-55.

BOYADJIEV, S. A. & JABS, E. W. 2000. Online Mendelian Inheritance in Man (OMIM) as a knowledgebase for human developmental disorders. *Clin Genet,* 57, 253-66.

BRANDTS, J. F. & LIN, L. N. 1990. Study of strong to ultratight protein interactions using differential scanning calorimetry. *Biochemistry,* 29, 6927-40.

CERMENATI, S., MOLERI, S., CIMBRO, S., CORTI, P., DEL GIACCO, L., AMODEO, R., DEJANA, E., KOOPMAN, P., COTELLI, F. & BELTRAME, M. 2008. Sox18 and Sox7 play redundant roles in vascular development. *Blood,* 111, 2657-86.

CHATTOPADHYAY, A. & LONDON, E. 1984. Fluorimetric determination of critical micelle concentration avoiding interference from detergent charge. *Anal Biochem,* 139, 408-12.

CHEN, J., SAWYER, N. & REGAN, L. 2013. Protein-protein interactions: General trends in the relationship between binding affinity and interfacial buried surface area. *Protein Science,* 22, 510-515.

CHEN, J., ZHANG, Z., LI, L., CHEN, B. C., REVYAKIN, A., HAJJ, B., LEGANT, W., DAHAN, M., LIONNET, T., BETZIG, E., et al. 2014. Single-molecule dynamics of enhanceosome assembly in embryonic stem cells. *Cell,* 156, 1274-85.

CHOI, S. H., WALES, T. E., NAM, Y., O'DONOVAN, D. J., SLIZ, P., ENGEN, J. R. & BLACKLOW, S. C. 2012. Conformational locking upon cooperative assembly of notch transcription complexes. *Structure,* 20, 340-9.

DARNELL, J. E., JR. 2002. Transcription factors as targets for cancer therapy. *Nat Rev Cancer,* 2, 740-9.

DAWSON, R., MULLER, L., DEHNER, A., KLEIN, C., KESSLER, H. & BUCHNER, J. 2003. The N-terminal domain of p53 is natively unfolded. *J Mol Biol,* 332, 1131-41.

DUONG, T., KOLTOWSKA, K., PICHOL-THIEVEND, C., LE GUEN, L., FONTAINE, F., SMITH, K. A., TRUONG, V., SKOCZYLAS, R., STACKER, S. A., ACHEN, M. G., et al. 2014. VEGFD regulates blood vascular development by modulating SOX18 activity. *Blood,* 123, 1102-12.

FEHER, M. & SCHMIDT, J. M. 2003. Property distributions: differences between drugs, natural products, and molecules from combinatorial chemistry. *J Chem Inf Comput Sci,* 43, 218-27.

FILIPPAKOPOULOS, P., QI, J., PICAUD, S., SHEN, Y., SMITH, W. B., FEDOROV, O., MORSE, E. M., KEATES, T., HICKMAN, T. T., FELLETAR, I., et al. 2010. Selective inhibition of BET bromodomains. *Nature,* 468, 1067-73.

FONTAINE, F., OVERMAN, J. & FRANCOIS, M. 2015. Pharmacological manipulation of transcription factor protein-protein interactions: opportunities and obstacles. *Cell Regen* (Lond), 4, 2.

FRANCOIS, M., CAPRINI, A., HOSKING, B., ORSENIGO, F., WILHELM, D., BROWNE, C., PAAVONEN, K., KARNEZIS, T., SHAYAN, R., DOWNES, M., et al. 2008. Sox18 induces development of the lymphatic vasculature in mice. *Nature,* 456, 643-7.

FUKADA, H., STURTEVANT, J. M. & QUIOCHO, F. A. 1983. Thermodynamics of the binding of L-arabinose and of D-galactose to the L-arabinose-binding protein of *Escherichia coli. J Biol Chem,* 258, 13193-8.

GAGOSKI, D., MUREEV, S., GILES, N., JOHNSTON, W., DAHMER-HEATH, M., SKALAMERA, D., GONDA, T. J. & ALEXANDROV, K. 2015. Gateway-compatible vectors for high-throughput protein expression in pro- and eukaryotic cell-free systems. *J Biotechnol,* 195, 1-7.

GAMPER, A. M. & ROEDER, R. G. 2008. Multivalent Binding of p53 to the STAGA Complex Mediates Coactivator Recruitment after UV Damage. *Molecular and Cellular Biology,* 28, 2517-2527.

GUBBAY, J., COLLIGNON, J., KOOPMAN, P., CAPEL, B., ECONOMOU, A., MUNSTERBERG, A., VIVIAN, N., GOODFELLOW, P. & LOVELL-BADGE, R. 1990. A gene mapping to the sex-determining region of the mouse Y chromosome is a member of a novel family of embryonically expressed genes. *Nature,* 346, 245-50.

HOPKINS, A. L. & GROOM, C. R. 2002. The druggable genome. *Nat Rev Drug Discov,* 1, 727-30.

HOSKING, B. M., WANG, S. C., CHEN, S. L., PENNING, S., KOOPMAN, P. & MUSCAT, G. E. 2001. SOX18 directly interacts with MEF2C in endothelial cells. *Biochem Biophys Res Commun,* 287, 493-500.

HOSKING, B. M., WANG, S. C., DOWNES, M., KOOPMAN, P. & MUSCAT, G. E. 2004. The VCAM-1 gene that encodes the vascular cell adhesion molecule is a target of the Sry-related high mobility group box gene, Sox18. *J Biol Chem,* 279, 5314-22.

HUANG, Y. H., JANKOWSKI, A., CHEAH, K. S., PRABHAKAR, S. & JAUCH, R. 2015. SOXE transcription factors form selective dimers on non-compact DNA motifs through multifaceted interactions between dimerization and high-mobility group domains. *Sci Rep,* 5, 10398.

IRWIN, J. J., DUAN, D., TOROSYAN, H., DOAK, A. K., ZIEBART, K. T., STERLING, T., TUMANIAN, G. & SHOICHET, B. K. 2015. An Aggregation Advisor for Ligand Discovery. *Journal of Medicinal Chemistry,* 58, 7076-7087.

KLAUS, M., PROKOPH, N., GIRBIG, M., WANG, X., HUANG, Y. H., SRIVASTAVA, Y., HOU, L., NARASIMHAN, K., KOLATKAR, P. R., FRANCOIS, M., et al. 2016. Structure and decoy-mediated inhibition of the SOX18/Prox1-DNA interaction. *Nucleic Acids Res,* 44, 3922-35.

KOVTUN, O., MUREEV, S., JUNG, W., KUBALA, M. H., JOHNSTON, W. & ALEXANDROV, K. 2011. Leishmania cell-free protein expression system. *Methods,* 55, 58-64.

LAGORCE, D., SPERANDIO, O., GALONS, H., MITEVA, M. A. & VILLOUTREIX, B. O. 2008. FAF-Drugs2: free ADME/tox filtering tool to assist drug discovery and chemical biology projects. *BMC Bioinformatics,* 9, 396.

LAX, I., JOHNSON, A., HOWK, R., SAP, J., BELLOT, F., WINKLER, M., ULLRICH, A., VENNSTROM, B., SCHLESSINGER, J. & GIVOL, D. 1988. Chicken epidermal growth factor (EGF) receptor: cDNA cloning, expression in mouse cells, and differential binding of EGF and transforming growth factor alpha. *Mol Cell Biol,* 8, 1970-8.

LEUNG, C. H., CHAN, D. S. H., MA, V. P. Y. & MA, D. L. 2013. DNA-Binding Small Molecules as Inhibitors of Transcription Factors. *Medicinal Research Reviews,* 33, 823-846.

LIU, L. J., LEUNG, K. H., CHAN, D. S., WANG, Y. T., MA, D. L. & LEUNG, C. H. 2014. Identification of a natural product-like STAT3 dimerization inhibitor by structure-based virtual screening. *Cell Death Dis,* 5, e1293.

LOPEZ-BIGAS, N., BLENCOWE, B. J. & OUZOUNIS, C. A. 2006. Highly consistent patterns for inherited human diseases at the molecular level. *Bioinformatics*, 22, 269-77.

MAPP, A. K., PRICER, R. & STURLIS, S. 2015. Targeting transcription is no longer a quixotic quest. *Nat Chem Biol*, 11, 891-894.

MCMILLIAN, M. K., LI, L., PARKER, J. B., PATEL, L., ZHONG, Z., GUNNETT, J. W., POWERS, W. J. & JOHNSON, M. D. 2002. An improved resazurin-based cytotoxicity assay for hepatic cells. *Cell Biol Toxicol*, 18, 157-73.

MIAN, I. S., BRADWELL, A. R. & OLSON, A. J. 1991. Structure, function and properties of antibody binding sites. *Journal of Molecular Biology*, 217, 133-151.

MITTAL, D., YOUNG, A., STANNARD, K., YONG, M., TENG, M. W., ALLARD, B., STAGG, J. & SMYTH, M. J. 2014. Antimetastatic effects of blocking PD-1 and the adenosine A2A receptor. *Cancer Res*, 74, 3652-8.

MIYOSHI, K., TAKAISHI, M., NAKAJIMA, K., IKEDA, M., KANDA, T., TARUTANI, M., IIYAMA, T., ASAO, N., DIGIOVANNI, J. & SANO, S. 2011. Stat3 as a therapeutic target for the treatment of psoriasis: a clinical feasibility study with STA-21, a Stat3 inhibitor. *J Invest Dermatol*, 131, 108-17.

MUREEV, S., KOVTUN, O., NGUYEN, U. T. & ALEXANDROV, K. 2009. Species-independent translational leaders facilitate cell-free expression. *Nat Biotechnol*, 27, 747-52.

NARASIMHAN, K., MICOINE, K., LACOTE, E., THORIMBERT, S., CHEUNG, E., HASENKNOPF, B. & JAUCH, R. 2014. Exploring the utility of organo-polyoxometalate hybrids to inhibit SOX transcription factors. *Cell Regen (Lond)*, 3, 10.

NARASIMHAN, K., PILLAY, S., BIN AHMAD, N. R., BIKADI, Z., HAZAI, E., YAN, L., KOLATKAR, P. R., PERVUSHIN, K. & JAUCH, R. 2011. Identification of a polyoxometalate inhibitor of the DNA binding activity of Sox2. *ACS Chem Biol*, 6, 573-81.

NG, C. K., LI, N. X., CHEE, S., PRABHAKAR, S., KOLATKAR, P. R. & JAUCH, R. 2012. Deciphering the Sox-Oct partner code by quantitative cooperativity measurements. *Nucleic Acids Res*, 40, 4933-41.

NIWA, H., OGAWA, K., SHIMOSATO, D. & ADACHI, K. 2009. A parallel circuit of LIF signalling pathways maintains pluripotency of mouse ES cells. *Nature*, 460, 118-122.

PENNISI, D., GARDNER, J., CHAMBERS, D., HOSKING, B., PETERS, J., MUSCAT, G., ABBOTT, C. & KOOPMAN, P. 2000. Mutations in Sox18 underlie cardiovascular and hair follicle defects in ragged mice. *Nat Genet*, 24, 434-7.

PERISSI, V. & ROSENFELD, M. G. 2005. Controlling nuclear receptors: the circular logic of cofactor cycles. *Nat Rev Mol Cell Biol*, 6, 542-54.

PILLINGER, M. H., CAPODICI, C., ROSENTHAL, P., KHETERPAL, N., HANFT, S., PHILIPS, M. R. & WEISSMANN, G. 1998. Modes of action of aspirin-like drugs: Salicylates inhibit Erk activation and integrin-dependent neutrophil adhesion. *Proceedings of the National Academy of Sciences*, 95, 14540-14545.

PROKOP, J. W., LEEPER, T. C., DUAN, Z. H. & MILSTED, A. 2012. Amino acid function and docking site prediction through combining disease variants, structure alignments, sequence alignments, and molecular dynamics: a study of the HMG domain. *BMC Bioinformatics*, 13 Suppl 2, S3.

REICHMANN, D., RAHAT, O., ALBECK, S., MEGED, R., DYM, O. & SCHREIBER, G. 2005. The modular architecture of protein-protein binding interfaces. *Proc Natl Acad Sci USA*, 102, 57-62.

SACILOTTO, N., MONTEIRO, R., FRITZSCHE, M., BECKER, P. W., SANCHEZ-DEL-CAMPO, L., LIU, K., PINHEIRO, P., RATNAYAKA, I., DAVIES, B., GODING, C. R., et al. 2013. Analysis of DII4 regulation reveals a combinatorial role for Sox and Notch in arterial development. *Proc Natl Acad Sci USA*, 110, 11893-8.

SARKAR, A. & HOCHEDLINGER, K. 2013. The Sox Family of Transcription Factors: Versatile Regulators of Stem and Progenitor Cell Fate. *Cell Stem Cell*, 12, 15-30.

SENISTERRA, G., CHAU, I. & VEDADI, M. 2012. Thermal denaturation assays in chemical biology. *Assay Drug Dev Technol*, 10, 128-36.

SENISTERRA, G. A. & FINERTY, P. J., JR. 2009. High throughput methods of assessing protein stability and aggregation. *Mot Biosyst*, 5, 217-23.

SENISTERRA, G. A., MARKIN, E., YAMAZAKI, K., HUI, R., VEDADI, M. & AWREY, D. E. 2006. Screening for ligands using a generic and high-throughput light-scattering-based assay. *J Biomol Screen*, 11, 940-8.

SENISTERRA, G. A., SOO HONG, B., PARK, H. W. & VEDADI, M. 2008. Application of high-throughput isothermal denaturation to assess protein stability and screen for ligands. *J Biomol Screen*, 13, 337-42.

SHRAKE, A. & ROSS, P. D. 1990. Ligand-induced biphasic protein denaturation. *J Bid Chem*, 265, 5055-9.

SHRAKE, A. & ROSS, P. D. 1992. Origins and consequences of ligand-induced multiphasic thermal protein denaturation. *Biopolymers*, 32, 925-40.

SIERECKI, E., GILES, N., POLINKOVSKY, M., MOUSTAQIL, M., ALEXANDROV, K. & GAMBIN, Y. 2013. A cell-free approach to accelerate the study of protein-protein interactions in vitro. *Interface Focus*, 3, 20130018.

SIERECKI, E., STEVERS, L. M., GILES, N., POLINKOVSKY, M. E., MOUSTAQIL, M., MUREEV, S., JOHNSTON, W. A., DAHMER-HEATH, M., SKALAMERA, D., GONDA, T. J., et al. 2014. Rapid mapping of interactions between Human SNX-BAR proteins measured in vitro by AlphaScreen and single-molecule spectroscopy. *Mol Cell Proteomics*, 13, 2233-45.

VAQUERIZAS, J. M., KUMMERFELD, S. K., TEICHMANN, S. A. & LUSCOMBE, N. M. 2009. A census of human transcription factors: function, expression and evolution. *Nat Rev Genet*, 10, 252-63.

VASSILEV, L. T., VU, B. T., GRAVES, B., CARVAJAL, D., PODLASKI, F., FILIPOVIC, Z., KONG, N., KAMMLOTT, U., LUKACS, C., KLEIN, C., et al. 2004. In vivo activation of the p53 pathway by small-molecule antagonists of MDM2. *Science*, 303, 844-8.

VOGLER, M., DINSDALE, D., DYER, M. J. & COHEN, G. M. 2009. Bcl-2 inhibitors: small molecules with a big impact on cancer therapy. *Cell Death Differ*, 16, 360-7.

WRIGHT, P. E. & DYSON, H. J. 2015. Intrinsically disordered proteins in cellular signalling and regulation. *Nat Rev Mol Cell Biol*, 16, 18-29.

ZHANG, J. H., CHUNG, T. D. & OLDENBURG, K. R. 1999. A Simple Statistical Parameter for Use in Evaluation and Validation of High Throughput Screening Assays. *J Biomol Screen*, 4, 67-73.

DRAGO, R. L. C. A. R., Thermodynamic Data for the Formation of Molecular Complexes between Phenyl Substituted Amides and Iodine. J. Am. Chem. Soc, 1963. 85(5): p. 505-508

S. O. DE SILVA, J. N. R., R. J. BILLEDEAU, X. WANG, D. J. NORRIS, AND V. SNIECKUS, Directed ortho metalation of n,n-diethyl benzamides.methodology and regiospecific synthesis of useful contiguously tri- and tetra-substituted oxygenated aromatics, phthalides and phthalic anhydrides. Tetrahedro, 1992. 48(23): p. 4863-4878.

ZIMMERMANN, T. J., et al., Discovery of a potent and selective inhibitor for human carbonyl reductase 1 from propionate scanning applied to the macrolide zearalenone. Bioorganic & *Medicinal Chemistry,* 2009. 17(2): p. 530-536.

JO, G., et al., Complete NMR data of methoxylated cis- and trans-stilbenes as well as 1,2-diphenylethanes. Magnetic Resonance in Chemistry, 2011. 49(6): p. 374-377.

TAUB, D., GIROTRA, N, N., HOFFSOMMER, R. D., KUO, C. H., SLATES, H. L., WEBER, S., L. WENDLER, Total synthesis of the macrolide, zearalenone. Tetrahedron, 1968. 24: p. 2443-2461.

SUBHASH P. KHANAPURE, R. T. R., AND EDWARD R. BIEHL, The preparation of anthraquinones and anthracyclinones via the reaction of haloarenes and cyanophthalides under aryne-forming Conditions. J. Org. Chem., 1987. 52: p. 5685-5690.

MAL, D., et al., DBU-CH31, a Potential Substitute for CH2N2 in the preparation of methyl esters and methyl aryl ethers: Studies with assorted acids. Synthetic Communications, 2008. 38(22): p. 3937-3946.

Example 2

Pharmacological Targeting of the Transcription Factor SOX18 Delays Breast Cancer in Mice
Materials and Methods
Experimental Reproducibility All data and statistical analysis in this study were generated from at least three independent experiments unless indicated otherwise. Technical replicates were included in every experiment to reduce background noise and detect technical anomalies. Samples of distinct experimental conditions were not exposed to any specific method of randomization, and groups were assessed under non-blinded conditions.

Plasmid Preparation for Cell-Free Expression

The genetically encoded tags used here are enhanced GFP (GFP), mCherry (Cherry) and cMyc (myc). The proteins were cloned into the following cell free expression Gateway destination vectors respectively: N-terminal GFP tagged (pCellFree_G03), N-terminal Cherry-cMyc (pCellFree_G07) and C-terminal Cherry-cMyc tagged (pCellFree_G08) (Gagoski et al. 2015). The Open Reading Frames (ORFs) corresponding to the human SOX7 (BC071947), SOX17, RBPJ (BC020780) and MEF2C (BC026341) were sourced from the Human ORFeome collection version 1.1 and 5.1 or the Human Orfeome collaboration OCAA collection (Open Biosystems) as previously described and cloned at the ARVEC facility, UQ Diamantina Institute. The entry clones pDONOR223 or pENTR201 vectors were exchanged with the ccdB gene in the expression plasmid by LR recombination (Life Technologies, Australia). The full-length human SOX18 gene was synthesized (IDT) and the transfers to vectors was realized using Gateway PCR cloning.

Cell-Free Protein Expression

The translation competent Leishmania tarentolae extract (LTE) was prepared as previously described (Mureev et al. 2009, Kovtun et al. 2011). Protein pairs were co-expressed by adding 30 nM of GFP template plasmid and 60 nM of Cherry template plasmid to LTE and incubating for 3 hours at 27° C.

ALPHA-Screen Assay

The ALPHA-Screen Assay was performed as previously described (Sierecki et al. 2014), using the cMyc detection kit and Proxiplate-384 Plus plates (PerkinElmer). A serial dilution of each sample was measured. The LTE lysate co-expressing the proteins of interest was diluted in buffer A (25 mM HEPES, 50 mM NaCl). For the assay, 12.5 µL (0.4 µg) of Anti-cMyc coated Acceptor Beads in buffer B (25 mM HEPES, 50 mM NaCl, 0.001% NP40, 0.001% casein) were aliquoted into each well. This was followed by the addition of 2 µL of diluted sample and 2 µL of biotin labeled GFP-Nanotrap in buffer A. The plate was incubated for 45 min at RT. Afterward, 2 µL (0.4 µg) of Streptavidin coated Donor Beads diluted in buffer A, were added, followed by incubation in the dark for 45 min at RT. The ALPHA-Screen signal was obtained on an Envision Multilabel Plate Reader (PerkinElmer), using the manufacturer's recommended settings (excitation: 680/30 nm for 0.18 s, emission: 570/100 nm after 37 ms). The resulting bell-shaped curve is an indication of a positive interaction, while a flat line reflects a lack of interaction between the proteins. The measurement of each protein pair was repeated a minimum of three times using separate plates. The Binding Index was calculated as: $BI=[(I-I\_neg)/(I\_ref-I\_neg)]\times 100$ For each experiment, I is the highest signal level (top of the hook effect curve) and Ineg is the lowest (background) signal level. The signals were normalized to the Iref signal obtained for the interaction of SOX18 with itself.

For PPI disruption assay, protein pairs expressed in LTE were incubated for 1 h with 100 µM Sm4 or DMSO alone (0.7% DMSO final). 100 µM Sm4 or DMSO was also added to buffer B. PPI disruption was calculated as: $(1-I\_Sm4/I\_DMSO)\times 100$.

For IC50 determination, the assay was identical but a dilution range of Sm4 was used (0.3 to 300 µM). Percentage of interaction was calculated as: $I\_Sm4/I\_DMSO\times 100$. Data from at least 3 independent experiments were fitted in GraphPad Prism (RRID: SCR_007370) version 6.0 using 3-parameter non-linear regression.

Cell Culture and Transfection

COS-7 cells were purchased from ATCC (CRL-1651, RRID: CVCL_0224) cultured at 37° C., 5% CO2 in DMEM (Life technologies, 11995) with added FBS, sodium pyruvate, L-glutamine, penicillin, streptomycin, non-essential amino acids and HEPES (N-2-hydroxyethylpiperazine-N'-2-ethanesulfonic acid). COS-7 cells were transfected for 4-6 h, and incubated for another 24 h before lysis and luciferase assay (Perkin Elmer, 6016711). Human umbilical vein endothelial cells (HUVECs) were purchased from Lonza Australia (CC-2519A). HUVEC for ChIP-MS, ChIP-seq and RNA-seq analyses were transfection for 7 h and incubated another 14 h. During small molecule treatment, cells were grown in medium containing low serum (0.4% FBS). HUVECs were cultured at 37° C., 5% CO2 in EGM-2 media supplemented according to the EGM-2 bullet kit instruction (Lonza, CC-3162). Cells for were grown in 35 mm dishes to 80-90% confluency, and transfected with plasmid mouse pSG5 Sox18, plasmid pSG5 cMyc-Sox18, or plasmid cMyc using X-tremegene 9 DNA transfection reagent (Roche, 06365787001) according to the manufacturer's instructions. All cell lines were tested negative for *Mycoplasma* contamination.

Chromatin Immunoprecipitation

ChIP experiments were performed as previously described (Schmidt et al. 2009). Immunoprecipitation was performed using Anti-cMyc (Cell Signaling, #2276, RRID: AB_2314825) on HUVECs overexpressing cMyc-tagged SOX18.

ChIP-Seq and Analysis

Following IP, DNA amplification was performed using TruSeq ChIPseq kit (Illumina, IP-202-1012), using 0.5 µM of the universal reverse PCR primer and the forward PCR primer containing the index sequence of choice in 50 µL 1×NEBNext High-Fidelity PCR Master Mix (New England Biolabs, M0541). The number of PCR cycles ranged from 13 to 18, depending on the ChIP efficiency. The PCR product was purified using AMPure beads (1.8 volume) and eluted in 20 µL of resuspension buffer (Tris-Acetate 10 mM pH 8). The library was quantified using the KAPA library quantification kit for Illumina sequencing platforms (KAPA Biosystems, KK4824) and 50 bp single end reads were sequenced on a HiSeq2500 following the manufacturer's protocol. Illumina fastq files were mapped to the GRCh37/UCSC hg19 genome assembly using bowtie, and peaks were called using MACS version 2.1.0. using input. To avoid false positive peaks calling due to the cMyc epitope, ChIP-seq with the cMyc epitope only were performed in parallel to SOX18-cMyc ChIP-seq and peaks called in these experimental conditions were substracted to the peaks called in the SOX18-cMyc conditions. Genomic Regions Enrichment of Annotations Tool (GREAT, RRID: SCR_005807)) was used to analyse the functional significance of cis-regulatory regions. ChIP-seq data are available in the ArrayExpress database (www.ebi.ac.uk/arrayexpress, RRID: SCR_002964) under accession number E-MTAB-4480 (SOX7) and E-MTAB-4481 (SOX18).

ChIP-MS (RIME)

ChIP-MS experiments were performed as previously described (Mohammed et al. 2013). Peptides common between SOX18-cMyc and the negative control (cMyc-only) were binned and only peptides that were uniquely detected in the SOX18-cMyc transfected cell were considered for analysis.

RNA-Seq and Analysis

Quadruplicate samples were processed for whole transcriptome sequencing using TruSeq stranded total RNA library prep kit (Illumina). Reads were mapped to the hg19 reference human genome using STAR aligner (Dobin et al. 2013), and only uniquely aligned reads were considered. Transcripts were assigned to genes using htseq_count (HT-seq package) (Anders, Pyl, and Huber 2015), and differential expression was calculated using DEseq2 (Love, Huber, and Anders 2014). Genes with adjusted p-value <0.05 were considered significant.

Differentially expressed genes were identified between Sm4-treated and DMSO control in SOX18 over-expressing cells, and separated in up-regulated and down-regulated (DOWN) genes. The locations of their transcription start sites (TSS) were correlated to the locations of transcription factors binding events that are available from the ENCODE consortium (RRID: SCR_006793), and from the SOX18 and SOX7 ChIP-seq experiment we performed in this study. To ensure that the TSSs were independent, a TSS was allowed to only be assigned to 1 ChIP-seq peak. Transcripts with ≥2-fold absolute fold change (log 2FC≥1 or ≤−1) were included for distance to TSS analysis. The median distance between the TSSs and binding events was compared to the expected distance of a set of randomly selected genes to obtain the median ratio. The control set of genes was selected from the pool of genes expressed in HUVECs so that they had a similar distribution of expression levels. To ensure that no bias was introduced by potential co-regulation of genes by SOX18 and any other transcription factor analysed, we subtracted genes with SOX18 peaks from the analyses for other transcription factors. The reverse analysis was also performed, subtracting genes containing c-JUN peaks from the analysis for SOX18. RNA-seq data are available in the ArrayExpress database (www.ebi.ac.uk/arrayexpress) under accession number E-MTAB-4511.

Quantitative RT-PCR

Total RNA was extracted using RNeasy mini kit (Qiagen, 74106) according to the manufacturers protocol, including on column DNA digestion. cDNA was synthetised from 1 µg of purified RNA using the high capacity cDNA reverse transcription kit (Life Technologies, 4368813). Amplification and quantitation of target cDNA was performed in technical triplicate of at least 3 biological replicates using the SYBR green (Life Technologies, 4312704) methods. Reactions were run in 10 µL in 384-well plates using the ViiA 7 Real-Time PCR system. Housekeeper genes (β-actin for tg (Dll4in3:eGFP), ef1α for tg (−6.5kdrl:eGFP), chd5 for tg (fli1a:eGFP, −6.5kdrl:mCherry), RPL13 and GAPDH for HUVECs) were selected based on the stability of their expression throughout the set of experimental conditions, or chosen on grounds of their vascular expression to normalize to endothelial cell content. Primer efficiencies were calculated using LinRegPCR, and amplification data was analysed using ViiA7 software and the Q-gene PCR analysis template.

Zebrafish Aquaculture and Analysis

Zebrafish were maintained as previously described (Hogan et al. 2009), and all procedures involving animals conformed to guidelines of the animal ethics committee at the University of Queensland (IMB/030/16/NHMRC/ARC/HF) or were approved by local ethical review and licensed by the UK Home Office (PPL 30/2783 and PPL 30/3324). The tg (−6.5kdrl:eGFP), tg (fli1a:eGFP, −6.5kdrl:mCherry) and tg (Dll4in3:GFP) were previously described (Sacilotto et al. 2013, Duong et al. 2014, Lawson and Weinstein 2002).

Dechorionation was performed by treatment with 25 µg/mL or 5 µg/mL pronase for 2 h, or overnight, respectively. Zebrafish larvae were anesthetized using 0.01% tricaine. Representative larvae were embedded in 0.5% low-melting point agarose and imaged with the Zeiss LSM 710 confocal microscope.

Zebrafish In Situ Hybridization and Sectional Analysis

Wholemount zebrafish (28 and 48 hpf) in situ hybridization was performed as previously described (Thisse and Thisse 2008) with probe templates for dab (Song et al. 2004) and ephrinB2a (Durbin et al. 1998). Yolk sac was removed prior to addition of in 70% glycerol. For transverse sections, whole larvae where embedded in 4% agarose, sectioned at 150 µm using the Leica VT1000 S vibrating microtome. Imaging was performed on the Olympus BX-51 brightfield microscope (ISH), and Zeiss LSM 510 confocal microscope. For fluorescent images, larvae were DAPI-stained before embedding.

Small Molecule Treatment and Morpholino Injections

All treatment with putative small molecule inhibitors, and corresponding control conditions, were performed in the presence of low concentration of DMSO (≤1% v/v) to achieve reliable homogeneous solutions, and were prepared from 10 mM DMSO stock. For cell culture, small molecules were added to fresh media directly following transfection and cells were grown in this media until time-point of cell harvesting. For in vivo experiments involving zebrafish, compound treatment was initiated at the designated timepoints by replacing the media, and media+compound was refreshed daily for the duration of the experiment. PTU treatment (0.003%) was done in parallel with the small molecules to block pigment formation when necessary. Previously published and validated morpholino oligomers against sox7, sox18 (Herpers et al. 2008) and rbpj (Sacilotto et al. 2013) were micro-injected into single cell zebrafish zygotes at 5 ng for experiments performed with tg (6.5kdrl: eGFP) and tg (fli1a:eGFP, −6.5kdrl:mCherry), and 0.125-0.15 pmol suboptimal concentrations for experiments performed with tg (Dll4in3:eGFP).

Mice and Mouse Model

BALB/c wild-type (WT) were purchased from Walter and Eliza Hall Institute for Medical Research and used between the ages of 6 and 10 weeks. Mouse 4T1.2 mammary carcinoma cells were cultured in complete RPMI with 10% FBS in a 5% CO2 incubator. 5×104 4T1.2 tumor cells were inoculated into the fourth mammary fat-pad of BALB/c WT mice as previously described (Mittal et al. 2014). Briefly, on day 3 after tumor implantation, mice were orally gavaged daily for 10 days with 25 mg/kg of body weight Sm4, aspirin or vehicle PBS. Tumor size was measured with a digital caliper as the product of two perpendicular diameters. Blood plasma was collected from mice on day 7 and 12, and Sm4 concentrations were analyzed using a 4000 Qtrap LC-MS/MS system mass spectrometer. On day 12, mice were anesthetised to surgically remove primary tumor, or mice were put through surgery procedure with no excision of the primary tumor, and the wound was closed with surgical clips. Tumors were collected in formalin for histology. Lungs were harvested on day 28 and fixed in Bouin's solution for 24 h and metastatic tumor nodules were counted under a dissection microscope. Survival of the mice was monitored in experiments where the lungs were not harvested. Groups of 6 to 14 mice per experiment were used for experimental tumor assays, to ensure adequate power to detect biological differences. All experiments were approved by the QIMR Berghofer Medical Research Institute Animal Ethics Committee (P1505).

For quantitation of the vasculature in the tumors, fixed tissues were embedded in 4% agarose and sectioned all the way through at 300 μm on a Leica VT1000 S vibrating microtome. Sections were collected on glass slides and imaged for bright field analysis on the penetration of perfused vessels. Subsequently, immunofluorescent staining was performed on sections using anti-mouse Endomucin (cat #sc-53941, RRID: AB_2100038), ERG (cat #ab92513, RRID: AB_2630401), PROX1 (AngioBio cat #11-002, RRID: AB_10013720) and Podoplanin (AngioBio cat #11-033, AB_2631191) antibodies. Whole tumor sections were imaged by acquiring a series of images along the z-axis using a 10× objective on a Zeiss LSM 710 confocal microscope. Subsequently, high-resolution images were captured using a 20× objective on 3-4 separate regions from each tumor, to account for heterogeneity of the vascular density within the tumors and minimise bias. Raw image files with identical dimensions (1274.87 μm×1274.87 μm×89.05 μm) were loaded into Imaris (Bitplane, RRID: SCR_007370), and processed using "spots" function to count ERG or PROX1-positive nuclei and "surface" to calculate volume or area of Endomucin or Podoplanin positive vessels. For each tumor (n=6), counts from the multiple regions were averaged and the data was plotted in Graphpad Prism 6.

BALB/c wild-type (WT) were purchased from Walter and Eliza Hall Institute for Medical Research and used between the ages of 6 and 10 weeks. Mouse 4T1.2 mammary carcinoma cells were cultured in complete RPMI with 10% FBS in a 5% CO2 incubator. 5×104 4T1.2 tumour cells were inoculated into the fourth mammary fat-pad of BALB/c WT mice as previously described (Mittal et al. 2014). Briefly, on day 3 after tumour implantation, mice were orally gavaged daily for 10 days with different doses of Sm4 ranging from 5 mg/kg to 50 mg/kg of body weight or vehicle PBS. Tumour size was measured with a digital calliper as the product of two perpendicular diameters. On day 12, mice were anesthetised to surgically remove primary tumour, and the wound was closed with surgical dips. Tumours were collected in formalin for histology. Survival of the mice was monitored in groups of 6 to 12 mice per experiment, to ensure adequate power to detect biological differences. All experiments were approved by the QIMR Berghofer Medical Research Institute Animal Ethics Committee (P1505).

Results and Discussion

Figure 9:
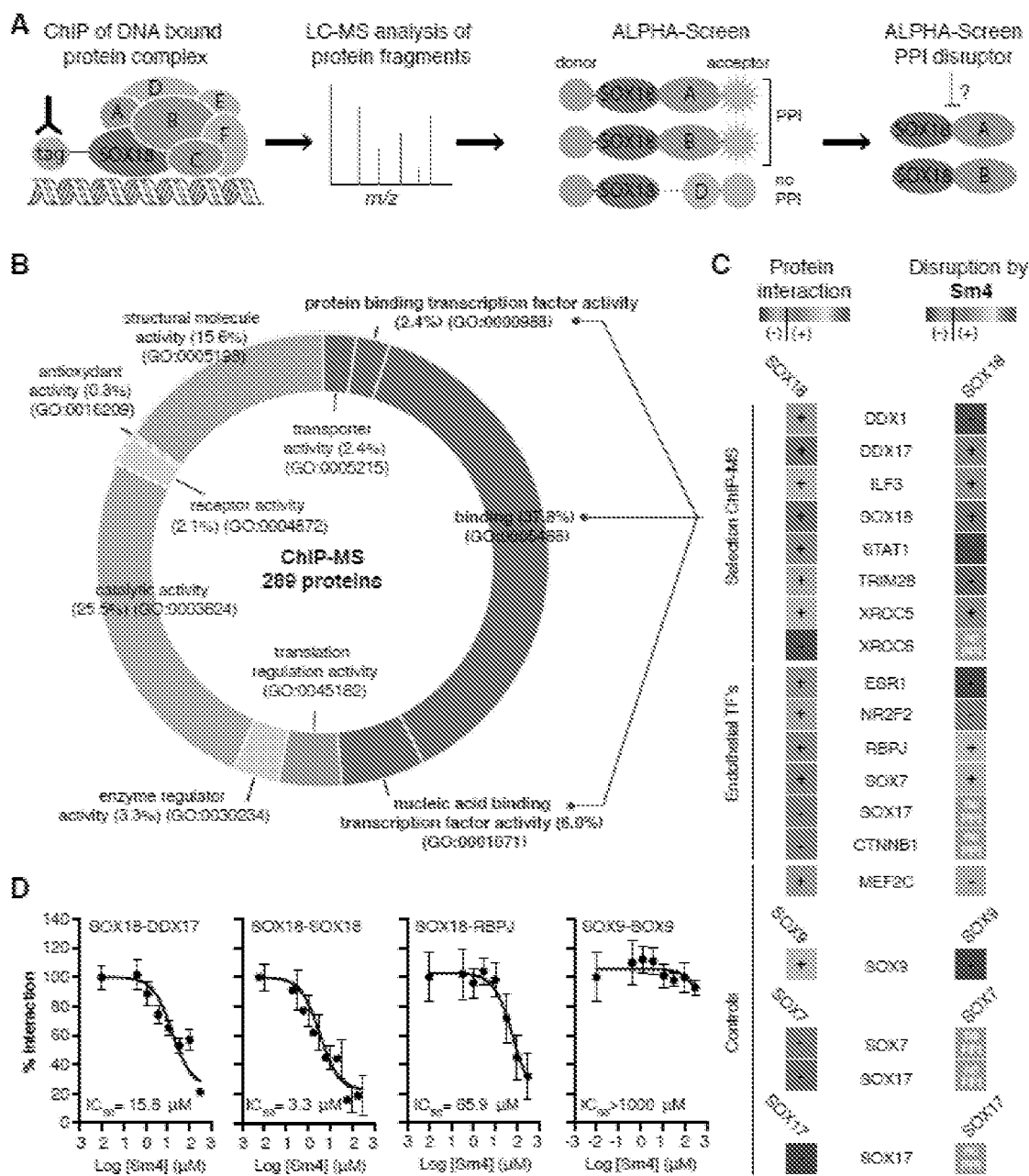
FIG. 9: Mapping of SOX18 interactome and disruption of interactions by Sm4. (A) Schematic of the experimental strategy to deconvolute SOX18-dependent protein-protein interactions (PPIs) combining Chromatin immunoprecipitation-mass spectrometry (ChIP-MS) and Amplified Luminescent Proximity Homogeneous Assay (ALPHA-Screen) methods. (B) GO-term analysis for molecular function on the 289 proteins identified by SOX18-cMyc ChIP-MS in human umbilical vein endothelial cells (HUVECs). Non-specific interactors found in Myc-tag-only transfected cells were subtracted. Proteins with nucleic acid binding or protein binding capacity (purple) were considered for consecutive direct interaction studies to enhance likeness of identifying direct interactors. (C) Left column: heatmap representation of SOX18 pairwise PPIs as tested by ALPHA-Screen, on a selection of ChIP-MS SOX18 associated proteins, endothelial transcription factors and positive/negative control proteins. Right column: heatmap representation of Sm4 activity on SOX18-dependent protein-protein interactions, as tested at 100 μM. Interaction and disruption threshold is indicated in the scale bar by a black line. Levels of interaction and disruption above the threshold are demarked by '+', and below the threshold by '−'. Tagged proteins were expressed in the Leishmania tarentolae cell-free protein expression system. (D) Representative ALPHA-Screen concentration-response curve for SOX18 PPI disruption by Sm4. Data shown are mean±s.e.m.
Figure 10:
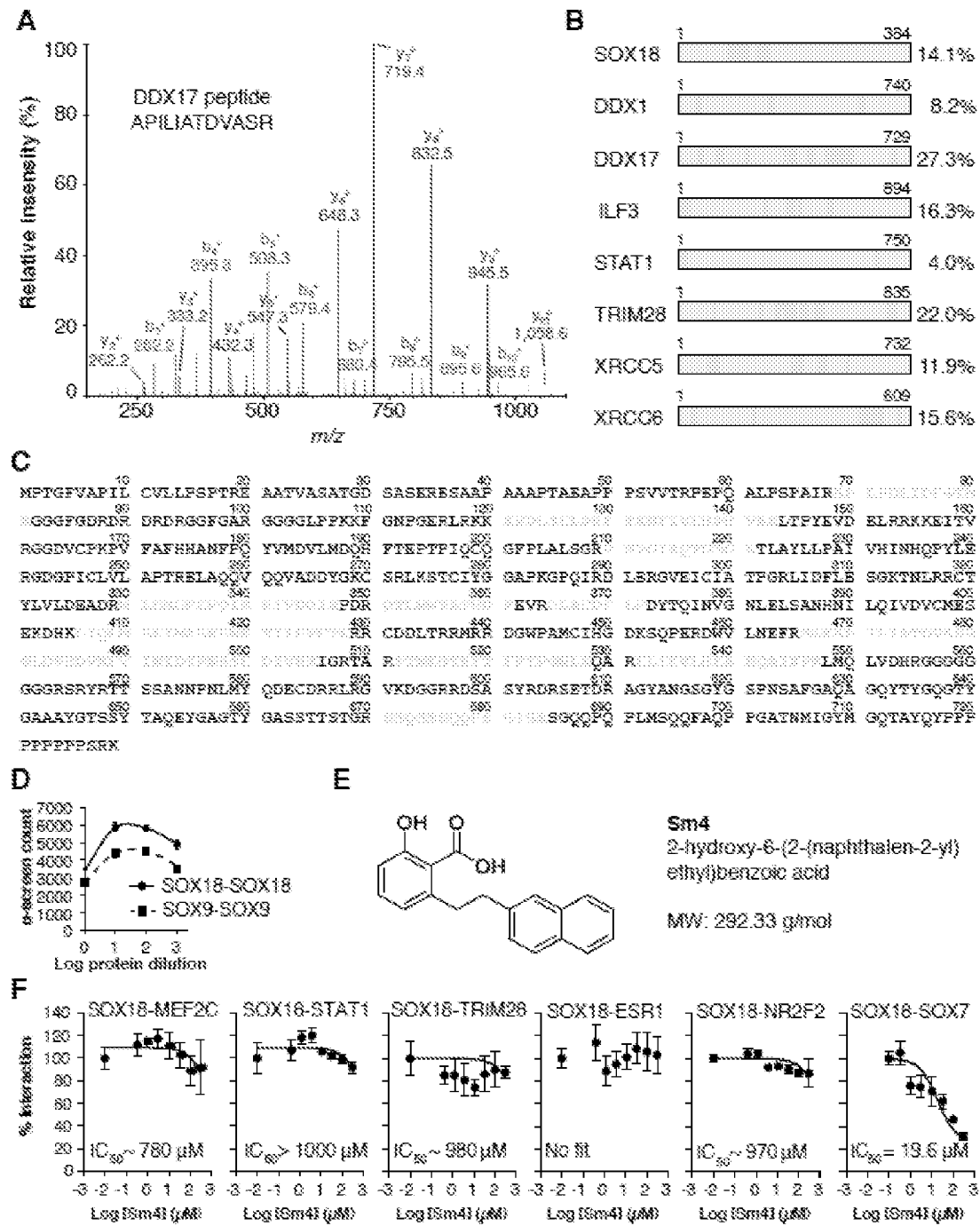
FIG. 10: QC of SOX18 PPIs and effect of Sm4. (A) Mass spectrometry spectrum for a representative double charged DDX17 peptide with the sequence KAPILIATDVASRG (Muscat ion score 51.6), identified from immunoprecipitation of cMyc-SOX18 with anti-cMyc antibody in HUVECs. (B) Coverage of identified peptides of SOX18 and interacting proteins selected from ChIP-MS. (C) Amino acid sequence of DDX17, with the identified ChIP-MS peptides indicated in green. (D) Typical ALPHA-Screen curve for protein dilution optimization, showing SOX9-SOX9 and SOX18-SOX18. The presence of a peak (hook effect) demonstrates an interaction and represents the ideal protein concentration for consecutive binding studies. Proteins were expressed in the Leishmania tarentolee cell-free protein expression system. (E) Molecular structure of SOX18 inhibitor Sm4. (F) ALPHA-Screen concentration-response curves for SOX18 PPI disruption by Sm4. Data shown are mean±s.e.m.

SOX proteins activate individual target genes by recruiting specific interacting partners (Sarkar and Hochedlinger 2013), but only two protein-protein interactions for the SOXF group (SOX18-MEF2C and SOX17-OCT4) have been identified to date (Hosking et al. 2001, Jauch et al. 2011). We first mapped the SOX18 interactome (the network of SOX18 interacting partners), using a combination of unbiased proteomic technologies. Chromatin immunoprecipitation coupled to mass spectrometry (ChIP-MS) provided a first-pass screen for proteins associated with chromatin-bound SOX18 in human umbilical vein endothelial cells (HUVECs) (Mohammed et al. 2013), then, ALPHA-Screen resolved SOX18-dependent complexes into pairwise interactions using in vitro translated full-length proteins (FIG. 9A) (Mureev et al. 2009, Kovtun et al. 2011, Sierecki et al. 2013, Sierecki et al. 2014, Gambin et al. 2014). ChIP-MS analysis revealed 289 proteins, representing a variety of gene ontology (GO) classes of molecular function, that associate directly or indirectly with SOX18 (FIGS. 9B and 10A-C). To increase our chance of identifying direct interactors, we focused on proteins known to be nucleic acid and/or protein binding (FIG. 9B, purple). From this subset, we chose 8 known transcription factors, helicases, co-repressors, RNA binding and DNA-repair molecules (FIG. 10A,B). Using ALPHA-Screen, we observed that SOX18 interacts with itself, and also forms pairwise interactions with DDX1, DDX17, ILF3, STAT1, TRIM28, and XRCC5 (FIG. 9C, left column '+', and FIG. 10D).

In addition, we studied potential pairwise interactions of 6 well-known TFs able to regulate endothelial cell function (ESR1, NR2F2, RBPJ, SOX7, SOX17 and CTNNB1), and the only identified SOX18 protein partner MEF2C (Hosking et al. 2001). The well-characterized SOX9 homo-dimer (Bernard et al. 2003) was included as a positive control to validate the ALPHA-Screen signal (FIG. 10D). SOX18 was found to interact with all endothelial transcription factors tested, with the possible exception of SOX17 and CTNNB1, which showed a binding affinity below the arbitrary threshold (FIG. 9C, '−').

Figure 11:
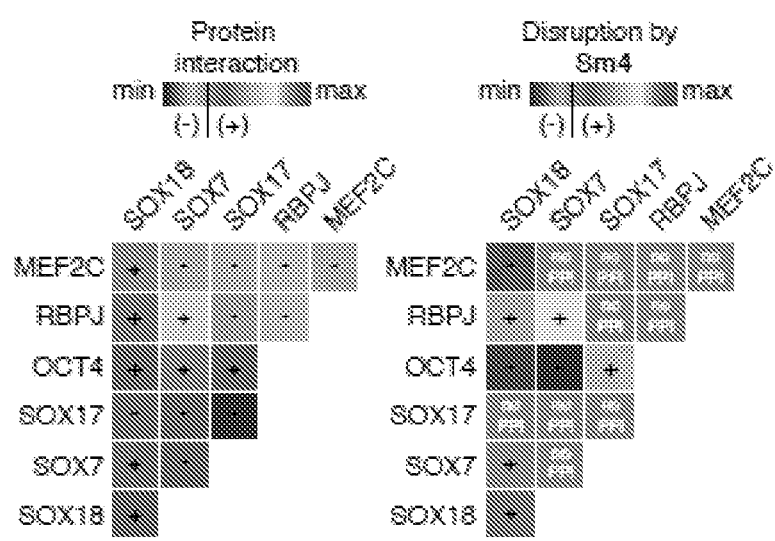
FIG. 11: Differential disruption of SOXF PPI by Sm4. The left panel shows a matrix of protein-protein interactions between SOXF, MEF2C and RBPJ and OCT4 as measured by ALPHAScreen. The right panel shows the effects of 50 uM Sm4 on PPIs (blue=no PPI/disruption, green/yellow=low PPI/disruption, orange/red=strong PPI/complete disruption, grey=PPI below threshold, Sm4 effect cannot be determined).

Having Identified an array of proteins able to interact with SOX18, we then went on to test the activity of a small-molecule compound, Sm4 (FIG. 10E), on these interactions. Sm4, derived from a natural product found in the brown alga Caulocystis cephalornithos, was identified in a high-throughput screen for potential SOX18 blockers (see Example 1). We found that Sm4 significantly disrupted 6 out of the 12 validated SOX18 interactions (FIG. 9C, right column), with IC50 values ranging from 3.3 μM for SOX18-SOX18 to 65.9 μM for SOX18-RBPJ dimers (FIGS. 9D and 10F). To assess a differential effect of Sm4 on the distinct SOXF members, we explored an additional set of PPIs between all three SOXF proteins and MEF2C, RBPJ and OCT4 (FIG. 11). Like SOX18, SOX7 is able to interact with RBPJ and SOX18 itself, both of which interactions are at least partially disrupted by Sm4. We further found that all three SOXF proteins can form a heterodimer with OCT4, whereas only the SOX17-OCT4 interaction is affected by Sm4. Importantly, neither SOX7 nor SOX17 have the capacity to form a homodimer, and thus this component of Sm4 mode of action is highly specific to SOX18-SOX18 interaction. Further corroborating this, SOX9 homodimerization was unperturbed by Sm4 at up to 200 µM (FIGS. 9C-D and 10D). These results show that Sm4 selectivity leans towards a subset of SOX18-associated PPIs, but has the capability to interfere with SOX7 or SOX17 protein partner recruitment. This feature of Sm4 is potentially advantageous in preventing SOXF redundancy mechanism (Hosking et al. 2009, Kim et al. 2016).

Figure 12:
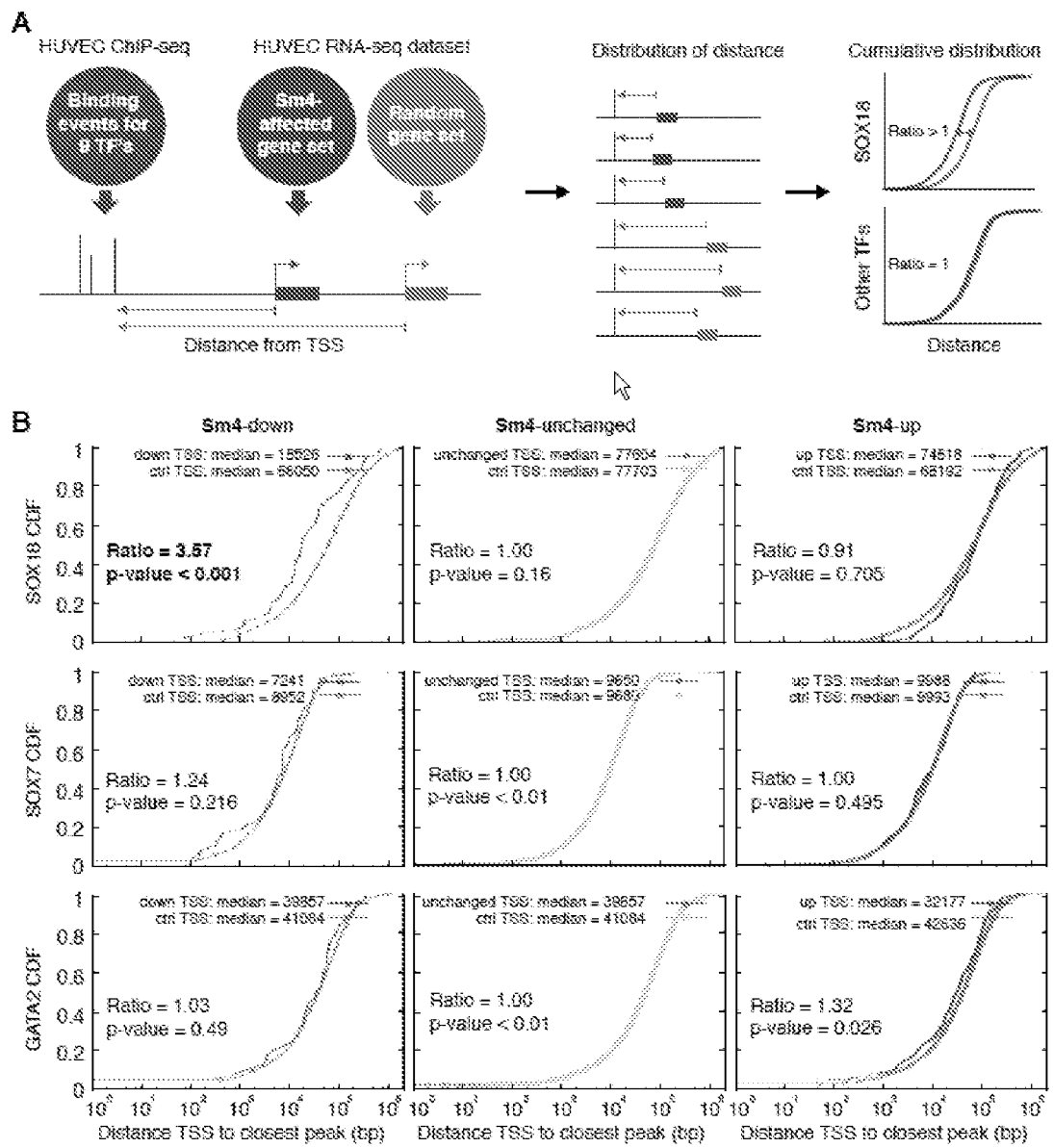
FIG. 12: Sm4 selectively affects SOX18 transcriptional output in vitro. (A) Schematic representation of the correlation analysis between genome-wide TF ChIP-seq data and Sm4 affected genes from transcriptomics data. The chromatin around the transcription start sites (TSS) of Sm4 affected genes (purple) was investigated for transcription factor binding peaks (grey), to calculate the "distance from TSS" to closest binding site for a given transcription factor. This distance from TSS was used as a proxy for the likelihood of transcriptional regulation, and thus make an association between Sm4 affected genes and transcription factors (Cusanovich et al., PLoS Genetics, 2014; Verbist et al., Drug Discov Today, 2015). Included in the analysis where the ChIP-seq peaks of SOX18 and SOX7, and of all transcription factors available from the Encode consortium (GATA2, c-FOS, c-JUN, CTCF, EZH2, MAX and c-MYC), performed in HUVECs. A random group of genes was analysed as a control distribution as would be found by chance. (B) Sm4 affected genes were grouped into down-regulated (Sm4-down), unaffected (Sm4-unchanged) and up-regulated (Sm4-up). The plots show the cumulative distribution of the distance between the TSS of Sm4 affected genes (purple line, absolute fold change ≥2) and the closest genomic location of binding sites for SOX18, and control transcription factors SOX7 and GATA2. The median distance from the TSS of differentially expressed genes to the nearest binding event of a given transcription factor was compared to the median distance that is expected by chance from a random gene set (green line). Sm4 down regulated genes are significantly closer (bold) to the SOX18 peaks, but not to SOX7 or GATA2 peaks.
Figure 13:
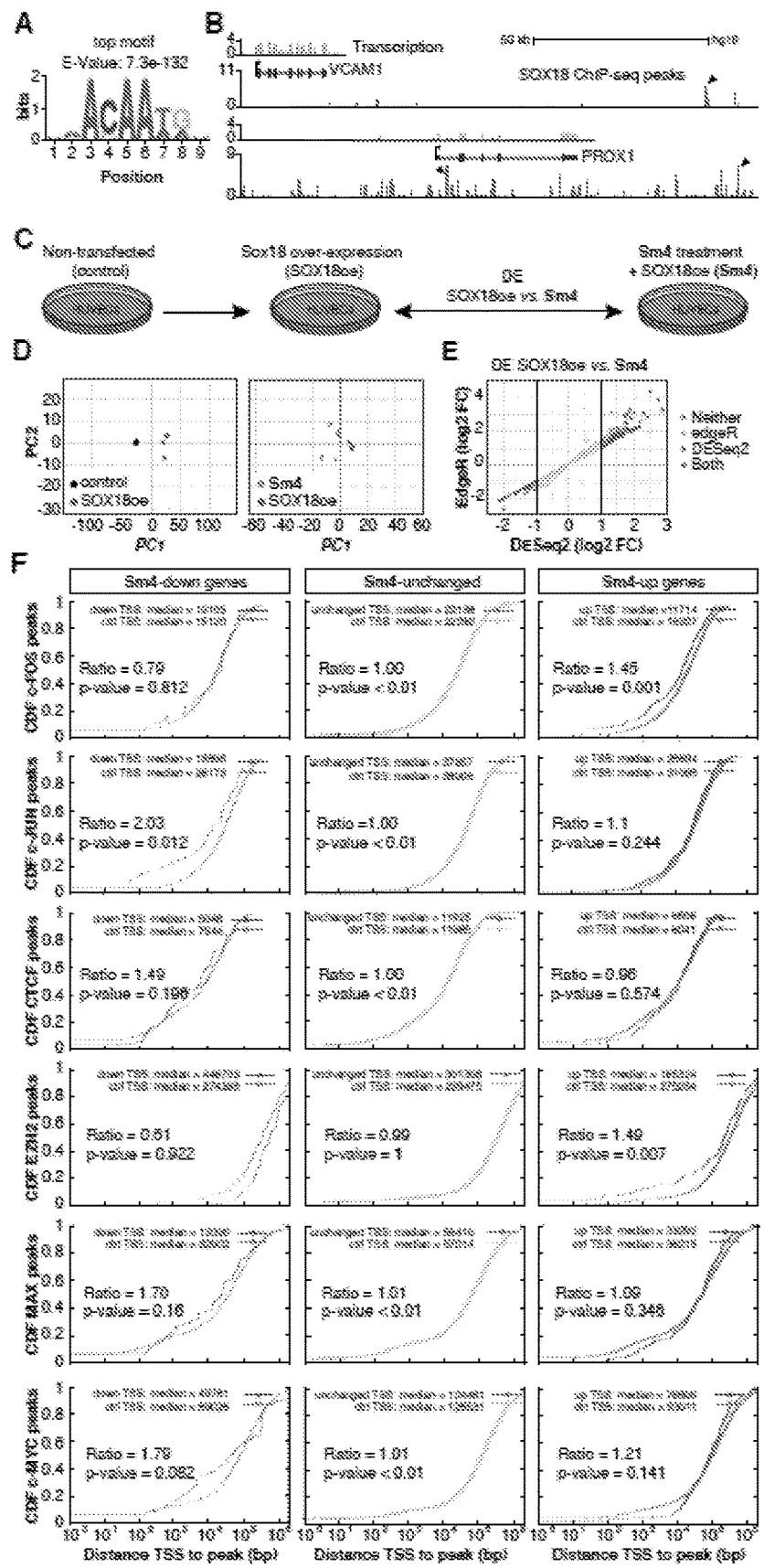
FIG. 13: Transcriptome-wide analysis of Sm4 selectivity in vitro. (A) Top motif identified from SOX18 ChIP-seq peaks (MEME software) performed in HUVECs. (B) UCSC browser view of representative ChIP-seq peaks (arrowheads) for known SOX18 target genes VCAM and PROX1. (C) Conditions for transcriptome-wide analysis of Sm4. Differential expression (DE) was calculated using DEseq2 in SOX18 overexpressing HUVECs, between vehicle DMSO (SOX18oe) and cells that received 25 μM Sm4 (Sm4) (D) Principal component analysis of quadruplicate RNA-seq samples. Replicates samples from same condition (control, SOX18oe, Sm4) cluster together. (E) Plot showing a comparison between DESeq2 and edgeR methods, marking significance of DE genes between SOX18oe and Sm4 conditions. Transcripts with a DESeq2 Log 2 Fold Change ≥1 or ≤−1 (dashed lines) were considered for further analysis. (F) The distance between Sm4 affected genes (purple) and the closest genomic location of binding sites a given transcription factor, plotted as cumulative distribution. The median distance from the TSS of differentially expressed genes to the nearest binding event of a transcription factor binding event was expressed as a ratio over the median distance that is expected by chance (random genes, green).

To assess how SOX18 PPI disruption translates into transcriptional dysregulation, we next performed a combination of genome-wide RNA-seq and ChIP-seq analyses in HUVECs. The most common binding motif identified from the SOX18 ChIP-seq peaks corresponds to the previously reported SOX motif 5'-AACAAT-3' (FIG. 13A) and the validity of this ChIP-seq dataset was further confirmed by GO term analysis and identification of known SOX18 target genes such as Prox1 and Vcam1 (FIG. 13B) (Francois et al. 2008, Hosking et al. 2004). We compared the global transcriptional effect of Sm4 treatment to DMSO control in SOX18 overexpressing cells (FIG. 13C-E), and overlaid this list of differentially expressed genes with the SOX18 ChIP-seq dataset. Using this overlay, we calculated the distance between the transcription start site (TSS) of a gene and a TF binding event, as a proxy for the likelihood of direct transcriptional regulation. To be able to analyse how this distance is altered by Sm4, we established a reference distance between the TSS of a random gene set and SOX18 binding events (FIG. 12A). In parallel, we performed the same analysis for SOX7 (generated in-house), and for all 7 transcriptional regulators available from the ENCODE consortium (GATA2, c-FOS, c-JUN, CTCF, EZH2, MAX, c-MYC). This allowed us to distinguish between transcriptional targeting of SOX18 and potential off target effects on other endothelial specific transcription factors.

Figure 14:
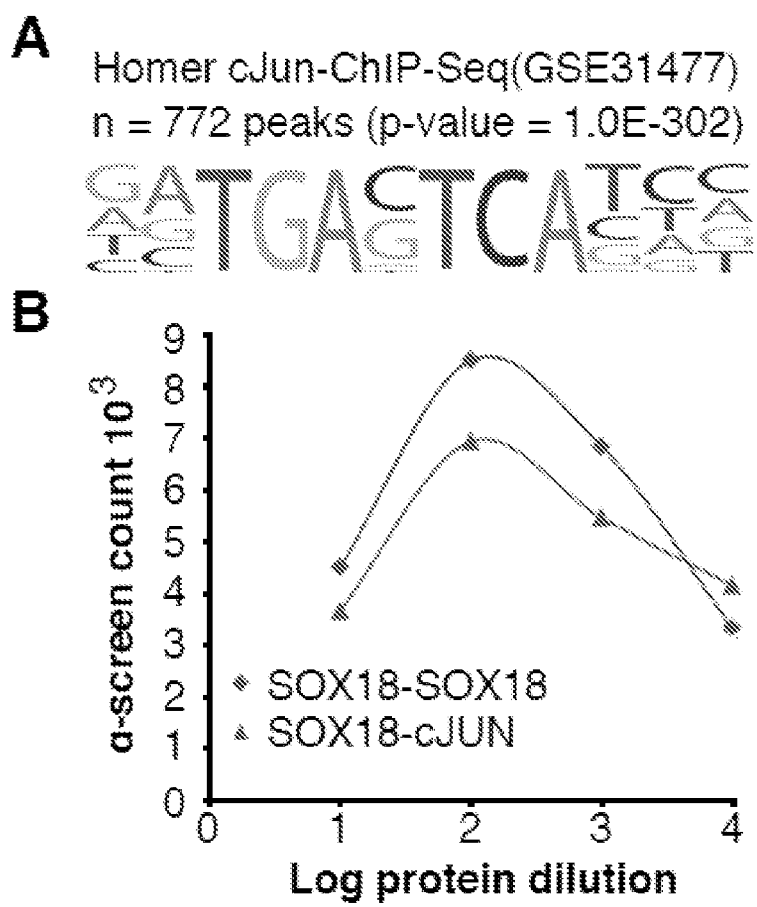
FIG. 14: c-JUN motifs are enriched in SOX18 binding sites. (A) HOMER motif analysis on SOX18 ChIP-seq peaks revealed an enrichment of the c-JUN motif 5'-TGAC/GTCA-3'. (B) ALPHA-Screen binding curve for SOX18-c-JUN and SOX18-SOX18 (positive control), demonstrating that c-JUN has the capacity to directly interact with SOX18 in vitro. Proteins were expressed in the Leishmania tarentolae cell-free protein expression system.

The cumulative SOX18 peak-to-TSS distance demonstrated that, overall, SOX18 peaks are 3.6 fold closer (p-value <0.001) to the TSS of Sm4 down-regulated genes than to randomly distributed TSSs (FIG. 12B, top left). These results are an indirect indication that the Sm4 affected genes are dysregulated through a specific effect on SOX18 transcriptional activity. This correlation was not observed for 7 of the other transcription factors tested (FIGS. 12B and 13F), signifying that Sm4 does not have an off-target effect on these TFs activity. Interestingly, the TSS of Sm4 down-regulated genes were 2.05 fold closer to c-JUN binding events (p-value=0.011, Supplementary file 1c). Although only mildly significant, this could suggest possible co-regulation by SOX18 and c-JUN on this subset of Sm4 down-regulated genes. Indeed, analysis of known motifs in SOX18 ChIP-seq peaks revealed an over-representation of c-JUN binding motifs (3.23% of SOX18 peaks, p-value=1e-302) and ALPHA-Screen analysis further established that SOX18 and c-JUN could physically interact (FIG. 14). We found that the expression levels of the other TFs tested were unaltered by Sm4 treatment. This is an important observation because it demonstrates that there was no bias introduced by an off-target modulation of the transcript levels for these transcription factors in presence of Sm4.

Figure 15:
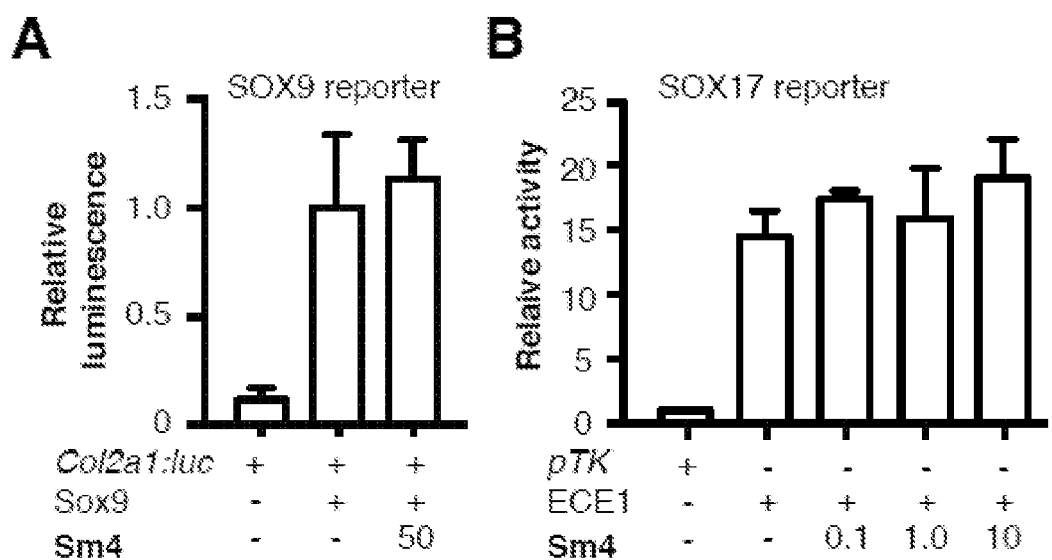
FIG. 15: Sm4 does not interfere with SOX9 or SOX17 activity in vitro. (A) Cell based reporter assay for SOX9 homodimer activity. COS-7 cell were transfected with Sox9 and Col2a1:luc reporter construct. Sox9 overexpression caused a >8-fold induction of Col2a1 activation. No change was observed at high concentration of Sm4. (B) Cell based reporter assay for SOX17 activity (Robinson et al. 2014). Bovine Aortic Endothelial Cells (BAECs) were transfected with pTK-β-gal (pTK) or ECE1-TK-β-gal (ECE1) reporter, measuring endogenous activity of SOX17 (ECE1-only). No change was observed at any of the tested concentration. Numbers on x-axis are [Sm4] in μM.

To address the issue of potential transcriptional off-target effects of Sm4 on SOX TF family members we focused on closely related SOXF and SOXE proteins. Sm4 did not affect the transcriptional activity of either SOX17 or SOX9 proteins at any tested concentration (≤50 µM) in cell-based reporter assays (FIG. 15) (Robinson et al. 2014, Lefebvre et al. 1997). Together, these results provide strong evidence that Sm4 selectively targets SOX18-mediated transcription over other key endothelial transcription factors and SOX proteins.

Figure 16:
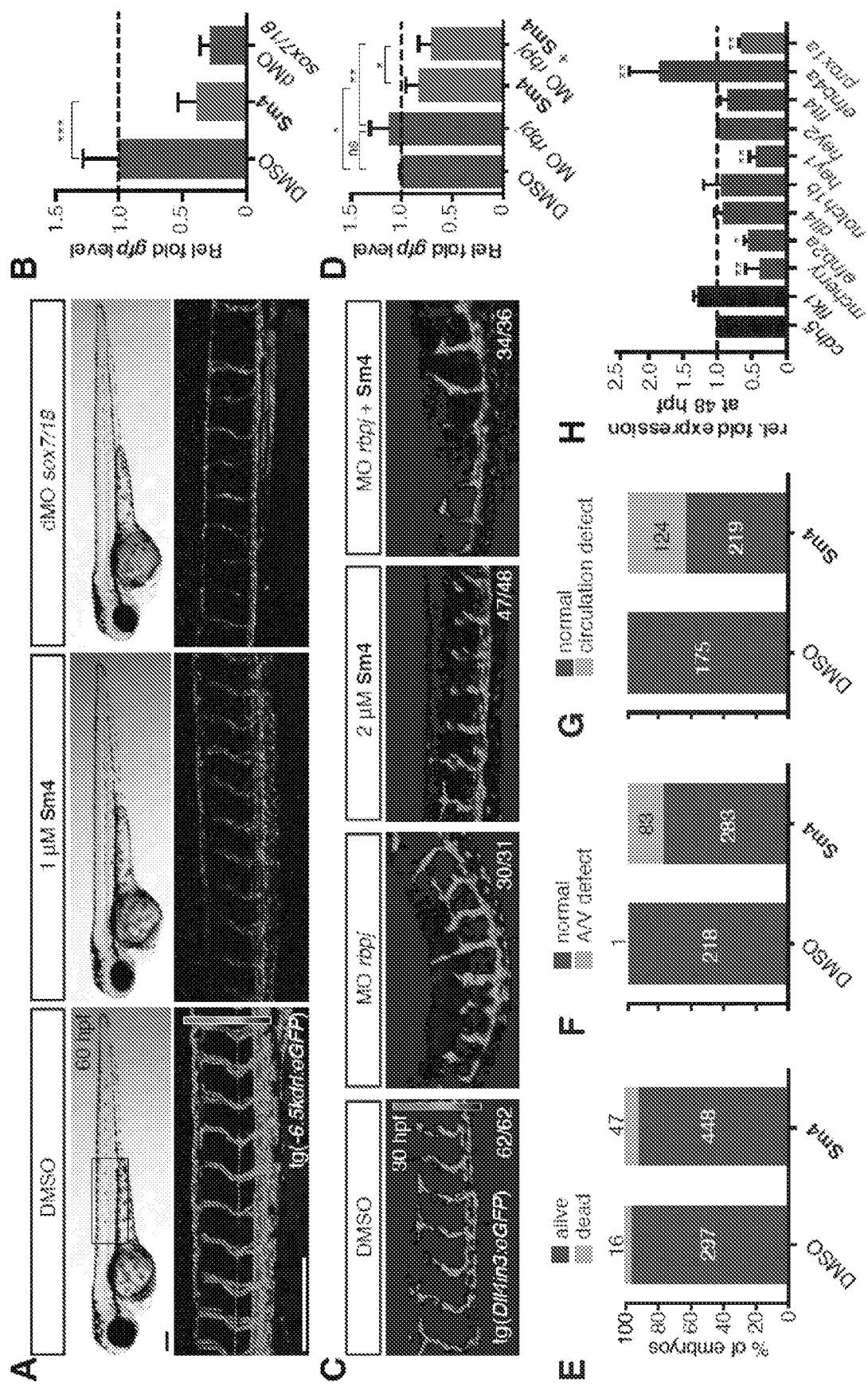
FIG. 16: Sm4 blocks SoxF transcriptional activity in vivo. (A) Lateral brightfield (top) and fluorescent (bottom) images of 60 hpf zebrafish larvae carrying the tg (−6.5kdrl:eGFP) SoxF reporter. Treatment was initiated at late stage (20 hpf) with either DMSO (negative control) or 1 μM Sm4, or larvae were injected with morpholinos against both sox7 and sox18 (dMO sox7/18). Fluorescence intensity is shown as heatmap. Scale bar 200 μm (B) qRT-PCR analysis on gfp transcripts levels in treated tg (−6.5kdrl:eGFP) larvae and sox7/18 morphants, showing reduction of activity on this transgene. (C) Lateral view of zebrafish larvae carrying the tg (DlI4in3:eGFP) SoxF/Notch reporter that harbors multiple binding sites for Rbpj and SoxF transcription factors. Larvae were injected with a morpholino against rbpj and/or treated with 2 μM Sm4 from 13 hpf. (D) qRT-PCR analysis on gfp transcripts in tg (DlI4in3:eGFP) larvae, showing repression of combined SoxF/Notch activity in the Sm4-treated larvae. (E) Quantitation of embryonic lethality in larvae, treated with Sm4 or DMSO control from early stage (16 hpf) until 72 hpf. (F) Penetrance of vascular phenotype (arteriovenous shunting) in 48 hpf larvae treated with 1.5 µM Sm4 from 16 hpf. (G) Penetrance of circulation defect in 48 hpf larvae treated with 1.5 µM Sm4 from 16 hpf. (H) qRT-PCR analysis of endogenous endothelial transcript levels at 48 hpf in larvae treated with 1.5 µM Sm4 at 16 hpf, relative to DMSO control (dotted line). Data shown are mean±s.e.m. *p<0.05, *p<0.01, *p<0.001.

To investigate whether Sm4 is also able to perturb Sox18 transcriptional activation in vivo, we used the tg (−6.5kdrl:eGFP) transgenic zebrafish reporter line, previously validated as a readout for the combined activity of Sox7 and Sox18 (Duong et al. 2014). We treated these larvae at 20 hours post fertilization (hpf) and observed that Sm4 treatment significantly reduced SOX18-dependent egfp transcript levels (61%), similar to the effects of combined sox7/18 depletion using morpholino oligonucleotides (MO) (FIG. 16A,B). Importantly, these zebrafish embryos developed normally and we found no evidence of toxicity.

Figure 17:
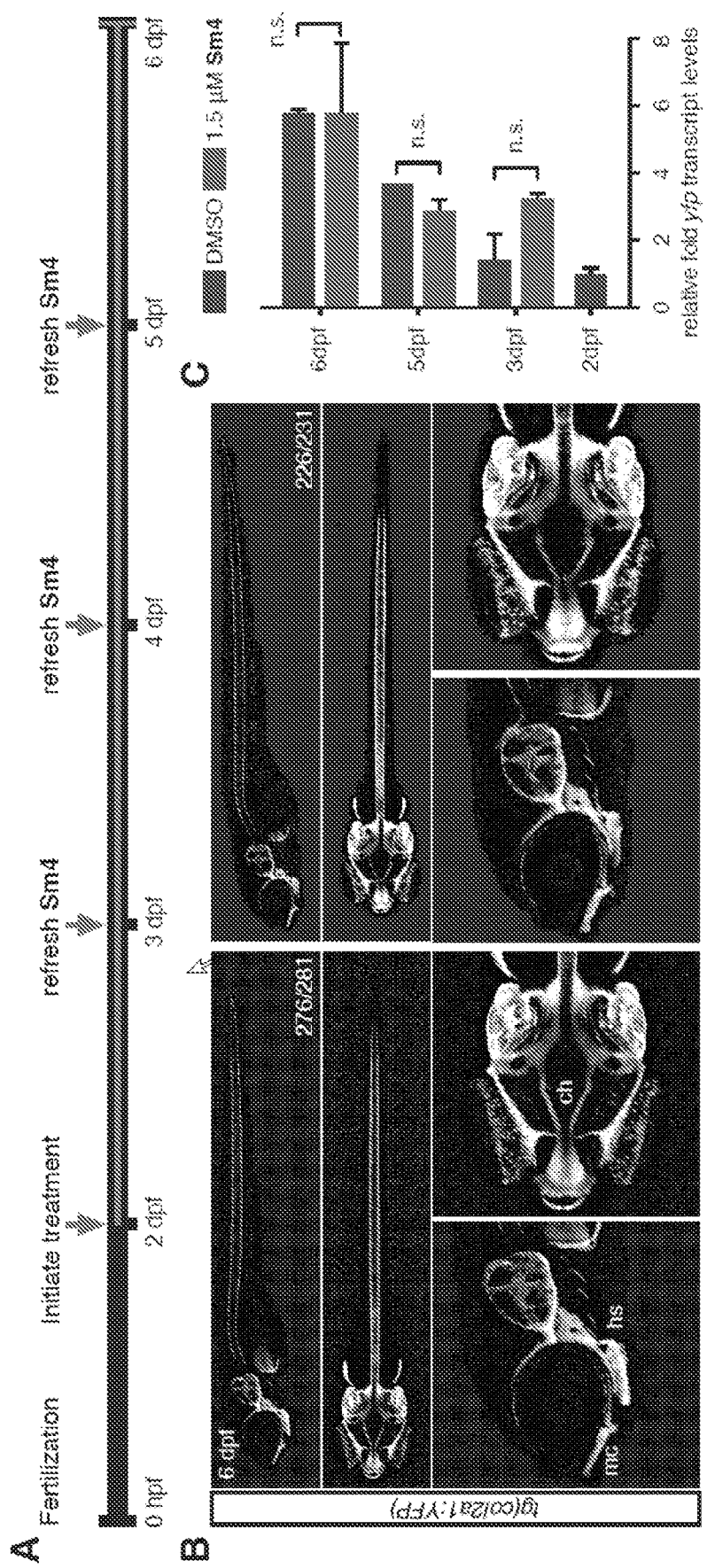
FIG. 17: Sox9 activity is not perturbed by treatment in vivo. (A) Timeline of treatment: Zebrafish larvae were treated continuously for 4 days during chondrogenesis. Medium was refreshed daily throughout the experiment to maintain Sm4 levels. (B) tg (col2a1:YFP) Sox9 reporter larvae marking cartilage (Mitchell et al. 2013). YFP levels were unaffected in presence of Sm4, and no changes in chondrogenesis were observed. mc: Meckel's cartilage, ch: ceratohyal, hs: hyosymplectic. (C) qRT-PCR of yfp transcript levels in DMSO control and Sm4 treated larvae at a series of stages throughout chondrogenesis.

We then used a second transgenic zebrafish reporter line tg (Dll4in3:eGFP), which harbours a regulatory element located in the intron 3 of dll4 gene. The activity of this Dll4in3 enhancer does not fully recapitulate the endogenous dll4 expression (Wythe et al. 2013, Sacilotto et al. 2013) (Wythe et al 2013 and Sacilotto et al 2013), but it does provide a useful tool to study the combinatorial activity of Sox7, Sox18 and the Notch effector Rbpj. Combined genetic interference with sox7, sox18 and rbpj has been shown to abolish Dll4in3 activation, while single or double MO knockdowns have a much milder effect (Sacilotto et al. 2013). This mild repressive effect was recapitulated by treatment with Sm4 alone (FIG. 16C,D). In addition, when rbpj MO injections at suboptimal dose were combined with Sm4 treatment, the repressive effect was significantly increased by 11.5% (FIG. 16C,D). These data show that Sm4 interferes with Sox7/18 and Rbpj co-ordinated activation of the Dll4in3 enhancer. As a negative control in vivo, we used the Sox9-dependent tg (col2a1:yfp) reporter line, and observed that continuous Sm4 treatment between 2 and 6 days post fertilization did not perturb the transcriptional activity of Sox9 or the process of chondrogenesis (FIG. 17). Together, this supports the proposed mechanism of action for Sm4 as a selective SOX18 inhibitor in vivo.

Figure 18:
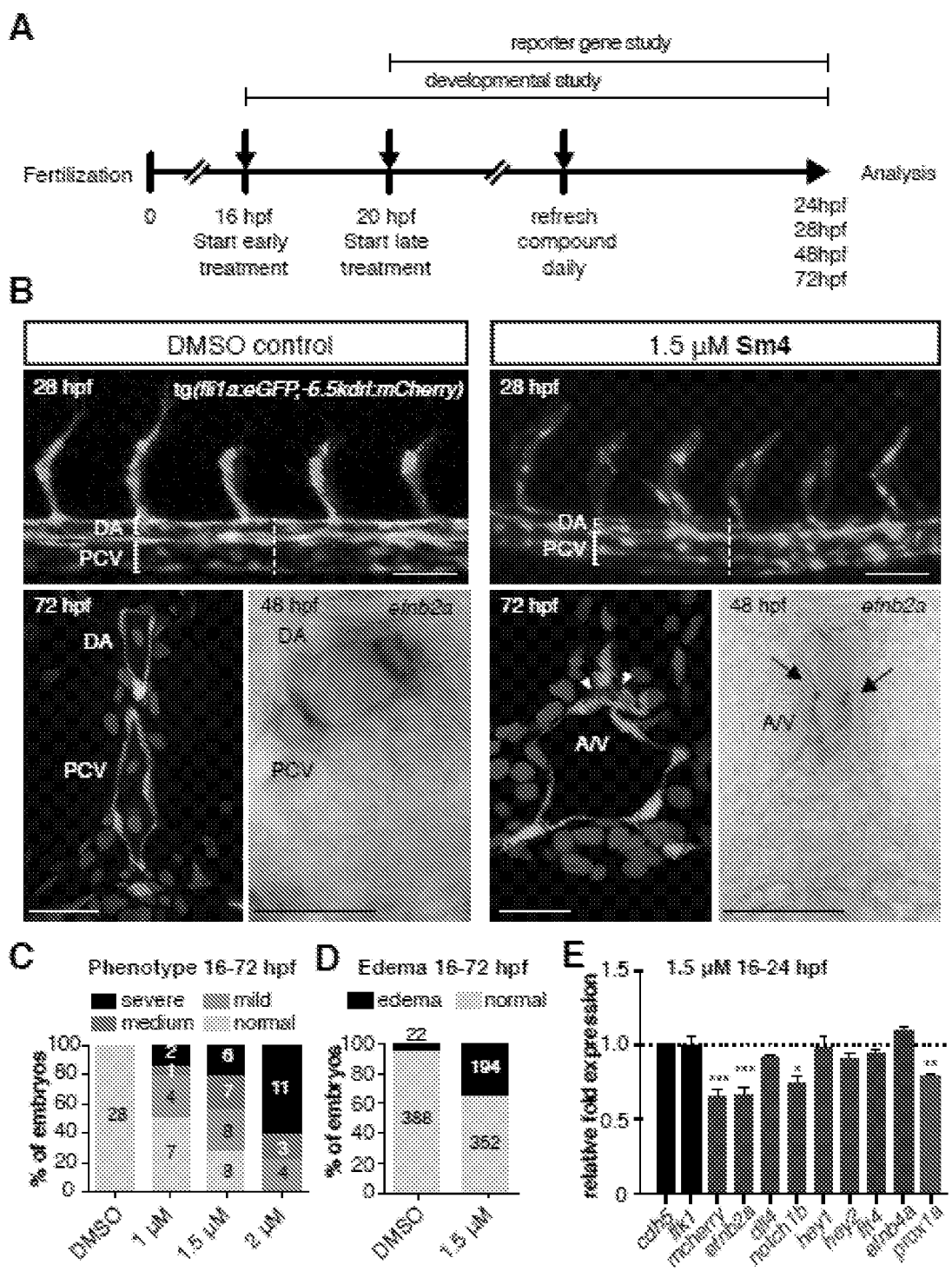
FIG. 18: Sm4 interferes with SoxF activity in vivo. (A) Timeline of Sm4 treatment in zebrafish larvae. Treatment for SOXF reporter gene studies was initiated at 20 hpf, while for the phenotypic studies treatment was initiated at precedes that for, to act during the right developmental window for arteriovenous specification. (B) Lateral view and transverse section of the trunk region of DMSO control and Sm4-treated tg (fli1:eGFP, −6.5kdrl:mCherry) larvae. Control DMSO larvae formed a distinctly separated dorsal aorta (DA) and posterior cardinal vein (PCV). In Sm4-treated larvae, the DA was constricted and/or fused to the PCV (arrowheads). Whole mount in situ hybridization against arterial marker efnb2a shows reduced expression and compromised formation of the DA and in Sm4-treated larvae at 48 hpf (arrows). Sections were DAPI stained (in blue). Scale bar brightfield: 0.5 mm, fluorescent and in situ 25 µm. (C) Concentration dependent effect of Sm4, showing quantitation for predominant phenotype at 72 hpf: mild (tail curvature), medium (dilation of the PCV) or severe (arteriovenous defect and/or circulation defect). Indicated timeframe refers to Sm4 treatment window and endpoint. (D) Quantitation of cardiac edema frequency in larvae treated with Sm4 (1.5 µM). (E) qRT-PCR analysis of Sox18 dependent −6.5kdrl: mCherry and endogenous endothelial transcript levels in Sm4-treated larvae relative to DMSO control (dotted line), showing effect on arterial and venous markers at 24 hpf. All expression levels were normalized to expression of endothelial marker cdh5. Data shown are mean±s.e.m. *p<0.05, p<0.01, *p<0.001.

To further demonstrate the small molecule inhibition of Sox18 function in vivo, we next investigated whether Sm4 treatment would be able to cause a vascular phenotype, similar to that of sox7/sox18 genetically disrupted zebrafish (Hermkens et al. 2015). This phenotype is characterised by an arteriovenous specification defect, with reduced expression levels of arterial markers (Cermenati et al. 2008, Herpers et al. 2008, Pendeville et al. 2008). We treated zebrafish larvae harbouring the arterial/venous reporter tg (fli1a:eGFP, −6.5kdrl:mCherry) with 1.5 µM Sm4 during the relevant developmental window, starting from 16 hpf (FIG. 18A). These larvae acquired an enlarged posterior cardinal vein (PCV) at the expense of the dorsal aorta (DA) (FIGS. 16E-G and 18B), with arteriovenous shunts and incomplete trunk circulation (FIG. 18C,D). qRT-PCR analysis of blood vascular markers at 24 and 48 hpf revealed a significant dysregulation of arterial and venous genes in Sm4-treated conditions compared to DMSO, particularly efnb2a, hey1 and efnb4a (FIGS. 16H and 18E).

Due to SoxF redundancy in arteriovenous specification, an A/V malformation phenotype is typically only observed in double loss of Sox7 and Sox18 function. Since Sm4 appeared to partially interfere with Sox7-Rbpj and Sox7-Sox18 PPIs in vitro, we turned to a Sox7 specific phenotype to assess whether this TF activity was inhibited by Sm4 in vivo. The hallmark of sox7 genetic disruption is a short circulatory loop in the head formed by the lateral dorsal artery (Mohammed et al. 2013), resulting in perturbed facial circulation (Hermkens et al. 2015). In presence of Sm4, we observe minor malformation to the LDA reminiscent of a partial Sox7 loss of function phenotype. However, the blood circulation in the head is unaffected in Sm4-treated larvae, signifying that a short circulatory loop has not fully formed. This phenotype supports of the conclusion that Sox7 activity is only partially affected in presence of the small compound. Overall, these results are congruent with the genome-wide inhibitory effects observed in vitro, demonstrating that Sm4 selectively interfered with the transcriptional activity of Sox18 and SoxF-mediated vascular formation in vivo.

Figure 19:
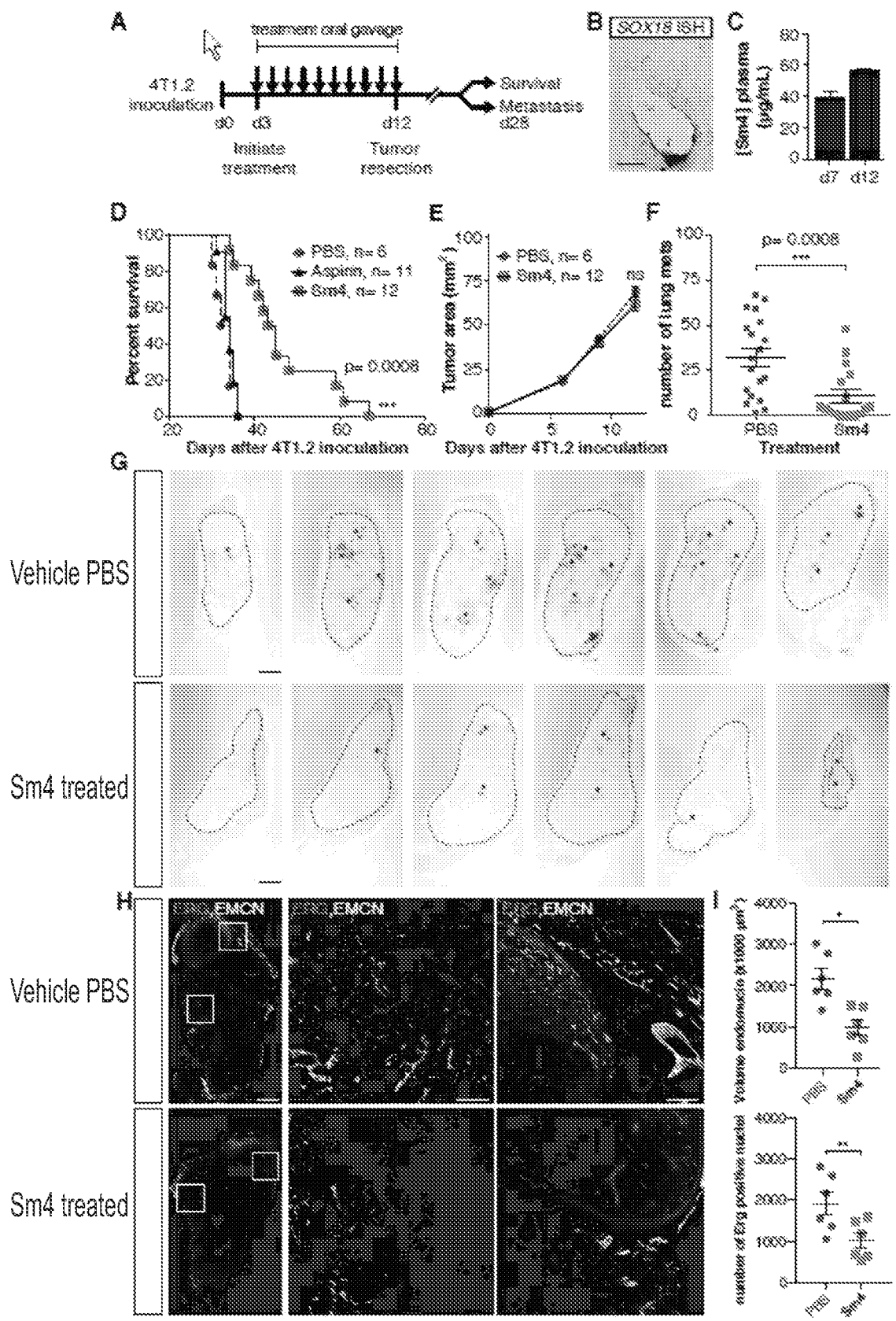
FIG. 19: Metastasis and tumor vascularization is suppressed by Sm4 treatment. (A) Timeline of mouse model for breast cancer metastasis. 4T1.2 tumor was inoculated at day 0, and resected at day 12. Sm4 (25 mg/kg/day), Aspirin (25 mg/kg/day) or vehicle control (PBS), was administered orally on a daily basis from day 3 to day 12. Independent experiments were carried out to assess survival and metastatic rate. (B) Blood plasma concentrations of Sm4 during the course of the treatment scheme (day 7 and day 12) indicate good systemic delivery of the drug. (C) Expression of SOX18 in the vasculature of the tumor as shown by in situ hybridization. Scale bar 100 µm. (D) Survival of the mice was monitored (n=6-12 mice per group). Improved survival in Sm4-treated mice over both vehicle control and aspirin was analysed by Log-rank test (p<0.001). (E) No significant differences were found in tumor size at any stage. (F) Metastatic tumor nodules on the surface of the lungs were quantified at day 28, before any of the vehicle control or Sm4-treated animal had succumbed to the cancer burden. Data shown are mean±s.e.m of 12-14 mice per group. (G) Vascular density was investigated on 300 µm sections of whole tumors. Bright field images show the overall morphology of the tumor (outlined by dashed line) and presence of red blood cells, marking the main blood vessels and haemorrhagic areas (asterisks). Scale bar 1 mm. (H) Double immunofluorescence staining for endothelial specific markers ERG and Endomucin (EMCN) reveals the vascular patterning and penetration in the intra- and peri-tumoral regions. Left: whole tumor section (scale bar 1 mm), middle and right: blow-up of boxed regions (scale bar 200 µm). (1) Quantitation of EMCN volume (blood vessel density) and ERG-positive nuclei (number of endothelial cells) of n=6 tumours per condition. Each data point represents the average of 3-4 representative regions (boxed areas in panel H) per tumor. Mean±s.e.m for both conditions are shown. *p<0.05, **p<0.01. (J) Similar to Panel (D) above, survival of the mice was monitored after administration with either vehicle or increasing concentrations of Sm4 (i.e., 5 mg/kg, 10 mg/kg, 25 mg/kg and 50 mg/kg) (n=6-12 mice per group). This experiment determines that Sm4-improved survival is dose dependent and this result suggests specific on-target engagement in vivo.

As a final demonstration of the anti-angiogenic potential of Sm4 in a therapeutically relevant setting, we next assessed its efficacy in a preclinical model of breast cancer. BALB/c mice were inoculated with highly metastatic 4T1.2 mammary carcinoma cells into the mammary fat pad, and 3 days were allowed for the engraftment of the tumor, after which treatment was initiated with either 25 mg/kg/day of Sm4, aspirin or vehicle PBS (FIG. 19A). Aspirin was chosen as a negative control because of the structural similarity to Sm4. Daily treatment was maintained for a duration of 10 days, after which the primary tumor was resected and effects on disease latency were monitored (FIG. 19A). As an indirect indication of target engagement, we first confirmed the expression of Sox18 in the 4T1.2 tumor vasculature by in situ hybridization (FIG. 19B). We next went on to measure Sm4 bioavailability during the course of the treatment. Sm4 was consistently detected in blood plasma at 2 different time points, with a mean concentration increasing over time from 38.3 µg/mL to 55.2 µg/mL (FIG. 19C).

PBS vehicle- or aspirin-treated mice succumbed to the 4T1.2 tumor burden with a median latency of 33 and 34 days respectively (FIG. 19D), whereas Sm4-treated mice had a significant increase in their overall survival with a median latency of 44 days (p-value <0.01). As shown in the assessment of Sm4 dose response of FIG. 20I, increasing the concentration of Sm4 resulted in further improvements to overall survival of 4T1.2 inoculated mice. By way of example, treatment of mice with 50 mg/kg Sm4 resulted in a median latency of 73 days versus a median latency of 40 days for vehicle treated mice.

To further investigate what could cause such an effect, the size of the tumors was monitored during the treatment, as well as the formation of spontaneous lung metastases. While the size of the primary tumor was unchanged by Sm4 treatment (FIG. 19E), we found a 67% reduction in the mean number of lung metastases at day 28 after tumor inoculation (FIG. 19F).

Figure 20:
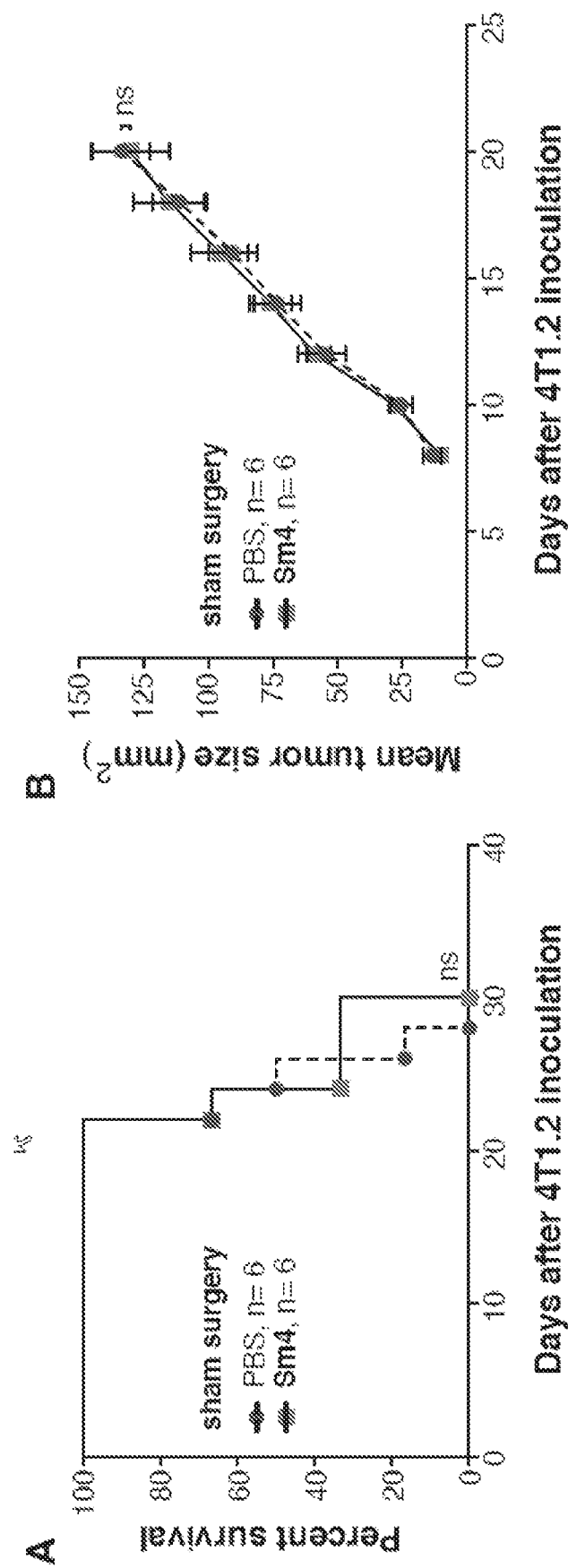
FIG. 20: Sm4 efficacy is not a result of surgery-induced inflammation. 4T1.2 tumor was inoculated at day 0, and surgery was performed at day 12, without resecting the tumor (n=6). (A) Survival (n=6) was monitored in PBS vehicle control mice and Sm4-treated mice (25 mg/kg/day). No differences were observed (Log-rank test). (C) No significant differences were found in tumor size at any stage before or after sham surgery.

To rule out any contribution by an inflammatory response as a result of surgery, we replicated the study by performing a sham surgery, without excising the tumor (FIG. 20A,B). This approach confirmed that during the post-surgical period, primary tumor growth was unperturbed by Sm4 treatment and demonstrated that the combined effects of Sm4 with surgery-induced inflammation is unlikely to be responsible for the increased survival.

Figure 21:
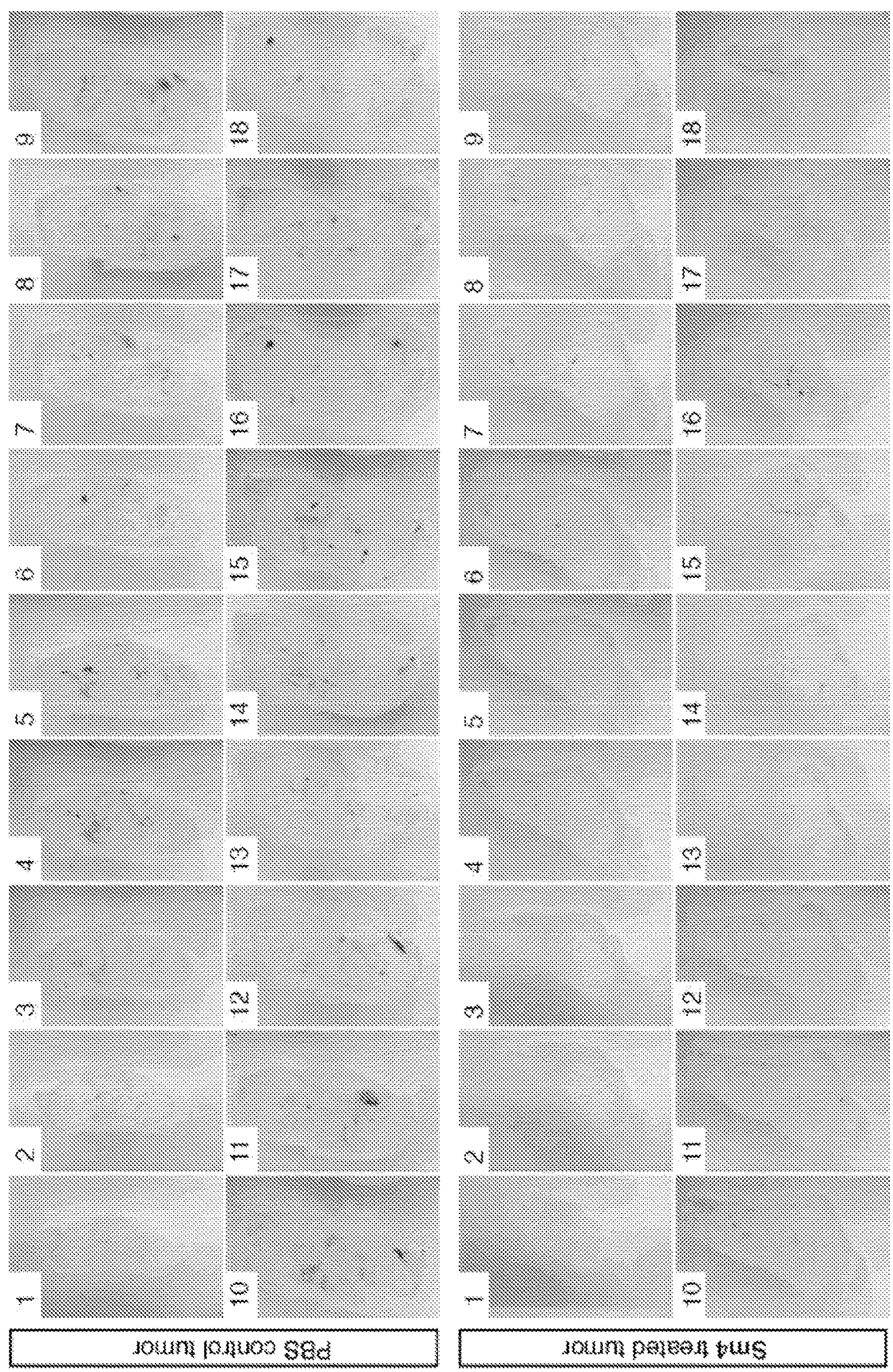
FIG. 21: Penetrance of blood vessels into 4T1.2 tumors is impaired by Sm4. Brightfield images of serial vibratome sections (300 µm) from a whole 4T1.2 mammary tumor for mice treated with PBS vehicle or Sm4. Main blood vessels and haemorrhagic areas are distinctive in red.
Figure 22:
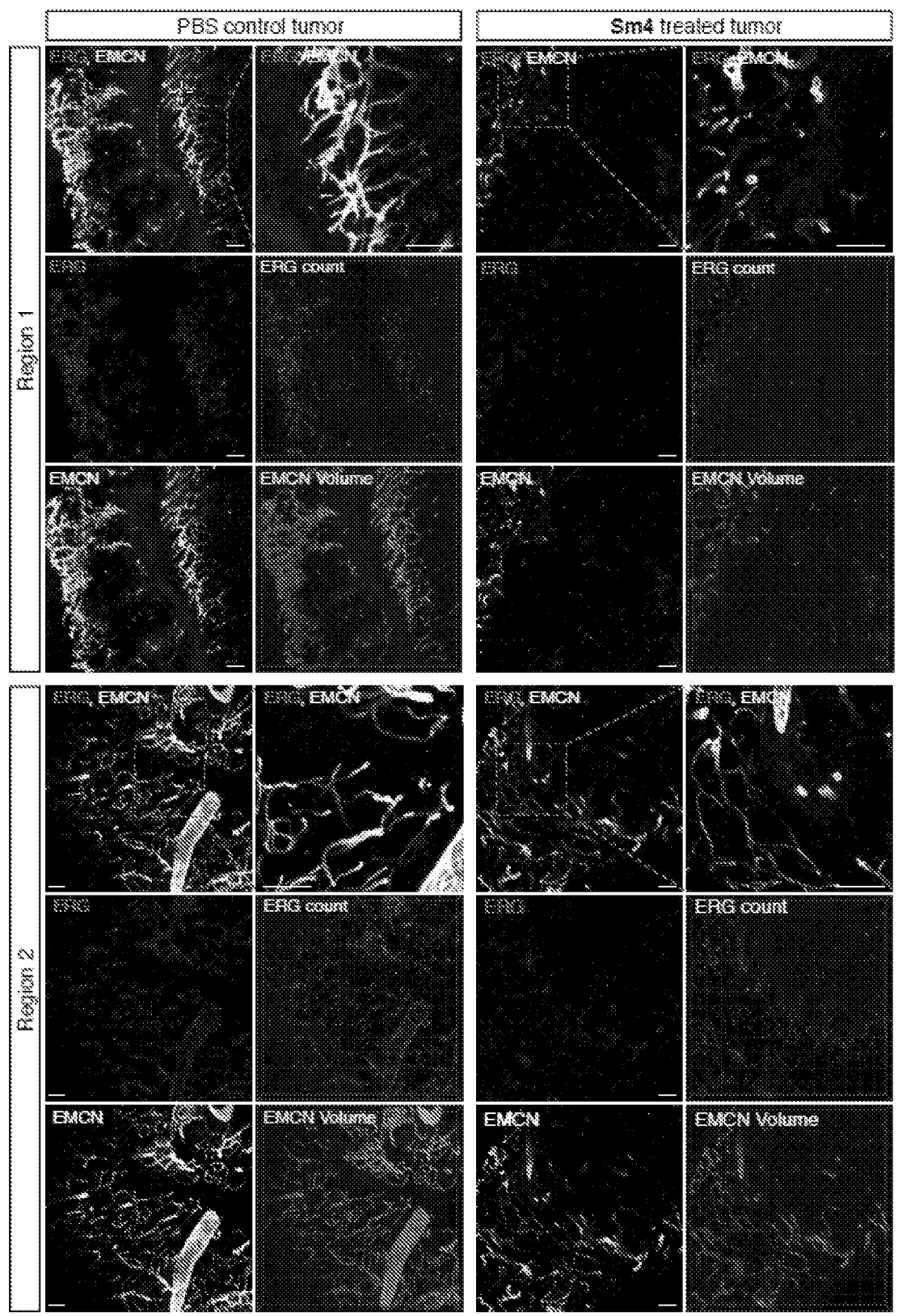
FIG. 22: Sm4-treated mice have decreased tumor vascular density. Immunofluorescent staining for ERG and Endomucin (EMCN) on tumor sections. Two representative regions for both vehicle PBS and Sm4 are shown. Detailed blow-up shows distinct nuclear staining for ERG, and membranous endothelial staining for EMCN. Quantitation of endothelial cells number and vascular volume was performed in Imaris on images with identical XYZ dimensions. Thresholds were chosen to accurately capture total EMCN+ vasculature and total ERG+ nuclei (ERG count and EMCN volume in yellow).
Figure 23:
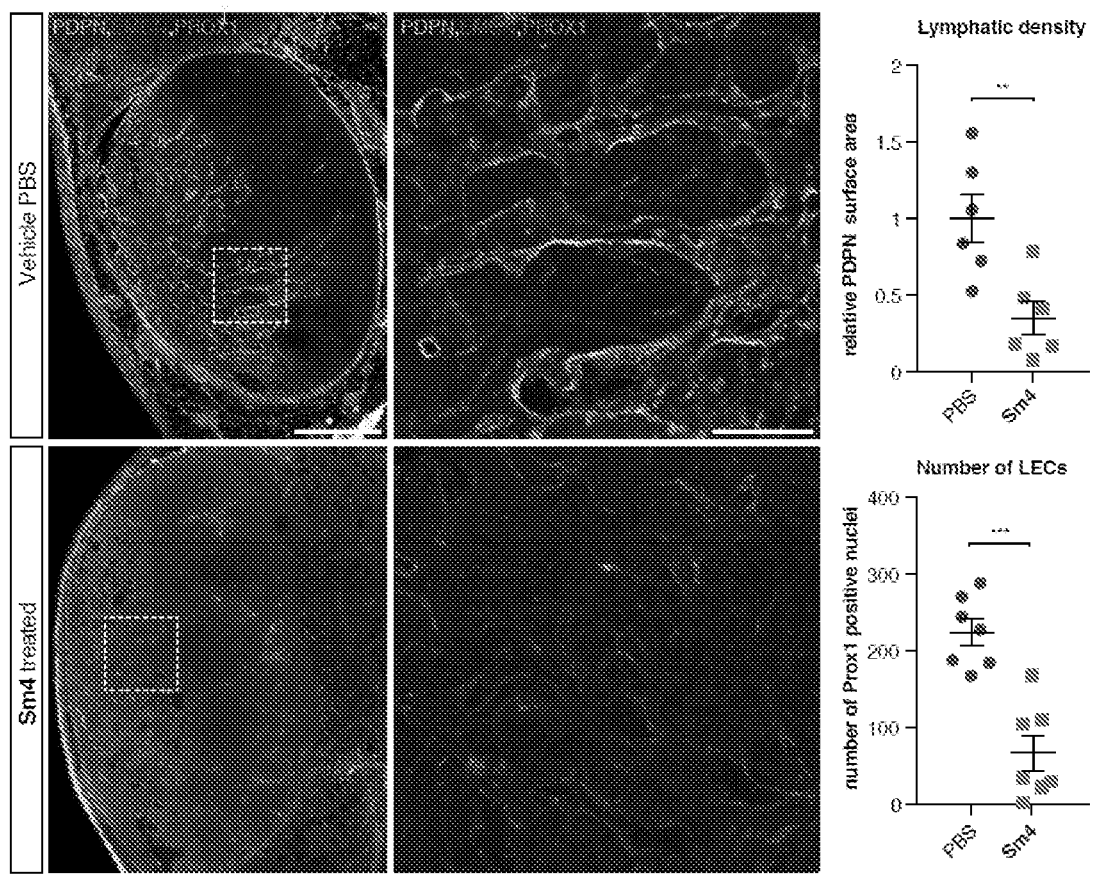
FIG. 23: Sm4 treatment disrupts tumour-induced lymphangiogenesis. Lymphatic vessels images of serial vibratome sections (200 µm) from a whole 4T1.2 mammary tumor for mice treated with PBS vehicle or Sm4 (25 mg/kg/day). Immunofluorescence for lymphatic specific markers PROX1 and Podoplanin (PDPN) and vascular EC marker Endomucin (EMCN) reveals the vascular patterning and penetration in the intra- and peri-tumoral regions. Whole tumor section for the control group (top panels), and for Sm4 treated group (bottom panels). Quantitation of PDPN+ lymphatic vascular area (density, top graph) and PROX1+ nuclei (number of lymphatic endothelial cells, bottom graph) of n≥6 tumours per condition. Scale bar left: 0.5 mm, right: 0.1 mm. Mean±s.e.m for both conditions are shown. *p<0.01, *p<0.001.

In order to establish a correlation between the metastatic rate and a tumor induced vascular response, we investigated the blood vessel density in the intra-tumoral and peri-tumoral regions (FIGS. 19G and 21). Whole tumors were sectioned, and brightfield microscopy revealed an overall reduction in blood vessel coverage, as indicated by the presence of red blood cells (FIG. 19G, asterisks). Further analysis using immunofluorescent staining for endothelial cell markers ERG (nuclear) and Endomucin (EMCN, membranous), showed a significant decrease in the number of endothelial cells (48%, p-value <0.05), as well as the volume of the blood vessels (55%, p-value <0.01) in the tumors of Sm4-treated mice (FIGS. 19H,I and 22). Using lymphatic specific markers PROX1 and podoplanin (PDPN), we also assessed the effect of Sm4 on the tumor induced lymphangiogenic response, and found that the density of the tumor associated lymphatic vessels was greatly reduced (65%, p-value <0.01) in treated conditions, as well as the number of lymphatic endothelial cells (70%, p-value <0.001) (FIG. 23). This lymphatic response to Sm4-treatment is consistent with that of SOX18 loss of function during lymphatic spread of solid cancers (Duong et al. 2012) Together, this demonstrates that Sm4 improved the outcome of induced breast cancer by interfering with tumor-induced neovascularization and associated metastasis.

Induction of angio- and lymphangiogenesis is a hallmark of solid cancer, and is a critical step towards enabling tumor metastatic dissemination. Conventional approaches to target transcription factors have focused on interfering with oncogenes that are dysregulated to promote tumor cell transformation (Gormally et al. 2014, Illendula et al. 2015, Moellering et al. 2009, Zhang et al. 2012). Here, we validate a novel complementary strategy that relies on targeting a developmental transcription factor from the host vasculature that can facilitate metastatic spread. Our results provide a proof of concept that targeting the transcription factor SOX18 with Sm4 is an effective molecular strategy to interfere with the metastatic spread in a pre-clinical model of breast cancer.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

Anders, S., P. T. Pyl, and W. Huber. 2015. "HTSeq-a Python framework to work with high-throughput sequencing data." Bioinformatics 31 (2):166-9. doi: 10.1093/bioinformatics/btu638.

Bernard, P., P. Tang, S. Liu, P. Dewing, V. R. Harley, and E. Vilain. 2003. "Dimerization of SOX9 is required for chondrogenesis, but not for sex determination." Hum Mol Genet 12 (14):1755-65.

Cermenati, S., S. Moleri, S. Cimbro, P. Corti, L. Del Giacco, R. Amodeo, E. Dejana, P. Koopman, F. Cotelli, and M. Beltrame. 2008. "Sox18 and Sox7 play redundant roles in vascular development." Blood 111 (5):2657-66. doi: 10.1182/blood-2007-07-100412.

Corada, M., F. Orsenigo, M. F. Morini, M. E. Pitulescu, G. Bhat, D. Nyqvist, F. Breviario, V. Conti, A. Briot, M. L. Iruela-Arispe, R. H. Adams, and E. Dejana. 2013. "Sox17 is indispensable for acquisition and maintenance of arterial identity." Nat Commun 4:2609. doi: 10.1038/ncomms3609.

Dobin, A., C. A. Davis, F. Schlesinger, J. Drenkow, C. Zaleski, S. Jha, P. Batut, M. Chaisson, and T. R. Gingeras. 2013. "STAR: ultrafast universal RNA-seq aligner." Bioinformatics 29 (1):15-21. doi: 10.1093/bioinformatics/bts635.

Duong, T., K. Koltowska, C. Pichol-Thievend, L. Le Guen, F. Fontaine, K. A. Sm1th, V. Truong, R. Skoczylas, S. A. Stacker, M. G. Achen, P. Koopman, B. M. Hogan, and M. Francois. 2014. "VEGFD regulates blood vascular development by modulating SOX18 activity." Blood 123 (7): 1102-12. doi: 10.1182/blood-2013-04-495432.

Duong, T., S. T. Proulx, P. Luciani, J. C. Leroux, M. Detmar, P. Koopman, and M. Francois. 2012. "Genetic ablation of SOX18 function suppresses tumor lymphangiogenesis and metastasis of melanoma in mice." Cancer Res 72 (12):3105-14. doi: 10.1158/0008-5472.CAN-11-4026.

Durbin, L., C. Brennan, K. Shiomi, J. Cooke, A. Barrios, S. Shanmugalingam, B. Guthrie, R. Lindberg, and N. Holder. 1998. "Eph signaling is required for segmentation and differentiation of the somites." Genes Dev 12 (19): 3096-109.

Eom, B. W., M. J. Jo, M. C. Kook, K. W. Ryu, I. J. Choi, B. H. Nam, Y. W. Kim, and J. H. Lee. 2012. "The lymphangiogenic factor SOX 18: a key indicator to stage gastric tumor progression." Int J Cancer 131 (1):41-8. doi: 10.1002/ijc.26325.

Francois, M., A. Caprini, B. Hosking, F. Orsenigo, D. Wilhelm, C. Browne, K. Paavonen, T. Kamezis, R. Shayan, M. Downes, T. Davidson, D. Tutt, K. S. Cheah, S. A. Stacker, G. E. Muscat, M. G. Achen, E. Dejana, and P. Koopman. 2008. "Sox18 induces development of the lymphatic vasculature in mice." *Nature* 456 (7222):643-7. doi: 10.1038/nature07391.

Gagoski, Dejan, Sergey Mureev, Nichole Giles, Wayne Johnston, Mareike Dahmer-Heath, Dubravka Škalamera, Thomas J. Gonda, and Kirill Alexandrov. 2015. "Gateway-compatible vectors for high-throughput protein expression in pro- and eukaryotic cell-free systems." Journal of Biotechnology 195 (0):1-7. doi: http://dx-.doi.org/10.1016/j.jbiotec.2014.12.006.

Gambin, Y., N. Ariotti, K. A. McMahon, M. Bastiani, E. Sierecki, O. Kovtun, M. E. Polinkovsky, A. Magenau, W. Jung, S. Okano, Y. Zhou, N. Leneva, S. Mureev, W. Johnston, K. Gaus, J. F. Hancock, B. M. Collins, K. Alexandrov, and R. G. Parton. 2014. "Single-molecule analysis reveals self assembly and nanoscale segregation of two distinct cavin subcomplexes on caveolae." Elife 3:e01434. doi: 10.7554/eLife.01434.

Gormally, M. V., T. S. Dexheimer, G. Marsico, D. A. Sanders, C. Lowe, D. Matak-Vinkovic, S. Michael, A. Jadhav, G. Rai, D. J. Maloney, A. Simeonov, and S. Balasubramanian. 2014. "Suppression of the FOXM1 transcriptional programme via novel small molecule inhibition." Nat Commun 5:5165. doi: 10.1038/ncomms6165.

Hermkens, D. M., A. van Impel, A. Urasaki, J. Bussmann, H. J. Duckers, and S. Schulte-Merker. 2015. "Sox7 controls arterial specification in conjunction with hey2 and efnb2 function." Development 142 (9):1695-704. doi: 10.1242/dev.117275.

Herpers, R., E. van de Kamp, H. J. Duckers, and S. Schulte-Merker. 2008. "Redundant roles for sox7 and sox18 in arteriovenous specification in zebrafish." Circ Res 102 (1):12-5. doi: 10.1161/CIRCRESAHA.107.166066.

Hogan, B. M., F. L. Bos, J. Bussmann, M. Witte, N. C. Chi, H. J. Duckers, and S. Schulte-Merker. 2009. "Ccbe1 is required for embryonic lymphangiogenesis and venous sprouting." Nat Genet 41 (4):396-8. doi: 10.1038/ng.321.

Hosking, B., M. Francois, D. Wilhelm, F. Orsenigo, A. Caprini, T. Svingen, D. Tutt, T. Davidson, C. Browne, E. Dejana, and P. Koopman. 2009. "Sox7 and Sox17 are strain-specific modifiers of the lymphangiogenic defects caused by Sox18 dysfunction in mice." Development 136 (14):2385-91. doi: 10.1242/dev.034827.

Hosking, B. M., S. C. Wang, S. L. Chen, S. Penning, P. Koopman, and G. E. Muscat. 2001. "SOX18 directly interacts with MEF2C in endothelial cells." Biochem Biophys Res Commun 287 (2):493-500. doi: 10.1006/bbrc.2001.5589.

Hosking, B. M., S. C. Wang, M. Downes, P. Koopman, and G. E. Muscat. 2004. "The VCAM-1 gene that encodes the vascular cell adhesion molecule is a target of the Sry-related high mobility group box gene, Sox18." J Biol Chem 279 (7):5314-22. doi: 10.1074/jbc.M308512200.

Illendula, A., J. A. Pulikkan, H. Zong, J. Grembecka, L. Xue, S. Son, Y. Zhou, A. Boulton, A. Kuntimaddi, Y. Gao, R. A. Rajewski, M. L. Guzman, L. H. Castilla, and J. H. Bushweller. 2015. "Chemical biology. A small-molecule inhibitor of the aberrant transcription factor CBFbeta-SMMHC delays leukemia in mice." Science 347 (6223): 779-84. doi: 10.1126/science.aaa0314.

Jauch, R., I. Aksoy, A. P. Hutchins, C. K. Ng, X. F. Tian, J. Chen, P. Palasingam, P. Robson, L. W. Stanton, and P. R. Kolatkar. 2011. "Conversion of Sox17 into a pluripotency reprogramming factor by reengineering its association with Oct4 on DNA." Stem Cells 29 (6):940-51. doi: 10.1002/stem.639.

Jethon, A., B. Pula, M. Olbromski, B. Werynska, B. Muszczynska-Bernhard, W. Witkiewicz, P. Dziegiel, and M. Podhorska-Okolow. 2015. "Prognostic significance of SOX18 expression in non-small cell lung cancer." Int J Oncol 46 (1):123-32. doi: 10.3892/ijo.2014.2698.

Kim, K., I. K. Kim, J. M. Yang, E. Lee, B. I. Koh, S. Song, J. Park, S. Lee, C. Choi, J. W. Kim, Y. Kubota, G. Y. Koh, and I. Kim. 2016. "SoxF Transcription Factors Are Positive Feedback Regulators of VEGF Signaling." Circ Res 119 (7):839-52. doi: 10.1161/CIRCRESAHA.116.308483.

Kovtun, O., S. Mureev, W. Jung, M. H. Kubala, W. Johnston, and K. Alexandrov. 2011. "Leishmania cell-free protein expression system." Methods 55 (1):58-64. doi: 10.1016/j.ymeth.2011.06.006.

Lawson, N. D., and B. M. Weinstein. 2002. "In vivo imaging of embryonic vascular development using transgenic zebrafish." Dev Biol 248 (2):307-18.

Lefebvre, V., W. Huang, V. R. Harley, P. N. Goodfellow, and B. de Crombrugghe. 1997. "SOX9 is a potent activator of the chondrocyte-specific enhancer of the pro alpha1 (II) collagen gene." Mol Cell Biol 17 (4):2336-46.

Love, M. I., W. Huber, and S. Anders. 2014. "Moderated estimation of fold change and dispersion for RNA-seq data with DESeq2." Genome Biol 15 (12):550. doi: 10.1186/s13059-014-0550-8.

Matsui, T., M. Kanai-Azuma, K. Hara, S. Matoba, R. Hiramatsu, H. Kawakami, M. Kurohmaru, P. Koopman, and Y. Kanai. 2006. "Redundant roles of Sox17 and Sox18 in postnatal angiogenesis in mice." J Cell Sci 119 (Pt 17):3513-26. doi: 10.1242/jcs.03081.

Mitchell, R. E., L. F. Huitema, R. E. Skinner, L. H. Brunt, C. Severn, S. Schulte-Merker, and C. L. Hammond. 2013.

"New tools for studying osteoarthritis genetics in zebrafish." Osteoarthritis Cartilage 21 (2):269-78. doi: 10.1016/j.joca.2012.11.004.

Mittal, D., A. Young, K. Stannard, M. Yong, M. W. Teng, B. Allard, J. Stagg, and M. J. Smyth. 2014. "Antimetastatic effects of blocking PD-1 and the adenosine A2A receptor." Cancer Res 74 (14):3652-8. doi: 10.1158/0008-5472.CAN-14-0957.

Moellering, R. E., M. Comejo, T. N. Davis, C. Del Bianco, J. C. Aster, S. C. Blacklow, A. L. Kung, D. G. Gilliland, G. L. Verdine, and J. E. Bradner. 2009. "Direct inhibition of the NOTCH transcription factor complex." Nature 462 (7270):182-8. doi: 10.1038/nature08543.

Mohammed, H., C. D'Santos, A. A. Serandour, H. R. Ali, G. D. Brown, A. Atkins, O. M. Rueda, K. A. Holmes, V. Theodorou, J. L. Robinson, W. Zwart, A. Saadi, C. S. Ross-Innes, S. F. Chin, S. Menon, J. Stingl, C. Palmieri, C. Caldas, and J. S. Carroll. 2013. "Endogenous purification reveals GREB1 as a key estrogen receptor regulatory factor." Cell Rep 3 (2):342-9. doi: 10.1016/j.celrep.2013.01.010.

Mureev, S., O. Kovtun, U. T. Nguyen, and K. Alexandrov. 2009. "Species-independent translational leaders facilitate cell-free expression." Nat Biotechnol 27 (8):747-52. doi: 10.1038/nbt.1556.

Pendeville, H., M. Winandy, I. Manfroid, O. Nivelles, P. Motte, V. Pasque, B. Peers, I. Struman, J. A. Martial, and M. L. Voz. 2008. "Zebrafish Sox7 and Sox18 function together to control arterial-venous identity." Dev Biol 317 (2):405-16. doi: 10.1016/j.ydbio.2008.01.028.

Pula, B., M. Olbromski, A. Wojnar, A. Gomulkiewicz, W. Witkiewicz, M. Ugorski, P. Dziegiel, and M. Podhorska-Okolow. 2013. "Impact of SOX18 expression in cancer cells and vessels on the outcome of invasive ductal breast carcinoma." Cell Oncol (Dordr) 36 (6):469-83. doi: 10.1007/s13402-013-0151-7.

Robinson, A. S., S. C. Materna, R. M. Barnes, S. De Val, S. M. Xu, and B. L. Black. 2014. "An arterial-specific enhancer of the human endothelin converting enzyme 1 (ECE1) gene is synergistically activated by Sox17, FoxC2, and Etv2." Dev Biol 395 (2):379-89. doi: 10.1016/j.ydbio.2014.08.027.

Sacilotto, N., R. Monteiro, M. Fritzsche, P. W. Becker, L. Sanchez-Del-Campo, K. Liu, P. Pinheiro, I. Ratnayaka, B. Davies, C. R. Goding, R. Patient, G. Bou-Gharios, and S. De Val. 2013. "Analysis of Dll4 regulation reveals a combinatorial role for Sox and Notch in arterial development." Proc Natl Acad Sci USA 110 (29):11893-8. doi: 10.1073/pnas.1300805110.

Sarkar, A., and K. Hochedlinger. 2013. "The sox family of transcription factors: versatile regulators of stem and progenitor cell fate." Cell Stem Cell 12 (1):15-30. doi: 10.1016/j.stem.2012.12.007.

Schmidt, D., M. D. Wilson, C. Spyrou, G. D. Brown, J. Hadfield, and D. T. Odom. 2009. "ChIP-seq: using high-throughput sequencing to discover protein-DNA interactions." Methods 48 (3):240-8. doi: 10.1016/j.ymeth.2009.03.001.

Sierecki, E., N. Giles, M. Polinkovsky, M. Moustaqil, K. Alexandrov, and Y. Gambin. 2013. "A cell-free approach to accelerate the study of protein-protein interactions in vitro." Interface Focus 3 (5):20130018. doi: 10.1098/rsfs.2013.0018.

Sierecki, E., L. M. Stevers, N. Giles, M. E. Polinkovsky, M. Moustaqil, S. Mureev, W. A. Johnston, M. Dahmer-Heath, D. Skalamera, T. J. Gonda, B. Gabrielli, B. M. Collins, K. Alexandrov, and Y. Gambin. 2014. "Rapid mapping of interactions between Human SNX-BAR proteins measured in vitro by AlphaScreen and single-molecule spectroscopy." Mol Cell Proteomics 13 (9):2233-45. doi: 10.1074/mcp.M113.037275.

Song, H. D., X. J. Sun, M. Deng, G. W. Zhang, Y. Zhou, X. Y. Wu, Y. Sheng, Y. Chen, Z. Ruan, C. L. Jiang, H. Y. Fan, L. I. Zon, J. P. Kanki, T. X. Liu, A. T. Look, and Z. Chen. 2004. "Hematopoietic gene expression profile in zebrafish kidney marrow." Proc Natl Acad Sci USA 101 (46): 16240-5. doi: 10.1073/pnas.0407241101.

Thisse, C., and B. Thisse. 2008. "High-resolution in situ hybridization to wholemount zebrafish embryos." Nat Protoc 3 (1):59-69. doi: 10.1038/nprot.2007.514.

Wythe, J. D., L. T. Dang, W. P. Devine, E. Boudreau, S. T. Artap, D. He, W. Schachterle, D. Y. Stainier, P. Oettgen, B. L. Black, B. G. Bruneau, and J. E. Fish. 2013. "ETS factors regulate Vegf-dependent arterial specification." Dev Cell 26 (1):45-58. doi: 10.1016/j.devcel.2013.06.007.

Yang, H., S. Lee, S. Lee, K. Kim, Y. Yang, J. H. Kim, R. H. Adams, J. M. Wells, S. J. Morrison, G. Y. Koh, and I. Kim. 2013. "Sox17 promotes tumor angiogenesis and destabilizes tumor vessels in mice." J Clin Invest 123 (1):418-31. doi: 10.1172/JCI64547.

Young, N., C. N. Hahn, A. Poh, C. Dong, D. Wilhelm, J. Olsson, G. E. Muscat, P. Parsons, J. R. Gamble, and P. Koopman. 2006. "Effect of disrupted SOX18 transcription factor function on tumor growth, vascularization, and endothelial development." J Natl Cancer Inst 98 (15): 1060-7. doi: 10.1093/jnci/djj299.

Zhang, X., P. Yue, B. D. Page, T. Li, W. Zhao, A. T. Namanja, D. Paladino, J. Zhao, Y. Chen, P. T. Gunning, and J. Turkson. 2012. "Orally bioavailable small-molecule inhibitor of transcription factor Stat3 regresses human breast and lung cancer xenografts." Proc Natl Acad Sci USA 109 (24):9623-8. doi: 10.1073/pnas.1121606109.

Zhang, Y., S. Huang, W. Dong, L. Li, Y. Feng, L. Pan, Z. Han, X. Wang, G. Ren, D. Su, B. Huang, and J. Lu. 2009. "SOX7, down-regulated in colorectal cancer, induces apoptosis and inhibits proliferation of colorectal cancer cells." Cancer Lett 277 (1):29-37. doi: 10.1016/j.canlet.2008.11.014.

The invention claimed is:

1. A method of treatment of an angiogenesis and/or lymphangiogenesis-related disease, disorder or condition, comprising administering to a subject an effective amount of a compound of Formula 1:

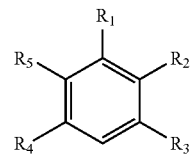

Formula (I)

wherein, $R_1$ is selected from the group consisting of OH and $OR_6$ wherein $R_6$ is $C_{1-4}$alkyl;

$R_2$ is selected from the group consisting of H, $COOR_7$, and $C(O)NR_8R_9$ wherein $R_7$, $R_8$ and $R_9$ are independently selected from the group consisting of H and $C_{1-4}$alkyl;

$R_3$ is L-A wherein L is a linker selected from the group consisting of $C_{2-8}$alkyl, $C_{2-8}$ alkenyl and $C_{2-8}$alkoxyalkyl and A is an optionally substituted naphthyl;

$R_4$ is selected from the group consisting of H, $OR_{10}$, halo and $C_{1-4}$alkyl wherein $R_{10}$ is selected from the group consisting of H and $C_{1-4}$alkyl; and $R_5$ is selected from the group consisting of H, $OR_{11}$, halo and $C_{1-4}$alkyl wherein $R_{11}$ is selected from the group consisting of H and $C_{1-4}$alkyl;

or a pharmaceutically effective salt, solvate or prodrug thereof; and wherein the angiogenesis and/or lymphangiogenesis-related disease, disorder or condition is a SOX7, SOX17, or SOX18-dependent cancer selected from the group consisting of sarcomas, carcinomas, lymphomas, leukemias, and blastomas.

2. The method according to claim 1, wherein the cancer is SOX18-dependent and is selected from the group consisting of prostate cancer, breast cancer, lung cancer, bladder cancer, renal cancer, ovarian cancer, cervical cancer, uterine cancer, colon cancer, colorectal cancer, gastric cancer, head and neck cancer, liver cancer, kidney cancer, skin cancer, pancreatic cancer, pituitary cancer, musculoskeletal cancer, hemangioma, angioma, angiosarcoma, hepatoma, and hepatocellular carcinoma.

3. The method according to claim 2, wherein cancer metastasis is inhibited.

4. The method according to claim 1, wherein the compound of Formula I selectively inhibits SOX18-mediated transcription.

5. The method according to claim 1, wherein the compound of Formula I inhibits both DNA binding and transcription factor protein partner recruitment of SOX18.

6. The method according to claim 1, wherein the compound of Formula I inhibits SOX18 homodimerisation.

7. The method according to claim 1, wherein the compound of Formula I inhibits SOX18-RBPJ heterodimerisation.

8. The method according to claim 1, wherein for the compound of Formula 1:

$R_1$ is selected from the group consisting of OH and $OR_6$ wherein $R_6$ is $C_{1-4}$alkyl;

$R_2$ is selected from the group consisting of H, $COOR_7$, and $C(O)NR_8R_9$ wherein $R_7$, $R_8$ and $R_9$ are independently selected from H and $C_{1-4}$alkyl;

$R_3$ is L-A wherein L is a linker selected from the group consisting of $C_{2-8}$alkyl, $C_{2-8}$ alkenyl and $C_{2-8}$alkoxyalkyl and A is an optionally substituted naphthyl, and wherein the substituted groups are selected from the group consisting of halo, $C_{1-4}$alkyl, $OC_{1-4}$alkyl, $NH_2$, $NH(C_{1-4}$alkyl), and $N(C_{1-4}$alkyl$)_2$;

$R_4$ is selected from the group consisting of H, $OR_{10}$, halo and $C_{1-4}$alkyl wherein $R_{10}$ is selected from H and $C_{1-4}$alkyl; and $R_5$ is selected from the group consisting of H, $OR_{11}$, halo and $C_{1-4}$alkyl wherein $R_{11}$ is selected from the group consisting of H and $C_{1-4}$alkyl.

9. The method according to claim 1, wherein for the compound of Formula 1:

$R_1$ is selected from the group consisting of OH and $OR_6$ wherein $R_6$ is $C_{1-4}$alkyl;

$R_2$ is selected from the group consisting of $COOR_7$ and $C(O)NR_8R_9$ wherein $R_7$, $R_8$ and $R_9$ are independently selected from the group consisting of H and $C_{1-4}$alkyl;

$R_3$ is L-A wherein L is a linker selected from the group consisting of $C_{2-8}$alkyl, $C_{2-8}$ alkenyl and $C_{2-8}$alkoxyalkyl and A is an optionally substituted naphthyl;

$R_4$ is selected from the group consisting of H, $OR_{10}$, halo and $C_{1-4}$alkyl wherein $R_{10}$ is selected from the group consisting of H and $C_{1-4}$alkyl; and $R_5$ is H.

10. The method according to claim 1, wherein for the compound of Formula 1:

$R_1$ is selected from the group consisting of OH and $OR_6$ wherein $R_6$ is $C_{1-4}$alkyl;

$R_2$ is selected from the group consisting of H, $COOR_7$, and $C(O)NR_8R_9$ wherein $R_7$, $R_8$ and $R_9$ are independently selected from the group consisting of H and $C_{1-4}$alkyl;

$R_3$ is L-A wherein L is a linker selected from the group consisting of $C_{2-8}$alkyl, $C_{2-8}$ alkenyl and $C_{2-8}$alkoxyalkyl and A is selected from the group consisting of an unsubstituted naphthyl or a naphthyl substituted with one or more groups selected from the group consisting of halo, $C_{1-4}$alkyl, $OC_{1-4}$alkyl, $NH_2$, $NH(C_{1-4}$alkyl), and $N(C_{1-4}$alkyl$)_2$;

$R_4$ is selected from the group consisting of H, $OR_{10}$, halo and $C_{1-4}$alkyl wherein $R_{10}$ is selected from the group consisting of H and $C_{1-4}$alkyl; and $R_5$ is selected from the group consisting of H, $OR_{11}$, halo and $C_{1-4}$alkyl wherein $R_{11}$ is selected from the group consisting of H and $C_{1-4}$alkyl.

11. The method according to claim 1, wherein for the compound of Formula 1:

$R_1$ is selected from the group consisting of OH and $OR_6$ wherein $R_6$ is $C_{1-4}$alkyl;

$R_2$ is selected from the group consisting of $COOR_7$ and $C(O)NR_8R_9$ wherein $R_7$, $R_8$ and $R_9$ are independently selected from the group consisting of H and $C_{1-4}$alkyl;

$R_3$ is L-A wherein L is a linker selected from the group consisting of $C_{2-8}$alkyl, $C_{2-8}$ alkenyl and $C_{2-8}$alkoxyalkyl and A is an optionally substituted naphthyl;

$R_4$ is H; and $R_5$ is H.

12. The method according to claim 1, wherein for the compound of Formula 1:

$R_1$ is OH;

$R_2$ is $COOR_7$, wherein $R_7$ is selected from the group consisting of H and $C_{1-4}$alkyl;

$R_3$ is L-A wherein L is a linker selected from the group consisting of $C_{2-8}$alkyl, $C_{2-8}$ alkenyl and $C_{2-8}$alkoxyalkyl and A is an optionally substituted naphthyl;

$R_4$ is H; and $R_5$ is H.

13. The method according to claim 1, wherein for the compound of Formula 1:

$R_1$ is OH;

$R_2$ is COOH;

$R_3$ is L-A wherein L is a linker selected from the group consisting of $C_{2-8}$alkyl, $C_{2-8}$ alkenyl and $C_{2-8}$alkoxyalkyl and A is an optionally substituted naphthyl;

$R_4$ is H; and $R_5$ is H.

14. The method according to claim 1, wherein for the compound of Formula 1:

$R_1$ is OH;

$R_2$ is COOH;

$R_3$ is L-A wherein L is $C_{2-8}$alkyl and A is an optionally substituted naphthyl;

$R_4$ is H; and $R_5$ is H.

15. The method according to claim 1, wherein for the compound of Formula 1:

$R_1$ is OH;

$R_2$ is COOH;

$R_3$ is L-A wherein L is $C_{2-8}$alkyl and A is an unsubstituted naphthyl or a naphthyl substituted with one or more groups selected from the group consisting of halo, $C_{1-4}$ alkyl, $OC_{1-4}$alkyl, $NH_2$, $NH(C_{1-4}$alkyl), and $N(C_{1-4}$alkyl$)_2$;

$R_4$ is H; and $R_5$ is H.

* * * * *